US012668629B2

(12) United States Patent
Streuli et al.

(10) Patent No.: US 12,668,629 B2
(45) Date of Patent: *Jun. 30, 2026

(54) METHODS OF USING ANTI-TREM2 ANTIBODIES

(71) Applicant: Portsmouth Merger Sub II, LLC, Boston, MA (US)

(72) Inventors: Michel Streuli, Atherton, CA (US); Leonard G. Presta, San Francisco, CA (US); Venkataraman Sriram, Berkeley, CA (US); Aritra Pal, San Carlos, CA (US); Nadine Jahchan, San Carlos, CA (US); Mikhail Binnewies, San Francisco, CA (US); Joshua L. Pollack, Richmond, CA (US); Xiaoyan Du, South San Francisco, CA (US)

(73) Assignee: PORTSMOUTH MERGER SUB II, LLC, Boston, MA (US)

( * ) Notice: Subject to any disclaimer, the term of this patent is extended or adjusted under 35 U.S.C. 154(b) by 1213 days.

This patent is subject to a terminal disclaimer.

(21) Appl. No.: 17/344,839

(22) Filed: Jun. 10, 2021

(65) Prior Publication Data

US 2021/0317211 A1 Oct. 14, 2021

Related U.S. Application Data

(63) Continuation of application No. PCT/US2019/065743, filed on Dec. 11, 2019, which is a continuation-in-part of application No. PCT/US2018/065026, filed on Dec. 11, 2018.

(60) Provisional application No. 62/889,990, filed on Aug. 21, 2019.

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61P 35/00* (2018.01); *A61K 2039/505* (2013.01); *C07K 2317/24* (2013.01); *C07K 2317/31* (2013.01); *C07K 2317/41* (2013.01); *C07K 2317/732* (2013.01); *C07K 2317/734* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,344,339 B1 | 2/2002 | Menrad et al. | |
| 7,777,008 B2 | 8/2010 | Ponath et al. | |
| 8,231,878 B2 | 7/2012 | Colonna et al. | |
| 8,901,281 B2 | 12/2014 | Ponath et al. | |
| 8,981,061 B2 | 3/2015 | Colonna et al. | |
| 9,696,312 B2 | 7/2017 | Suciu-Foca et al. | |
| 10,508,148 B2 * | 12/2019 | Streuli | .................. A61P 35/00 |
| 11,505,602 B2 * | 11/2022 | Streuli | .............. C07K 16/2818 |
| 12,428,481 B2 * | 9/2025 | Streuli | ............ G01N 33/57492 |
| 2007/0124833 A1 | 5/2007 | Abad et al. | |
| 2007/0269408 A1 | 11/2007 | Sung et al. | |
| 2010/0310560 A1 | 12/2010 | Colonna et al. | |
| 2011/0053863 A1 | 3/2011 | Lyman et al. | |
| 2011/0262348 A1 | 10/2011 | Movahedi et al. | |
| 2012/0093805 A1 | 4/2012 | Kubota | |
| 2012/0156280 A1 | 6/2012 | Dow et al. | |
| 2012/0276004 A1 | 11/2012 | Epstein et al. | |
| 2013/0150559 A1 | 6/2013 | Colonna et al. | |
| 2014/0045915 A1 | 2/2014 | Skog et al. | |
| 2014/0127211 A1 | 5/2014 | Geles et al. | |
| 2015/0191543 A1 | 7/2015 | Wu et al. | |
| 2017/0014526 A1 | 1/2017 | Geles et al. | |
| 2017/0240631 A1 | 8/2017 | Monroe et al. | |
| 2017/0291946 A1 | 10/2017 | Krummel et al. | |
| 2017/0304437 A1 | 10/2017 | Ellmark et al. | |
| 2017/0320946 A1 | 11/2017 | Colonna et al. | |
| 2017/0334977 A1 | 11/2017 | Butovsky et al. | |
| 2018/0037644 A1 | 2/2018 | Bloom et al. | |
| 2018/0334977 A1 | 11/2018 | Hattar et al. | |
| 2019/0010230 A1 | 1/2019 | Monroe et al. | |
| 2019/0040130 A1 | 2/2019 | Schwabe et al. | |

FOREIGN PATENT DOCUMENTS

| | | |
|---|---|---|
| CN | 107106679 A | 8/2017 |
| JP | 2009-527507 A | 7/2009 |
| WO | 2007/089942 A2 | 8/2007 |
| WO | 2007/089945 A2 | 8/2007 |
| WO | 2007/095729 A1 | 8/2007 |
| WO | 2013/174537 A1 | 11/2013 |
| WO | 2014/074942 A1 | 5/2014 |

(Continued)

OTHER PUBLICATIONS

Tessarz et al., "The TREM-1/DAP12 pathway." Immunology letters 116, No. 2 (2008): 111-116.

Katzenelenbogen et al., "Coupled scRNA-seq and intracellular protein activity reveal an immunosuppressive role of TREM2 in cancer." Cell 182, No. 4 (2020): 872-885.

Molgora et al., "TREM2 modulation remodels the tumor myeloid landscape enhancing anti-PD-1 immunotherapy." Cell 182, No. 4 (2020): 886-900.

Dondelinger et al., "Understanding the significance and implications of antibody numbering and antigen-binding surface/residue definition." Frontiers in immunology 9 (2018): 2278, 15 pages.

Yun et al., "Research progress on the relationship between triggering receptor expressed on myeloid cells 1 and 2 and malignant tumors." Hua xi kou qiang yi xue za zhi=Huaxi kouqiang yixue zazhi=West China journal of stomatology 35, No. 6 (2017): 648-653.

(Continued)

*Primary Examiner* — Michael Szperka
(74) *Attorney, Agent, or Firm* — Goodwin Procter, LLP

(57) ABSTRACT

Provided herein are anti-TREM2 antibodies and related methods of making and using anti-TREM2 antibodies. Also provided are methods and compositions for enhancing an immune response and/or for the treatment of an immune-related condition in an individual, e.g., cancer, using an anti-TREM2 antibody or antigen binding fragment thereof.

17 Claims, 24 Drawing Sheets

Specification includes a Sequence Listing.

(56) References Cited

FOREIGN PATENT DOCUMENTS

| | | | | | |
|---|---|---|---|---|---|
| WO | 2014/135245 | A1 | 9/2014 | | |
| WO | 2015/035365 | A1 | 3/2015 | | |
| WO | 2015/103072 | A1 | 7/2015 | | |
| WO | WO-2016023019 | A2 | * 2/2016 | .............. | A61P 25/28 |
| WO | 2016/049641 | A1 | 3/2016 | | |
| WO | 2016/064895 | A1 | 4/2016 | | |
| WO | 2016/106221 | A1 | 6/2016 | | |
| WO | 2017/062672 | A2 | 4/2017 | | |
| WO | WO-2017058866 | A1 | * 4/2017 | ......... | C07K 16/2803 |
| WO | 2018/015573 | A2 | 1/2018 | | |
| WO | 2019/021233 | A1 | 1/2019 | | |
| WO | 2019/055841 | A1 | 3/2019 | | |
| WO | 2019/118513 | A1 | 6/2019 | | |
| WO | 2020/123664 | A1 | 6/2020 | | |

OTHER PUBLICATIONS

Kawabori et al., "Triggering receptor expressed on myeloid cells 2 (TREM2) deficiency attenuates phagocytic activities of microglia and exacerbates ischemic damage in experimental stroke." Journal of Neuroscience 35, No. 8 (2015): 3384-3396.

Zhang et al., "High TREM2 expression correlates with poor prognosis in gastric cancer." Human pathology, 72 (2018), pp. 91-99.

Zhang et al., Depletion of the triggering receptor expressed on myeloid cells 2 inhibits progression of renal cell carcinoma via regulating related protein expression and PTEN-PI3K/Akt pathway, Int. J. Oncol. Dec. 2016 49 (6) 2498-2506.

Bergers et al., Extrinsic regulators of epithelial tumor progrssion: metalloproteinases, Current Opinion in Genetics and Development, 2000, 10: 120-127.

Kelland, "Of mice and men,' values and liabilities of the athymic nude mouse model in anticancer drug development," Eur. J. Cancer, Apr. 2004, 40 (6): 827-836.

Schuh, "Trials, Tributlations, and Trends in Tumor Modeling in Mice," Toxicologic Pathology 2004; 32 (Suppl. 1): 53-66.

Dennis, "Off by a whisker," Nature. Aug. 7, 2006; 442: 739-741.

Gura, Systems for Identifying New Drugs are Often Faulty, Science, 1997; 278: 1041-1042.

Riemer et al., Matching of trastuzumab (Herceptin®) epitope mimics onto the surface of Her-2/neu—a new method of epitope defininition, Mol. Immunol. 2005; 42: 1121-1124.

Jiang et al., Novel Peptide Isolated from a Phage Display Peptide Library with Trastuzumab Can Mimic Antigen Epitope of HER-2, J. Biol. Chem. Feb. 11, 2005; 280 (6): 4656-4662.

Press et al., Ricin A-Chain Containing Immunotoxins Directed Against Different Epitopes on the CD2 Molecule Differ in Their Ability to Kill Normal and Malignant T Cells, J. Immunol. Dec. 15, 1988; 141 (12): 4410-4417.

Leblond et al., "The Amphipathic-Helical Repeats of Apolipoprotein A-I Are Responsible for Binding of High Density Lipoproteins to HepG2 Cells," J. Biol. Chem. Apr. 5, 1991; 266 (10): 6058-67.

Sano et al., Properties of Blocking and Non-blocking Monoclonal Antibodies Specific for Human Macrophage Galactose-type C-type Lectin (MGL/ClecSF10A/CD301), (J. Biochem. Jan. 2007; 141 (1): 127-36.

Wu et al., Anti-Vascular Endothelial Growth Factor Receptor-1 Antagonist Antibody as a Therapeutic Agent for Cancer, Clin. Can. Res. 2006; 12 (21): 6573-84.

Pettersen et al., CD47 Signals T Cell Death, J. Immunol. Jun. 15, 1999; 162 (12): 7031-7040.

Vuist et al., Two Distinct Mechanisms of Antitumor Activity Mediated by the Combination of Interleukin 2 and Monoclonal Antibodies, Cancer Res. Sep. 15, 1990; 50 (18): 5767-5772.

Kim et al., Both the Epitope Specificity and Isotope Are Important in the Antitumor Effect of Monoclonal Antibodies Against Her-2/Neu Antigen, Int. J. Cancer. 2002; 102: 428-434.

Masui et al., "Mechanism of Antitumor Activity in Mice for Anti-Epidermal Grouth Factor Receptor Monoclonal Antibodies with Different Isotypes," Cancer Res. Nov. 1986; 46 (11): 5592-5598.

Kipps et al., "Importance of Immunoglobulin Isotype in Human Antibody-Dependent, Cell-Mediated Cytotoxicity Directed by Murine Monoclonal Antibodies," (J. Exp. Med. Jan. 1, 1985; 161 (1): 1-17.

Lewis et al., "Differential reponses of human tumor cell lines to anti-p185HER2 monoclonal antibodies", Cancer Immunol. Immunother., Sep. 1993; 37 (4): 255-63.

Campbell et al., "Monoclonal antibody therapy for lymphoma," Blood Reviews. 2003; 17:143-52.

Song et al. "Dissecting intratumoral myeloid cell plasticity by single cell RNA-seq." Cancer Med. Jun. 8, 2019(6): 3072-3085.

Broz, M.L. et al., "Dissecting the Tumor Myeloid Compartment Reveals Rare Activating Antigen-Presenting Cells Critical for T Cell Immunity," Cancer Cell 26, Dec. 8, 2014, Errata, p. 938. I.

Broz, M.L. et al., "The Emerging Understanding of Myeloid Cells as Partners and Targets in Tumor Rejection", Cancer Immunology at the Crossroads: Experimental Immunotherapies. Cancer Immunology Research; Apr. 2015, vol. 3, Issue 4,pp. 313-319. Retrieved from the Internet: www.aacrjournals.org.

Cook et al., "MerTK inhibition in tumor leukocytes decreases tumor growth and metastasis", J. Clin Invest., Aug. 2013, vol. 123, Issue 8: pp. 3231-3242.

Cummings et al., "Mer950, a novel monoclonal antibody targeting MER receptor tyrosine kinase, decreases colony formation and increases chemosensitvity in non-small cell lung cancer" Oncotarget, Jun. 26, 2014, vol. 5, Issue 21: pp. 10434-104455. Retrieved from the Internet: www.impactjournals.com/oncotarget.

Duluc et al., "Tumor-associated leukemia inhibitory factor and IL-6 skew monocyte differentiation into tumor-associated macrophage-like cells", 2007 American Society of Hematology, Blood, Dec. 15, 2007, vol. 110, Issue 13, pp. 4319-4330.

Ford et al. "TREM and TREM-like receptors in inflammation and disease", Current Opinion in Immunology, 2009, vol. 21, pp. 38-46.

Nagai et al., "Targeting tumor-associated macrophages in an experimental glioma model with a recombinant immunotoxin to folate receptor b", Cancer Ummunol Immunother, 2009, vol. 58: pp. 1577-1586.

Ojalvo et al., "High-Density Gene Expression Analysis of Tumor-Associated Macrophages from Mouse Mammary Tumors", The American Journal of Pathology, Mar. 2009, vol. 174, Issue 3: pp. 1048-1064.

Ries et al., "Targeting Tumor-Associated Macrophages with Anti-CSF-1R Antibody Reveals a Strategy for Cancer Therapy", Cancer Cell 25, Jun. 16, 2014, pp. 846-859.

Rogers et al., "MER receptor tyrosine kinase inhibition impedes glioblastoma multiforme migration and alters cellular morphology", Oncogene, 2012, vol. 31, pp. 4171-4181.

Li et al., "Experimental animal modeling for immune-oncology", Pharmacology & Therapeutics 173, 2017, pp. 34-46.

Sanmamed et al., "Defining the optimal murine models to investigate immune checkpoint blockers and their combination with other immunotherapies", Annals of Oncology, Feb. 23, 2016, vol. 27, Issue 7: pp. 1190-1198.

Saito et al., "Prognostic Significance of CD169 Lymph Node Sinus Macrophages in Patients with Malignant Melanoma", Cancer Immunology Research Aug. 21, 2015, vol. 3, Issue 12: pp. 1356-1364. Published Online First. U.S. Appl. No. 15/514,471, Office Action, mailed Oct. 16, 2018.

Piccio et al., "Blockade of TREM-2 exacerbates experimental autoimmune encephalomyelitis", Eur. J. Immunol., May 2007, vol. 37: pp. 1290-1301.

Yao et al., "TREM-2 serves as a negative immune regulator through Syk pathway in an IL-10 dependent manner in lung cancer", Oncotarget, May 17, 2016, vol. 7, Issue 20: pp. 29620-29634.

Cheng et al., "TREM2-activating antibodies abrogate the negative pleiotropic effects of the Alzheimer's disease variant Trem2R47H on murine myeloid cell function", J. Biol. Chem, Aug. 10, 2018; vol. 293, Issue 32, pp. 12620-12633.

Bouchon et al., "A DAP12-mediated Pathway Regulates Expression of CC Chemokine Receptor 7 and Maturation of Human Dendritic Cells", J. Exp. Med., Oct. 15, 2001; vol. 194, Issue 8: pp. 1111-1122.

Hsieh et al, "A role for TREM2 ligands in the phagocytosis of apoptotic neuronal cells by microglia" J. Neurochem, Mar. 19, 2009, vol. 109: pp. 1144-1156.

(56) References Cited

OTHER PUBLICATIONS

Humphrey et al, "TREM2, a DAP12-Associated Receptor, Regulates Osteoclast Differentiation and Function," J. Bone Miner Res, Oct. 20, 2005, vol. 21, pp. 237-245.

Hamid et al., "Safety and Tumor Responses with Labrolizumab (Anti-PD-1) in Melanoma", The New England Journal of Medicine, Jun. 2, 2013 (Jun. 2, 2013), vol. 369, Issue 2, pp. 134-144.

Chavez-Galan, et al., "Much more than M1 and M2 macrophages, there are also CD169+ and TCR+ macrophages", Frontiers in Immunology, May 2015, vol. 6, Article 263: pp. 1-15.

Duluc, et al., "Interferon-g reverses the immunosuppressive and protumoral properties and prevents the generation of human tumor-associated macrophages", International Journal of Cancer, 2009, vol. 125, No. 2, pp. 367-373.

Graham, et al., "The TAM family: phosphatidylserine-sensing receptor tyrosine kinases gone awry in cancer", Nature Reviews, Cancer, Dec. 2014, vol. 14, No. 12: pp. 769-785.

Goding, Monoclonal Antibodies (Third Edition), 1996: pp. 72-100.

Rothlin, et al., "TAM Receptor Signaling in Immune Homeostasis", Annual Review of Immunology, 2015, vol. 33: pp. 355-391.

Suciu-Foca, et al., "Soluble Ig-Like Transcript 3 Inhibits Tumor Allograft Rejection in Humanized SCID Mice and T Cell Responses in Cancer Patients", The Journal of Immunology, 2007, vol. 178, No. 11: pp. 7432-7441.

Yao, et al., "Triggering receptor expressed on myeloid cells-2 (TREM-2) elicited by lung cancer cells to facilitate tumor immune evasion", Journal of Clinical Oncology, 2013, vol. 31, No. 15: pp. 2-3.

Nagai et al., "Production of a high-affinity monoclonal antibody reactive with folate receptors alpha and beta." Monoclonal antibodies in immunodiagnosis and immunotherapy 34, No. 3 (2015): 181-190.

PCT/US2019/065743—International Preliminary Report on Patentability, Jun. 8, 2021, 9 pages.

PCT/US2019/065743—Invitiation to Pay Additional Fees, Feb. 21, 2020, 2 pages.

Garraway et al., "Genomics-driven oncology: framework for an emerging paradigm." Journal of Clinical Oncology 31, No. 15 (2013): 1806-1814.

Almagro et al., "Humanization of antibodies." Front Biosci 13, No. 1 (2008): 1619-1633.

De Genst et al., "Antibody repertoire development in camelids." Developmental & Comparative Immunology 30, No. 1-2 (2006): 187-198.

Yoshinaga et al., "Ig L-chain shuffling for affinity maturation of phage library-derived human anti-human MCP-1 antibody blocking its chemotactic activity." Journal of biochemistry 143, No. 5 (2008): 593-601.

Cuende, et al., "Monoclonal antibodies against GARP/TGF -?1 complexes inhibit the immunosuppressive activity of human regulatory T cells in vivo", Sci Transl Med, Apr. 2015, vol. 7, No. 284: pp. 284ra56. doi: 10.1126/scitranslmed.aaa1983.

Varnum, et al., "A split-luciferase complementation, real-time reporting assay enables monitoring of the disease-associated transmembrane protein TREM2 in live cells", J Biol Chem, Jun. 2017, vol. 292, No. 25: pp. 10651-10663. doi: 10.1074/jbc.M116.759159. Epub May 10, 2017.

Kim, et al., "TREM2 promotes Abeta phagocytosis by upregulating C/EBPalpha-dependent CD36 expression in microglia", Scientific Reports, Sep. 2017, vol. 7, No. 1: pp. 11118. doi: 10.1038/s41598-017-11634-x.

U.S. Appl. No. 15/514,471—Notice of Allowance, Jun. 18, 2019, 16 pages.

U.S. Appl. No. 16/408,322—Notice of Allowance, Aug. 7, 2019, 14 pages.

U.S. Appl. No. 16/459,589—Non-Final Office Action, Aug. 5, 2021, 13 pages.

U.S. Appl. No. 16/459,589—Final Office Action, Nov. 19, 2021, 13 pages.

U.S. Appl. No. 16/601,233—Non-Final Office Action, Jan. 19, 2022, 27 pages.

U.S. Appl. No. 16/601,233—Notice of Allowance, Oct. 27, 2022, 4 pages.

U.S. Appl. No. 15/514,471—Non-Final Office Action, Oct. 16, 2018, 42 pages.

U.S. Appl. No. 16/459,589—Notice of Allowance, Jan. 11, 2022, 7 pages.

Published as US 2019/0309064 A1, U.S. Appl. No. 16/408,322, filed May 9, 2019, U.S. Pat. No. 10,508,148, Dec. 17, 2019, Grannted.

Published as US 2020/0140546 A1, U.S. Appl. No. 16/601,233, filed Oct. 19, 2019, U.S. Pat. No. 11,505,602, Nov. 22, 2022, Granted.

Published as US 2023/0287110 A1, U.S. Appl. No. 18/045,093, filed Oct. 7, 2022, Pending.

* cited by examiner

- Human PBMC stained with PI-7012
- Representative plots from 3 donors

| Tumor | Lymphocytes | gMDSCs | TAMs | Non-CD45 |
|---|---|---|---|---|
| Renal- clear cell (1) | 138* | NA** | 652 | 125.8 |
| Renal- metastatic papillary | -3 | NA | 370 | -41 |
| Renal- clear cell (2) | 10 | 37 | 2,225 | 13 |
| Renal- primary papillary | 76 | 294 | 1,107 | 1 |
| Mucinous adenocarcinoma | 11 | 105 | 3,588 | 1 |

Representative histograms of mucinous adenocarcinoma shown

* Numbers indicate staining index for each population defined as (anti-TREM2 – isotype control)
** NA= not assessed

FIG. 9F

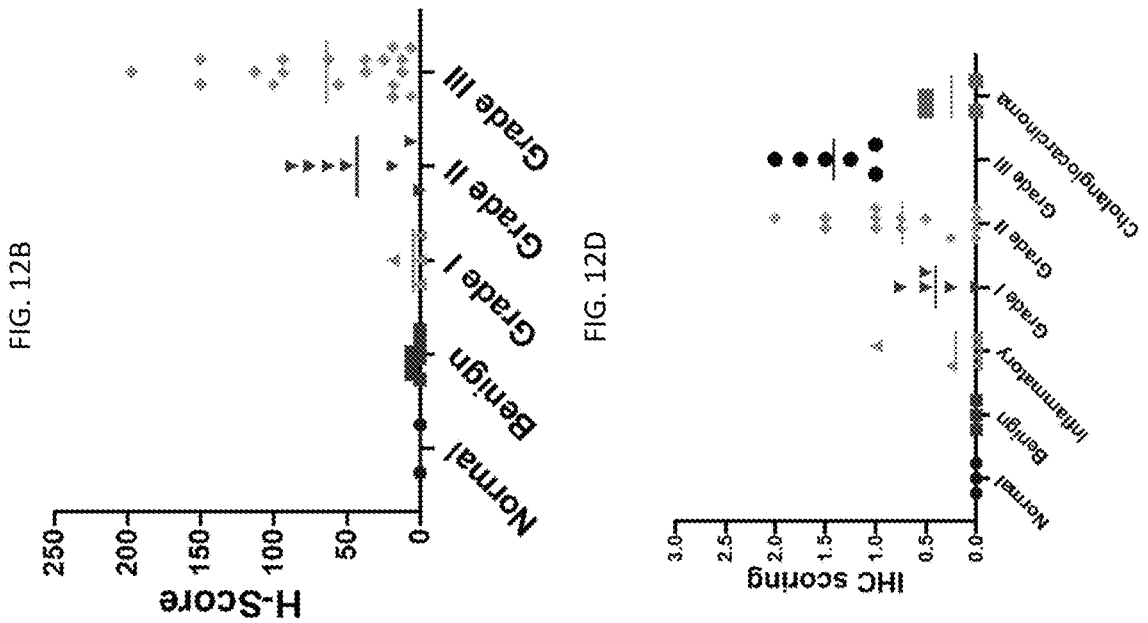
FIG. 12A
FIG. 12B
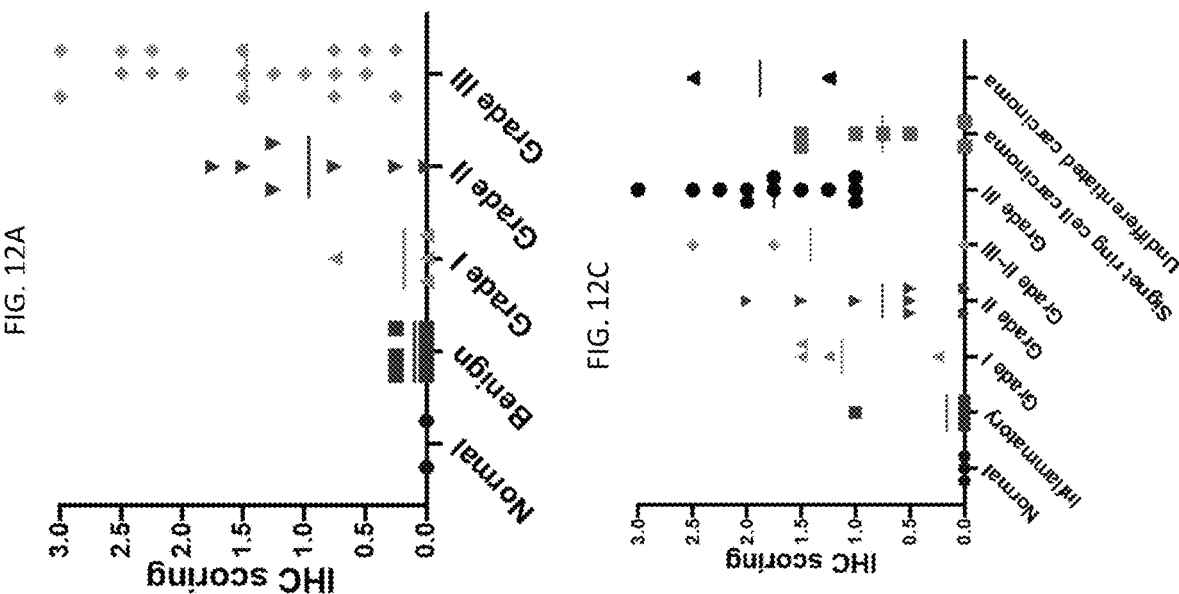
FIG. 12C
FIG. 12D

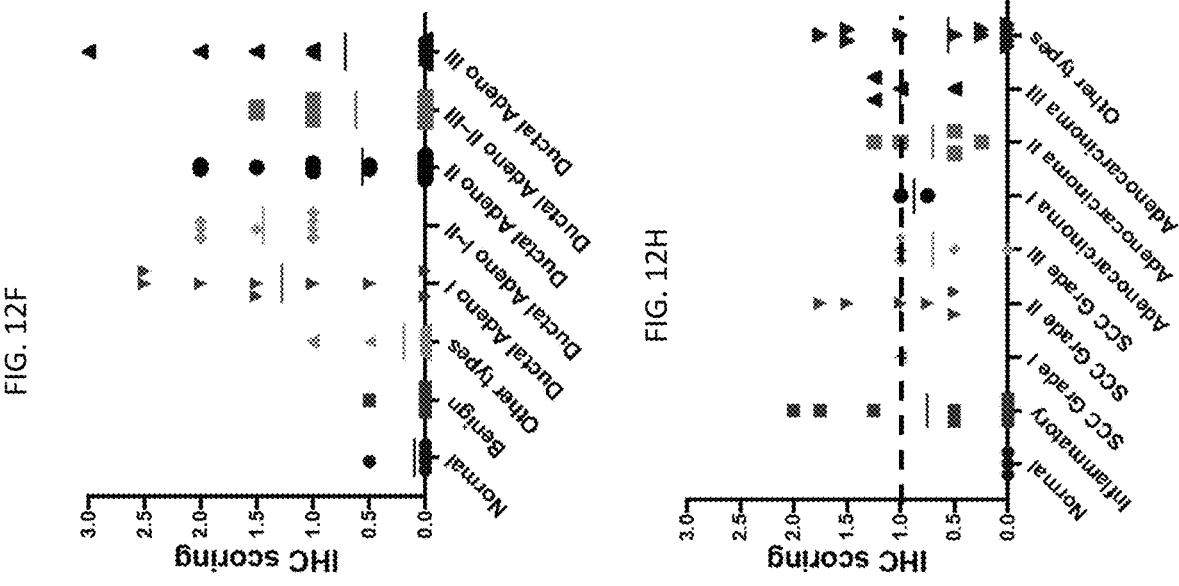
FIG. 12E
FIG. 12F
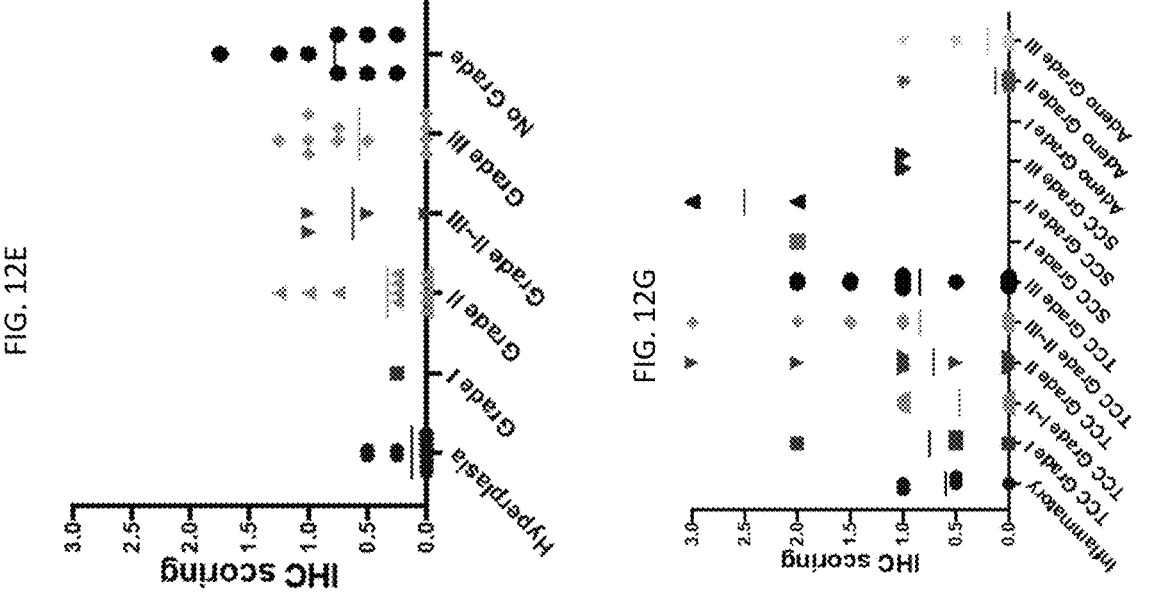
FIG. 12G
FIG. 12H

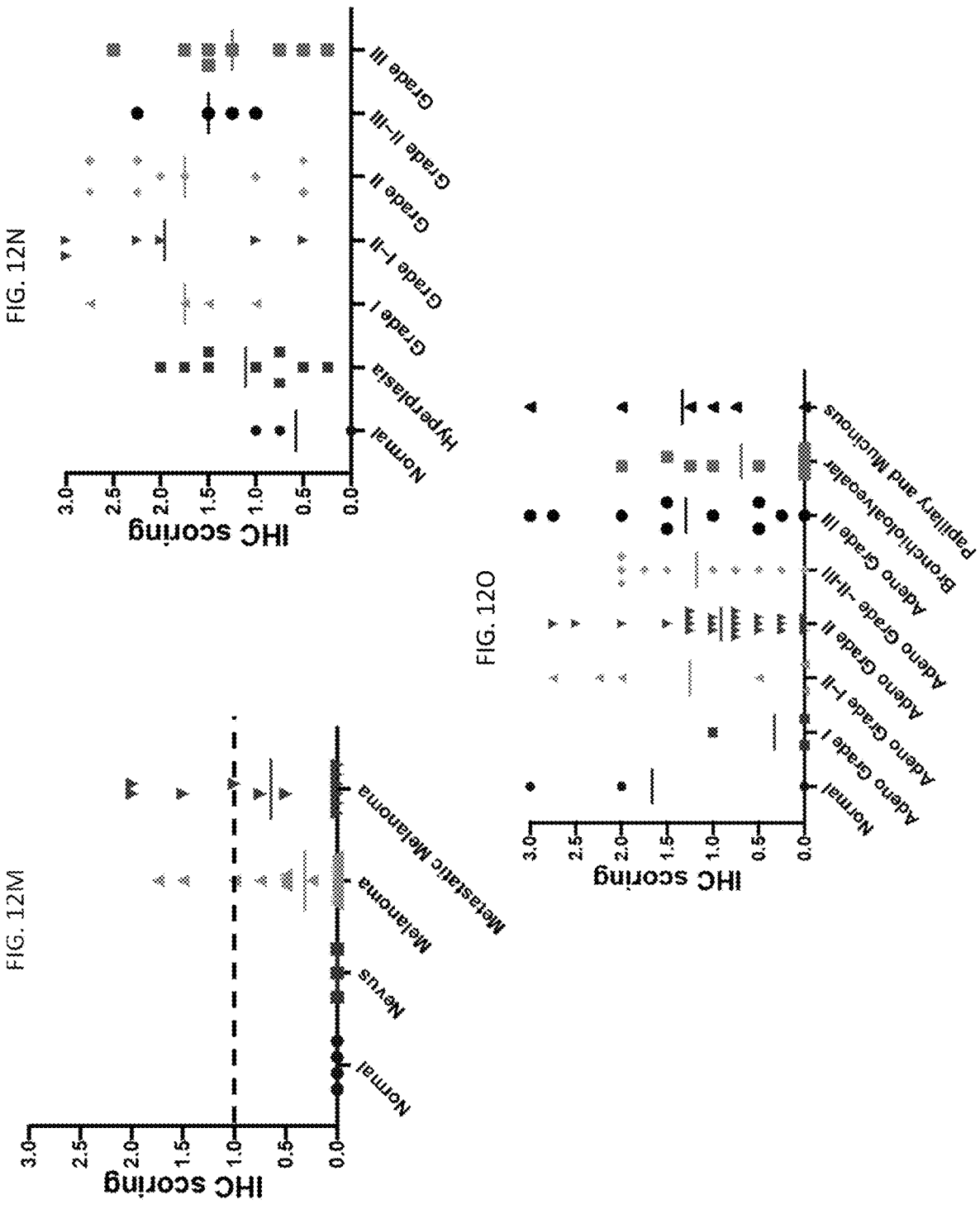

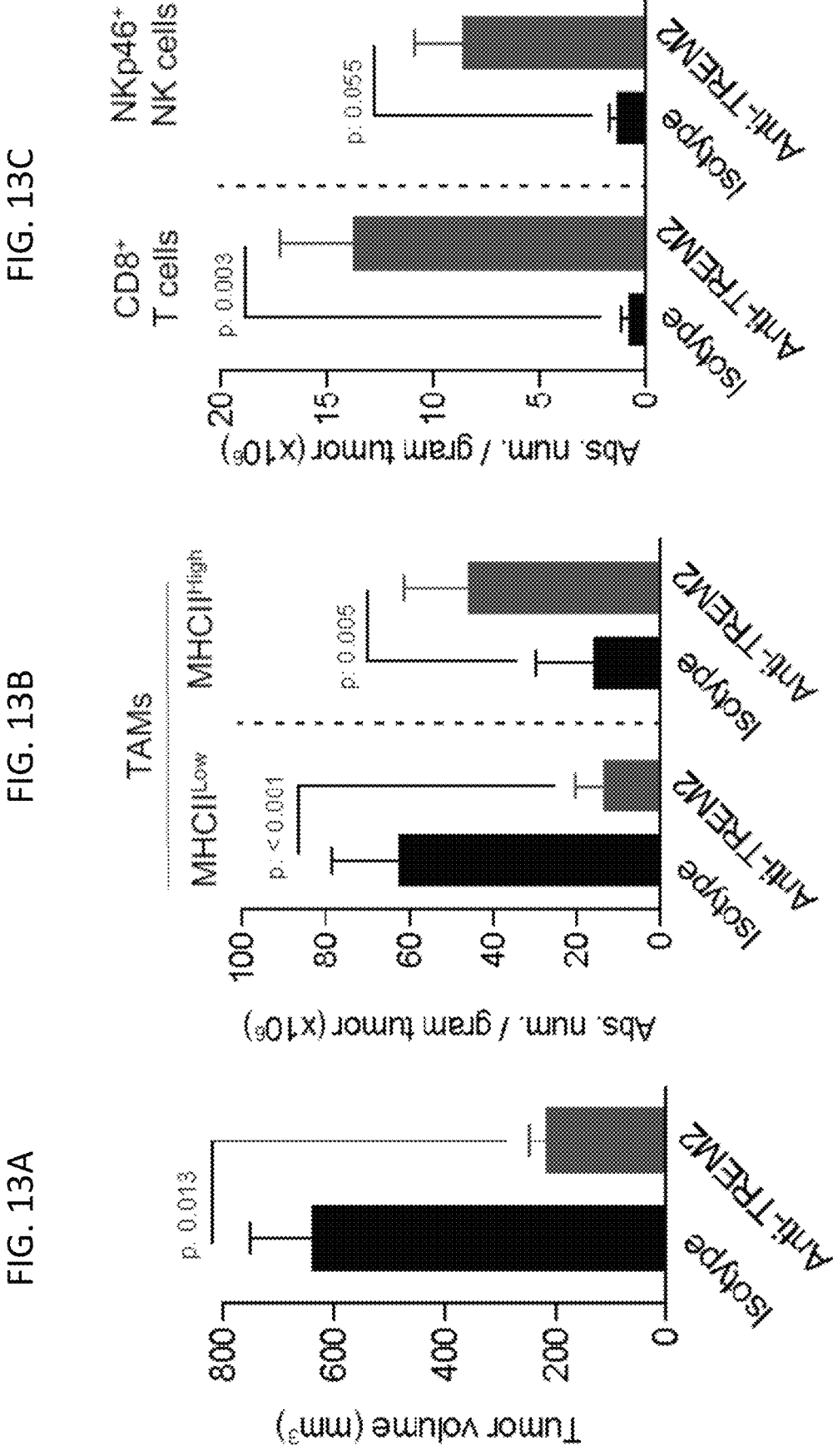

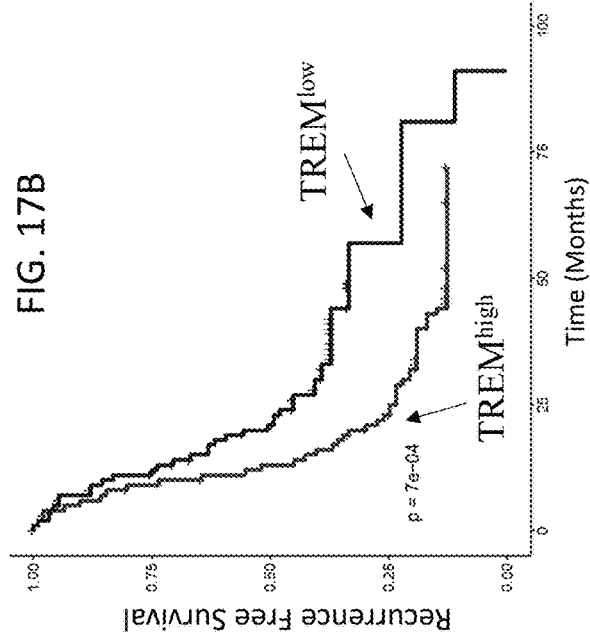
FIG. 17B
FIG. 17A
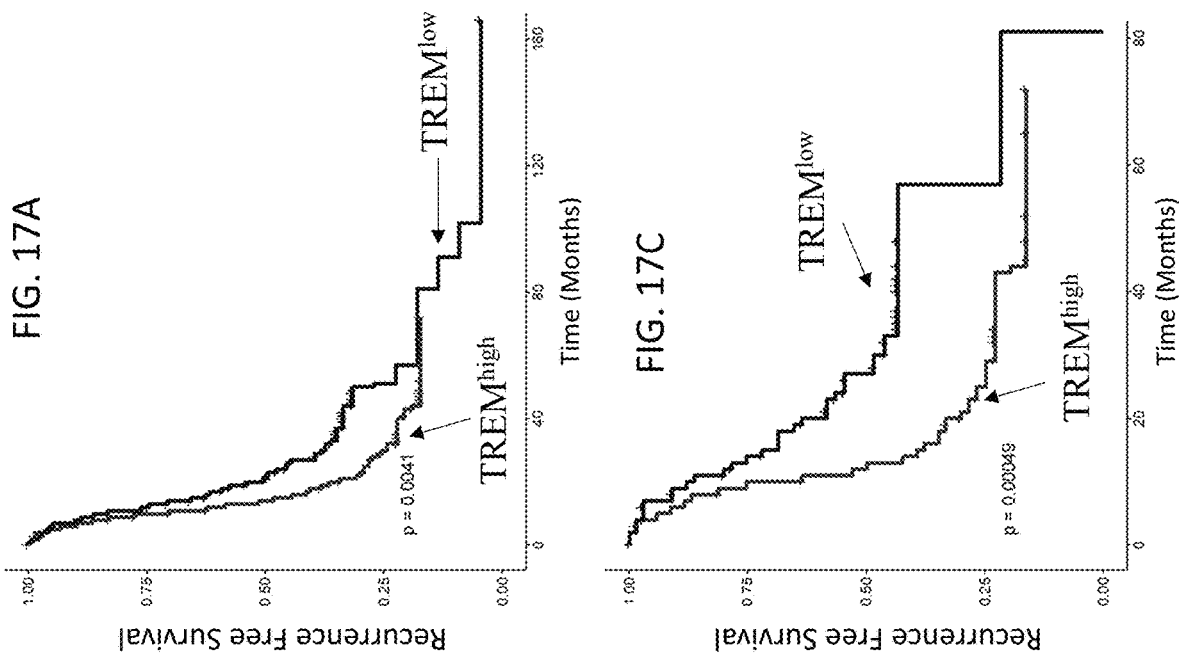
FIG. 17C

SEQUENCE LISTING

<160> NUMBER OF SEQ ID NOS: 59

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

-continued

```
Tyr Met Ala Trp Val Arg Gln Ala Pro Gly Lys Gly Leu Glu Trp Val
    35                  40                  45

Ser Ser Leu Thr Asn Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Trp Ala Gly Ser Gly Tyr Phe Asp Tyr Trp Gly Gln Gly
            100                 105                 110

Thr Leu Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Leu Ala Trp Tyr Gln Gln Lys Pro Gly Lys Ala Pro Lys Leu Leu Ile
        35                  40                  45

Tyr Tyr Thr Ser Asn Arg Phe Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Tyr Asn Ser Pro Trp
                85                  90                  95

Thr Phe Gly Gln Gly Thr Lys Leu Glu Ile Lys
            100                 105

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ser Ser Leu Thr Asn Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Thr Arg Glu Trp Ala Gly Ser Gly Tyr Phe Asp Tyr Trp Gly Gln Gly
            100                 105                 110

Thr Leu Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Met Thr Cys Lys Ala Ser Gln Asn Val Gly Asn Asn
            20                  25                  30

Leu Ala Trp Tyr Gln Gln Lys Pro Gly Lys Ala Pro Lys Leu Leu Leu
        35                  40                  45

Tyr Tyr Thr Ser Asn Arg Phe Thr Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Arg Ile Tyr Asn Ser Pro Trp
                85                  90                  95

Thr Phe Gly Gln Gly Thr Lys Leu Glu Leu Lys
            100                 105

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ala Ser Leu Thr Asn Ser Gly Gly Ser Thr Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Trp Ala Gly Ser Gly Tyr Phe Asp Tyr Trp Gly Gln Gly
            100                 105                 110

Thr Leu Val Thr Val Ser Ser
        115

<210> SEQ ID NO 6
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Leu Ala Trp Tyr Gln Gln Lys Pro Gly Lys Ala Pro Lys Leu Leu Ile
        35                  40                  45

Tyr Tyr Thr Ser Asn Arg Phe Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Tyr Asn Ser Pro Trp
                85                  90                  95

Thr Phe Gly Gln Gly Thr Lys Leu Glu Ile Lys
            100                 105

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ser Ser Leu Thr Asn Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Trp Ala Gly Ser Gly Tyr Phe Asp Tyr Trp Gly Gln Gly
            100                 105                 110

Thr Leu Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Leu Ala Trp Tyr Gln Gln Lys Pro Gly Lys Ala Pro Lys Leu Leu Ile

-continued

```
                35                    40                    45

Tyr Tyr Thr Ser Asn Arg Phe Thr Gly Val Pro Ser Arg Phe Ser Gly
    50                    55                    60

Ser Gly Ser Gly Thr Asp Phe Thr Leu Thr Ile Ser Ser Leu Gln Pro
65                    70                    75                    80

Glu Asp Phe Ala Thr Tyr Tyr Cys Gln Arg Ile Tyr Asn Ser Pro Trp
                85                    90                    95

Thr Phe Gly Gln Gly Thr Lys Leu Glu Ile Lys
            100                   105

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Ser Asn Tyr Tyr Met Ala
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Leu Thr Asn Ser Gly Gly Ser Thr Tyr
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Trp Ala Gly Ser Gly Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Val Gly Asn Asn Leu Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Tyr Thr Ser Asn Arg Phe Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ile Tyr Asn Ser Pro Trp
1               5

<210> SEQ ID NO 15
<211> LENGTH: 230
<212> TYPE: PRT
<213> ORGANISM: Homo sapiens

<400> SEQUENCE: 15

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
                20                  25                  30

Gln Val Ser Cys Pro Tyr Asp Ser Met Lys His Trp Gly Arg Arg Lys
            35                  40                  45

Ala Trp Cys Arg Gln Leu Gly Glu Lys Gly Pro Cys Gln Arg Val Val
        50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
                100                 105                 110

Leu His Gly Ser Glu Ala Asp Thr Leu Arg Lys Val Leu Val Glu Val
            115                 120                 125

Leu Ala Asp Pro Leu Asp His Arg Asp Ala Gly Asp Leu Trp Phe Pro
        130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
                180                 185                 190

Leu Trp Ala Ala Ala Trp His Gly Gln Lys Pro Gly Thr His Pro Pro
            195                 200                 205

Ser Glu Leu Asp Cys Gly His Asp Pro Gly Tyr Gln Leu Gln Thr Leu
        210                 215                 220

Pro Gly Leu Arg Asp Thr
225                 230

<210> SEQ ID NO 16
<211> LENGTH: 693
<212> TYPE: DNA
<213> ORGANISM: Homo sapiens

<400> SEQUENCE: 16
```

-continued

```
atggagcctc tccggctgct catcttactc tttgtcacag agctgtccgg agcccacaac      60
accacagtgt tccagggcgt ggcgggccag tccctgcagg tgtcttgccc ctatgactcc     120
atgaagcact gggggaggcg caaggcctgg tgccgccagc tgggagagaa gggcccatgc     180
cagcgtgtgg tcagcacgca caacttgtgg ctgctgtcct tcctgaggag gtggaatggg     240
agcacagcca tcacagacga taccctgggt ggcactctca ccattacgct gcggaatcta     300
caaccccatg atgcgggtct ctaccagtgc cagagcctcc atggcagtga ggctgacacc     360
ctcaggaagg tcctggtgga ggtgctggca gaccccctgg atcaccggga tgctggagat     420
ctctggttcc ccggggagtc tgagagcttc gaggatgccc atgtggagca cagcatctcc     480
aggagcctct ggaaggaga aatccccttc ccacccactt ccatccttct cctcctggcc     540
tgcatctttc tcatcaagat tctagcagcc agcgccctct gggctgcagc ctggcatgga     600
cagaagccag ggacacatcc acccagtgaa ctggactgtg ccatgaccc agggtatcag     660 ctccaaactc tgccagggct gagagacacg tga                                 693
```

<210> SEQ ID NO 17
<211> LENGTH: 227
<212> TYPE: PRT
<213> ORGANISM: Mus musculus

<400> SEQUENCE: 17

```
Met Gly Pro Leu His Gln Phe Leu Leu Leu Leu Ile Thr Ala Leu Ser
1               5                   10                  15

Gln Ala Leu Asn Thr Thr Val Leu Gln Gly Met Ala Gly Gln Ser Leu
            20                  25                  30

Arg Val Ser Cys Thr Tyr Asp Ala Leu Lys His Trp Gly Arg Arg Lys
        35                  40                  45

Ala Trp Cys Arg Gln Leu Gly Glu Glu Gly Pro Cys Gln Arg Val Val
    50                  55                  60

Ser Thr His Gly Val Trp Leu Leu Ala Phe Leu Lys Lys Arg Asn Gly
65                  70                  75                  80

Ser Thr Val Ile Ala Asp Asp Thr Leu Ala Gly Thr Val Thr Ile Thr
                85                  90                  95

Leu Lys Asn Leu Gln Ala Gly Asp Ala Gly Leu Tyr Gln Cys Gln Ser
            100                 105                 110

Leu Arg Gly Arg Glu Ala Glu Val Leu Gln Lys Val Leu Val Glu Val
        115                 120                 125

Leu Glu Asp Pro Leu Asp Asp Gln Asp Ala Gly Asp Leu Trp Val Pro
    130                 135                 140

Glu Glu Ser Ser Ser Phe Glu Gly Ala Gln Val Glu His Ser Thr Ser
145                 150                 155                 160

Arg Asn Gln Glu Thr Ser Phe Pro Pro Thr Ser Ile Leu Leu Leu Leu
                165                 170                 175

Ala Cys Val Leu Leu Ser Lys Phe Leu Ala Ala Ser Ile Leu Trp Ala
            180                 185                 190

Val Ala Arg Gly Arg Gln Lys Pro Gly Thr Pro Val Val Arg Gly Leu
        195                 200                 205

Asp Cys Gly Gln Asp Ala Gly His Gln Leu Gln Ile Leu Thr Gly Pro
    210                 215                 220

Gly Gly Thr
225
```

```
<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ser Ser Leu Thr Asn Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Trp Ala Gly Ser Gly Tyr Phe Asp Tyr Trp Gly Gln Gly
            100                 105                 110

Thr Leu Val Thr Val Ser Ser
        115

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ser Ser Leu Thr Asn Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Trp Ala Gly Ser Gly Tyr Phe Asp Tyr Trp Gly Gln Gly
            100                 105                 110

Thr Leu Val Thr Val Ser Ser
        115

<210> SEQ ID NO 20
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ala Ser Leu Thr Asn Ser Gly Gly Ser Thr Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Trp Ala Gly Ser Gly Tyr Phe Asp Tyr Trp Gly Gln Gly
            100                 105                 110

Thr Leu Val Thr Val Ser Ser
        115
```

```
<210> SEQ ID NO 21
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Leu Val Thr Val Ser Ser
            100                 105
```

```
<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Leu Ala Trp Tyr Gln Gln Lys Pro Gly Lys Ala Pro Lys Leu Leu Ile
        35                  40                  45

Tyr Tyr Thr Ser Asn Arg Phe Thr Gly Val Pro Ser Arg Phe Ser Gly
    50                  55                  60
```

-continued

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Tyr Asn Ser Pro Trp
                85                  90                  95

Thr Phe Gly Gln Gly Thr Lys Leu Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Ser Leu Ser Ala Ser Val Gly
1               5                   10                  15

Asp Arg Val Thr Met Thr Cys Lys Ala Ser Gln Asn Val Gly Asn Asn
                20                  25                  30

Leu Ala Trp Tyr Gln Gln Lys Pro Gly Lys Ala Pro Lys Leu Leu Leu
            35                  40                  45

Tyr Tyr Thr Ser Asn Arg Phe Thr Gly Val Pro Ser Arg Phe Ser Gly
        50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Arg Ile Tyr Asn Ser Pro Trp
                85                  90                  95

Thr Phe Gly Gln Gly Thr Lys Leu Glu Leu Lys
            100                 105

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Phe Gly Gln Gly Thr Lys Leu Glu Ile Lys
            100                 105

<210> SEQ ID NO 25
<211> LENGTH: 449
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ser Ser Leu Thr Asn Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Arg Glu Trp Ala Gly Ser Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
```

-continued

```
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 26
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Leu Ala Trp Tyr Gln Gln Lys Pro Gly Lys Ala Pro Lys Leu Leu Ile
        35                  40                  45

Tyr Tyr Thr Ser Asn Arg Phe Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Tyr Asn Ser Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
        20                  25                  30

Tyr Met Ala Trp Val Arg Gln Ala Pro Gly Lys Gly Leu Glu Trp Val
        35                  40                  45

Ser Ser Leu Thr Asn Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Trp Ala Gly Ser Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

-continued

```
Ala Leu His Asn His Tyr Thr Gln Lys Ser Leu Ser Leu Ser Pro Gly
    435                 440                 445

Lys

<210> SEQ ID NO 28
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Ser Leu Ser Ala Ser Val Gly
1               5                   10                  15

Asp Arg Val Thr Met Thr Cys Lys Ala Ser Gln Asn Val Gly Asn Asn
            20                  25                  30

Leu Ala Trp Tyr Gln Gln Lys Pro Gly Lys Ala Pro Lys Leu Leu Leu
        35                  40                  45

Tyr Tyr Thr Ser Asn Arg Phe Thr Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Arg Ile Tyr Asn Ser Pro Trp
                85                  90                  95

Thr Phe Gly Gln Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ala Ser Leu Thr Asn Ser Gly Gly Ser Thr Tyr Tyr Ala Asp Ser Val
```

```
            50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Trp Ala Gly Ser Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 30
<211> LENGTH: 214

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
                20                  25                  30

Leu Ala Trp Tyr Gln Gln Lys Pro Gly Lys Ala Pro Lys Leu Leu Ile
            35                  40                  45

Tyr Tyr Thr Ser Asn Arg Phe Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Tyr Asn Ser Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 31
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Tyr Met Ala Trp Val Arg Gln Ala Pro Gly Lys Gly Leu Glu Trp Val
            35                  40                  45

Ser Ser Leu Thr Asn Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Lys Glu Trp Ala Gly Ser Gly Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

```
<210> SEQ ID NO 32
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Leu Ala Trp Tyr Gln Gln Lys Pro Gly Lys Ala Pro Lys Leu Leu Ile
        35                  40                  45

Tyr Tyr Thr Ser Asn Arg Phe Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Tyr Asn Ser Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210
```

```
<210> SEQ ID NO 33
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33
```

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Ser Leu Thr Asn Ser Gly Gly Ser Thr Tyr Tyr Arg Asp Ser Val
    50                  55                  60

Lys Gly Arg Phe Thr Leu Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Arg Glu Trp Ala Gly Ser Gly Tyr Phe Asp Tyr Trp Gly Gln Gly
            100                 105                 110

Val Met Val Thr Val Ser Ser Ala Gln Thr Thr Ala Pro Ser Val Tyr
            115                 120                 125

Pro Leu Ala Pro Gly Cys Gly Asp Thr Thr Ser Ser Thr Val Thr Leu
        130                 135                 140
```

-continued

```
Gly Cys Leu Val Lys Gly Tyr Phe Pro Glu Pro Val Thr Val Thr Trp
145                 150                 155                 160

Asn Ser Gly Ala Leu Ser Ser Asp Val His Thr Phe Pro Ala Val Leu
                165                 170                 175

Gln Ser Gly Leu Tyr Thr Leu Thr Ser Ser Val Thr Ser Ser Thr Trp
            180                 185                 190

Pro Ser Gln Thr Val Thr Cys Asn Val Ala His Pro Ala Ser Ser Thr
            195                 200                 205

Lys Val Asp Lys Lys Val Glu Arg Arg Asp Gly Gly Ile Gly His Lys
        210                 215                 220

Cys Pro Thr Cys Pro Thr Cys His Lys Cys Pro Val Pro Glu Leu Leu
225                 230                 235                 240

Gly Gly Pro Ser Val Phe Leu Phe Pro Pro Lys Pro Lys Asp Ile Leu
            245                 250                 255

Leu Leu Ser Gln Asn Ala Lys Val Thr Cys Val Val Val Asp Val Ser
            260                 265                 270

Glu Glu Glu Pro Asp Val Gln Phe Ser Trp Phe Val Asn Asn Val Glu
            275                 280                 285

Val His Thr Ala Gln Thr Gln Pro Arg Glu Glu Gln Tyr Asn Ser Thr
        290                 295                 300

Phe Arg Val Val Ser Ala Leu Pro Leu Gln His Gln Asp Trp Met Ser
305                 310                 315                 320

Gly Lys Glu Phe Lys Cys Lys Val Asn Asn Lys Ala Leu Pro Ser Pro
                325                 330                 335

Ile Glu Lys Thr Leu Ser Lys Pro Lys Gly Leu Val Arg Lys Pro Gln
                340                 345                 350

Val Tyr Val Met Gly Pro Pro Thr Glu Gln Leu Thr Glu Gln Thr Val
            355                 360                 365

Ser Leu Thr Cys Leu Thr Ser Gly Phe Leu Pro Asn Asp Ile Gly Val
        370                 375                 380

Glu Trp Thr Ser Asn Gly His Ile Glu Lys Asn Tyr Lys Asn Thr Glu
385                 390                 395                 400

Pro Val Met Asp Ser Asp Gly Ser Phe Phe Met Tyr Ser Lys Leu Asn
                405                 410                 415

Val Glu Arg Ser Arg Trp Asp Ser Arg Ala Pro Phe Val Cys Ser Val
            420                 425                 430

Val His Glu Gly Leu His Asn His His Val Glu Lys Ser Leu Ser Arg
            435                 440                 445

Pro Pro Gly
    450
```

```
<210> SEQ ID NO 34
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asn Ile Val Met Thr Gln Ser Pro Lys Ser Met Ser Leu Ser Val Gly
1                   5                   10                  15

Asp Arg Val Thr Met Asn Cys Lys Ala Ser Gln Asn Val Gly Asn Asn
                20                  25                  30

Leu Ala Trp Tyr Gln Gln Lys Pro Gly Gln Ser Pro Lys Leu Leu Leu
```

-continued

```
                35                  40                  45

Tyr Tyr Thr Ser Asn Arg Phe Thr Gly Val Pro Asp Arg Phe Thr Gly
    50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Trp
                85                  90                  95

Thr Phe Gly Gly Gly Thr Lys Leu Glu Leu Lys Arg Ala Asp Ala Ala
                100                 105                 110

Pro Thr Val Ser Ile Phe Pro Pro Ser Thr Glu Gln Leu Ala Thr Gly
                115                 120                 125

Gly Ala Ser Val Val Cys Leu Met Asn Asn Phe Tyr Pro Arg Asp Ile
    130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Thr Lys Ala Asp Tyr Glu Ser His Asn Leu Tyr
                180                 185                 190

Thr Cys Glu Val Val His Lys Thr Ser Ser Ser Pro Val Val Lys Ser
                195                 200                 205

Phe Asn Arg Asn Glu Cys
    210

<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
                20                  25                  30

Tyr Met Ala Trp Val Arg Gln Ala Pro Thr Lys Gly Leu Glu Trp Val
            35                  40                  45

Ala Ser Leu Thr Asn Ser Gly Gly Ser Thr Tyr Tyr Arg Asp Ser Val
    50                  55                  60

Lys Gly Arg Phe Thr Leu Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Arg Glu Trp Ala Gly Ser Gly Tyr Phe Asp Tyr Trp Gly Gln Gly
                100                 105                 110

Val Met Val Thr Val Ser Ser
        115

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 36

Asn Ile Val Met Thr Gln Ser Pro Lys Ser Met Ser Leu Ser Val Gly
1               5                   10                  15

Asp Arg Val Thr Met Asn Cys Lys Ala Ser Gln Asn Val Gly Asn Asn
            20                  25                  30

Leu Ala Trp Tyr Gln Gln Lys Pro Gly Gln Ser Pro Lys Leu Leu Leu
            35                  40                  45

Tyr Tyr Thr Ser Asn Arg Phe Thr Gly Val Pro Asp Arg Phe Thr Gly
    50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Trp
                85                  90                  95

Thr Phe Gly Gly Gly Thr Lys Leu Glu Leu Lys
            100                 105

<210> SEQ ID NO 37
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
            35                  40                  45

Ala Ser Leu Thr Asn Ser Gly Gly Ser Thr Tyr Tyr Arg Asp Ser Val
    50                  55                  60

Lys Gly Arg Phe Thr Leu Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Arg Glu Trp Ala Gly Ser Gly Tyr Phe Asp Tyr Trp Gly Gln Gly
            100                 105                 110

Val Met Val Thr Val Ser Ser Ala Lys Thr Thr Ala Pro Ser Val Tyr
            115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240
```

```
Ser Val Phe Ile Phe Pro Pro Lys Ile Lys Asp Val Leu Met Ile Ser
            245             250             255

Leu Ser Pro Ile Val Thr Cys Val Val Val Asp Val Ser Glu Asp Asp
            260             265             270

Pro Asp Val Gln Ile Ser Trp Phe Val Asn Asn Val Glu Val His Thr
            275             280             285

Ala Gln Thr Gln Thr His Arg Glu Asp Tyr Asn Ser Thr Leu Arg Val
    290             295             300

Val Ser Ala Leu Pro Ile Gln His Gln Asp Trp Met Ser Gly Lys Glu
305             310             315             320

Phe Lys Cys Lys Val Asn Asn Lys Asp Leu Pro Ala Pro Ile Glu Arg
            325             330             335

Thr Ile Ser Lys Pro Lys Gly Ser Val Arg Ala Pro Gln Val Tyr Val
            340             345             350

Leu Pro Pro Pro Glu Glu Glu Met Thr Lys Lys Gln Val Thr Leu Thr
            355             360             365

Cys Met Val Thr Asp Phe Met Pro Glu Asp Ile Tyr Val Glu Trp Thr
    370             375             380

Asn Asn Gly Lys Thr Glu Leu Asn Tyr Lys Asn Thr Glu Pro Val Leu
385             390             395             400

Asp Ser Asp Gly Ser Tyr Phe Met Tyr Ser Lys Leu Arg Val Glu Lys
            405             410             415

Lys Asn Trp Val Glu Arg Asn Ser Tyr Ser Cys Ser Val Val His Glu
            420             425             430

Gly Leu His Asn His His Thr Thr Lys Ser Phe Ser Arg Thr Pro Gly
            435             440             445

Lys
```

```
<210> SEQ ID NO 38
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asn Ile Val Met Thr Gln Ser Pro Lys Ser Met Ser Leu Ser Val Gly
1               5               10              15

Asp Arg Val Thr Met Asn Cys Lys Ala Ser Gln Asn Val Gly Asn Asn
            20              25              30

Leu Ala Trp Tyr Gln Gln Lys Pro Gly Gln Ser Pro Lys Leu Leu Leu
            35              40              45

Tyr Tyr Thr Ser Asn Arg Phe Thr Gly Val Pro Asp Arg Phe Thr Gly
    50              55              60

Gly Gly Tyr Gly Thr Asp Phe Thr Leu Thr Ile Asn Ser Val Gln Ala
65              70              75              80

Glu Asp Ala Ala Phe Tyr Tyr Cys Gln Arg Ile Tyr Asn Ser Pro Trp
            85              90              95

Thr Phe Gly Gly Gly Thr Lys Leu Glu Leu Lys Arg Ala Asp Ala Ala
            100             105             110

Pro Thr Val Ser Ile Phe Pro Pro Ser Ser Glu Gln Leu Thr Ser Gly
            115             120             125

Gly Ala Ser Val Val Cys Phe Leu Asn Asn Phe Tyr Pro Lys Asp Ile
    130             135             140
```

```
Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

```
<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Phe Thr Phe Ser Asn Tyr Tyr Met Ala
1               5                   10
```

```
<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Leu Thr Asn Ser Gly Gly Ser Thr Tyr
1               5                   10
```

```
<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Trp Ala Gly Ser Gly Tyr Phe Asp Tyr
1               5                   10
```

```
<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Ala Ser Gln Asn Val Gly Asn Asn Leu Ala
1               5                   10
```

```
<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 43

Tyr Thr Ser Asn Arg Phe Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Arg Ile Tyr Asn Ser Pro Trp Thr
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Phe Thr Phe Ser Asn Tyr
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asn Tyr Tyr Met Ala
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Asn Tyr Tyr Met Ala
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Phe Thr Phe Ser Asn Tyr Tyr
1               5

<210> SEQ ID NO 49
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Asn Ser Gly Gly Ser
1               5

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Leu Thr Asn Ser Gly Gly Ser Thr Tyr Tyr Ala Asp Ser Val Lys
1               5                   10                  15

Gly

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Val Ser Ser Leu Thr Asn Ser Gly Gly Ser Thr Tyr
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Thr Asn Ser Gly Gly Ser Thr
1               5

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Arg Glu Trp Ala Gly Ser Gly Tyr Phe Asp
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54
```

```
Thr Arg Glu Trp Ala Gly Ser Gly Tyr Phe Asp Tyr
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Asn Asn Leu Ala Trp Tyr
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Asn Val Gly Asn Asn
1               5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Leu Ile Tyr Tyr Thr Ser Asn Arg Phe
1               5                   10

<210> SEQ ID NO 58
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Thr
1

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Arg Ile Tyr Asn Ser Pro Trp
1               5
```

METHODS OF USING ANTI-TREM2 ANTIBODIES

CROSS REFERENCE TO RELATED APPLICATIONS

This application is a continuation of International Application PCT/US2019/065743, filed Dec. 11, 2019, which is a continuation-in-part of International Application PCT/US2018/065026, filed Dec. 11, 2018, and which also claims the benefit of U.S. Provisional Application 62/889,990, filed Aug. 21, 2019, each of which are hereby incorporated by reference in their entirety for all purposes.

SEQUENCE LISTING

The instant application contains a Sequence Listing which has been submitted via EFS-Web and is hereby incorporated by reference in its entirety. Said ASCII copy, created on Jun. 10, 2021, is named PII-011WOUSC1_SL.txt, and is 65,993 bytes in size.

BACKGROUND

Immunity plays a role in preventing tumor outgrowth. A complex microenvironment can develop within the lesion, and despite the recruitment of T-cells, there is often no effective control of the developing mass. Understanding the balance between tumor elimination and tumor escape may rely on a comprehension of the differential roles myeloid cells play in the tumor microenvironment.

Myeloid populations of the tumor microenvironment prominently include monocytes and neutrophils (sometimes loosely grouped as myeloid-derived suppressor cells), macrophages, and dendritic cells. Although intra-tumoral myeloid populations, as a whole, have long been considered non-stimulatory or suppressive, it has more recently been appreciated that not all tumor-infiltrating myeloid cells are made equal.

In normal tissues, many of these myeloid cells are essential for proper functioning of both innate and adaptive immunity and notably for wound repair. However in the setting of cancer, a significant excess of macrophages and dysfunctional or skewed populations of these and other cell types are commonly described. When considered as an aggregate population defined by single markers, such as CD68 or CD163. "macrophage" infiltration is correlated with worse outcomes in subjects across multiple tumor types ((de Visser, Cancer Immunol Immunother, 2008; 57:1531-9); (Hanada et al., Int J Urol 2000; 7:263-9); (Yao et al. Clin Cancer Res, 520, 2001; 7:4021-6); (Ruffell et al., PNAS, 523 2012; 109:2796-801)). But the phenotypic and functional sub-setting of macrophages from the tumor microenvironment is complicated by the similarity of macrophages and dendritic cells, and is problematic in tumor biology. A morphologic criterion has been often applied to the issue; one approach to try to differentiate dendritic cells from macrophages was based on a more spikey or dendritic morphology for the former and more veiled or bulbous morphology for the latter (Bell et al., J Exp Med 555, 1999; 190:1417-26). Other groups are trying to differentiate on the basis of genetic and cell-surface markers.

There is diversity in the antigen-presenting compartment within tumors, and T-cells can differentiate features of antigen-presenting cells (APC). Because T cells are a major driver of tumor immunity, understanding the exact features of their cognate APCs will be important. Myeloid cells are prominent among cells capable of presenting tumor-derived antigens to T-cells and thereby maintaining the latter in an activated state. Antigen presentation occurs within the tumor itself and likely influences the functions of tumor cytotoxic T-lymphocytes (CTLs). T-cell activation by antigen presenting cells (APC) is an important component in antigen-specific immune responses and tumor cell killing. As these myeloid populations represent major T-cell-interacting partners and antigen-presenting cells for incoming tumor-reactive cytotoxic T lymphocytes, understanding their distinctions may guide therapeutic avenues.

Related patent applications include: PCT/US2015/052682, filed Sep. 28, 2015; PCT/US2016/054104, filed Sep. 28, 2016, and PCT/US2018/065026, filed Dec. 11, 2018; each of which is herein incorporated by reference, in their entirety, for all purposes.

All patents, patent applications, publications, documents, and articles cited herein are incorporated herein by reference in their entireties.

SUMMARY

In one aspect, provided herein are methods of treating ovarian cancer in a subject in need thereof, comprising administering to the subject an isolated humanized antibody that binds to human TREM2 (SEQ ID NO:15) and competes for binding to mouse TREM2 (SEQ ID NO:17) with the 37017 antibody (SEQ ID NOs: 31 and 32). In an aspect, provided herein are methods of treating a solid cancer in a subject in need thereof, comprising administering to the subject an isolated humanized antibody that binds to human TREM2 (SEQ ID NO:15) and competes for binding to mouse TREM2 (SEQ ID NO:17) with the 37017 antibody (SEQ ID NOs: 31 and 32).

In some embodiments, the antibody comprises: a CDR-H1 comprising the sequence set forth in SEQ ID NO: 9 or 39, a CDR-H2 comprising the sequence set forth in SEQ ID NO:10, a CDR-H3 comprising the sequence set forth in SEQ ID NO:11 or 41, a CDR-L1 comprising the sequence set forth in SEQ ID NO: 12 or 42, a CDR-L2 comprising the sequence set forth in SEQ ID NO: 13 or 43, and a CDR-L3 comprising the sequence set forth in SEQ ID NO: 14 or 44. In some embodiments, the antibody is afucosylated and comprises the VH sequence shown in SEQ ID NO: 1; the VL sequence shown in SEQ ID NO: 2; and an active human IgG1 Fc region. In some embodiments, the antibody comprises the sequences set forth in at least one of: SEQ ID NO: 9 or 39. SEQ ID NO:10 or 40, SEQ ID NO:11 or 41. SEQ ID NO: 12 or 42, SEQ ID NO: 13 or 43, and SEQ ID NO: 14 or 44. In some embodiments, the antibody comprises the sequences set forth in each of: SEQ ID NO: 9 or 39, SEQ ID NO:10 or 40, SEQ ID NO:11 or 41. SEQ ID NO: 12 or 42. SEQ ID NO: 13 or 43, and SEQ ID NO: 14 or 44. In some embodiments, the antibody comprises the sequence shown in SEQ ID NO: 1. In some embodiments, the antibody comprises the sequence shown in SEQ ID NO: 2. In some embodiments, the antibody comprises the sequence shown in SEQ ID NO: 1 and the sequence shown in SEQ ID NO:2.

In some embodiments, the antibody comprises a VH sequence comprising an A to T substitution at position 97 of the sequence shown in SEQ ID NO: 7; and a K to R substitution at position 98 of the sequence shown in SEQ ID NO: 7. In some embodiments, the antibody comprises the VH sequence shown in SEQ ID NO: 1, 3, or 5. In some embodiments, the antibody comprises the VH sequence shown in SEQ ID NO: 1, 3, or 5 and the VL sequence shown in SEQ ID NO: 2, 4, or 6. In some embodiments, the antibody comprises the VH sequence shown in SEQ ID NO: 1.

In some embodiments, the antibody comprises the VH sequence shown in SEQ ID NO: 1 and the VL sequence shown in SEQ ID NO: 2. In some embodiments, the antibody is the 37012 antibody. In some embodiments, the antibody comprises the heavy chain sequence shown in SEQ ID NO: 25 and the light chain sequence shown in SEQ ID NO: 26.

In another aspect, provided herein are methods of treating a solid cancer in a subject in need thereof, comprising administering to the subject an isolated antibody that binds to human TREM2 (SEQ ID NO:15), wherein the antibody i) competes for binding to mouse TREM2 (SEQ ID NO:17) with the 37017 antibody (SEQ ID NOs: 31 and 32); and ii) comprises a human Fc region.

In another aspect, provided herein are methods of treating a solid cancer in a subject in need thereof, comprising administering to the subject an isolated antibody that binds to human TREM2 (SEQ ID NO:15), wherein the antibody i) competes for binding to mouse TREM2 (SEQ ID NO:17) with the 37017 antibody (SEQ ID NOs: 31 and 32); and ii) comprises a human Fc region. In another aspect, provided herein are methods of treating ovarian cancer in a subject in need thereof, comprising administering to the subject an isolated antibody that binds to human TREM2 (SEQ ID NO:15), wherein the antibody i) competes for binding to mouse TREM2 (SEQ ID NO:17) with the 37017 antibody (SEQ ID NOs: 31 and 32); and i) comprises a human Fc region.

In another aspect, provided herein are methods of treating a solid cancer in a subject in need thereof, comprising administering to the subject an isolated humanized antibody wherein the antibody comprises: a CDR-H1 comprising the sequence set forth in SEQ ID NO: 9 or 39, a CDR-H2 comprising the sequence set forth in SEQ ID NO:10 or 40, a CDR-H3 comprising the sequence set forth in SEQ ID NO:11 or 41, a CDR-L1 comprising the sequence set forth in SEQ ID NO: 12 or 42, a CDR-L2 comprising the sequence set forth in SEQ ID NO: 13 or 43, and a CDR-L3 comprising the sequence set forth in SEQ ID NO: 14 or 44. In another aspect, provided herein are methods of treating ovarian cancer in a subject in need thereof, comprising administering to the subject an isolated humanized antibody wherein the antibody comprises: a CDR-H1 comprising the sequence set forth in SEQ ID NO: 9 or 39, a CDR-H2 comprising the sequence set forth in SEQ ID NO:10 or 40, a CDR-H3 comprising the sequence set forth in SEQ ID NO:11 or 41, a CDR-L1 comprising the sequence set forth in SEQ ID NO: 12 or 42, a CDR-L2 comprising the sequence set forth in SEQ ID NO: 13 or 43, and a CDR-L3 comprising the sequence set forth in SEQ ID NO: 14 or 44.

In some embodiments, the antibody comprises a VH sequence comprising an A to T substitution at position 97 of the sequence shown in SEQ ID NO:7; and a K to R substitution at position 98 of the sequence shown in SEQ ID NO:7. In some embodiments, the antibody comprises the VH sequence shown in SEQ ID NO: 1, 3, or 5. In some embodiments, the antibody comprises the VH sequence shown in SEQ ID NO: 1, 3, or 5 and the VL sequence shown in SEQ ID NO: 2, 4, or 6. In some embodiments, the antibody comprises the VH sequence shown in SEQ ID NO: 1. The method of claim 16, wherein the antibody comprises the VH sequence shown in SEQ ID NO: 1 and the VL sequence shown in SEQ ID NO: 2. In some embodiments, the antibody is the 37012 antibody. In some embodiments, the antibody comprises the heavy chain sequence shown in SEQ ID NO: 25 and the light chain sequence shown in SEQ ID NO: 26.

In some embodiments, the antibody binds to human TREM2 with a $K_D$ of less than or equal to about 1, 2, 3, 4, or $5\times10^{-9}$ M, as measured by surface plasmon resonance (SPR) assay.

In some embodiments, the antibody is capable of specifically killing, depleting, or disabling TREM2+ myeloid cells; optionally non-stimulatory myeloid cells; optionally intra-tumoral myeloid cells.

In some embodiments, the antibody has antibody-dependent cell-mediated cytotoxicity (ADCC) activity. In some embodiments, the antibody has antibody-mediated cellular phagocytosis (ADCP) activity. In some embodiments, the antibody has complement-dependent cytotoxicity (CDC) activity.

In some embodiments, the antibody is at least one of: a monoclonal antibody, a neutral antibody, an antagonistic antibody, an agonist antibody, a polyclonal antibody, an IgG1 antibody, an IgG3 antibody, an afucosylated antibody, a bispecific antibody, a human antibody, a chimeric antibody, a full-length antibody, and an antigen binding fragment thereof. In some embodiments, the antibody is a monoclonal antibody. In some embodiments, the antibody is multispecific. In some embodiments, the antibody is afucosylated.

In some embodiments, the antibody is an antigen-binding fragment thereof, a Fab, Fab', F(ab')2, Fv, scFv, (scFv)2, single chain antibody molecule, dual variable domain antibody, single variable domain antibody, linear antibody, or V domain antibody.

In some embodiments, the antibody comprises a scaffold, optionally wherein the scaffold is Fc, optionally human Fc. In some embodiments, the antibody comprises a heavy chain constant region of a class selected from IgG, IgA, IgD, IgE, and IgM. In some embodiments, the antibody comprises a heavy chain constant region of the class IgG and a subclass selected from IgG1, IgG2, IgG3, and IgG4. In some embodiments, the antibody comprises a heavy chain constant region of IgG1.

In some embodiments, Fc comprises one or more modifications, wherein the one or more modifications result in increased half-life, increased ADCC activity, increased ADCP activity, or increased CDC activity compared with the Fc without the one or more modifications. In some embodiments, the Fc binds an Fcγ Receptor selected from the group consisting of: FcγRI, FcγRIIa FcγRIIb, FcγRIIc, FcγRIIIa, and Fc-γRIIIb.

In some embodiments, the antibody binds to the extracellular domain of TREM2 on TREM2+ myeloid cells, optionally wherein the myeloid cells are intratumoral.

In some embodiments, the antibody binds to the extracellular domain of TREM2 on myeloid cells, wherein the myeloid cells are non-stimulatory myeloid cells that are CD45+, HLA-DR+, CD11c+, CD14+, and BDCA3−, wherein the antibody kills, disables, or depletes the non-stimulatory myeloid cells via ADCC, CDC, and/or ADCP to a level that is less than the level of non-stimulatory myeloid cells present in the cancer prior to the contacting of the non-stimulatory myeloid cells with the antibody, wherein the non-stimulatory myeloid cells are present in a population of immune cells comprising stimulatory myeloid cells that are CD45+, HLA-DR+, CD14−, CD11c+, BDCA1−, and BDCA3+ and the non-stimulatory myeloid cells, and wherein the killing, disabling, or depleting of the non-stimulatory myeloid cells treats the cancer.

In some embodiments, the contacting enhances an immune response in the subject. In some embodiments, the enhanced immune response is an adaptive immune response. In some embodiments, the enhanced immune response is an innate immune response. In some embodiments, the subject has previously received, is concurrently receiving, or will subsequently receive an immunotherapy.

In some embodiments, immunotherapy is at least one of: a checkpoint inhibitor; a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; and an epigenetic modulator. In some embodiments, the immunotherapy is selected from the group consisting of: an anti-PD1 antibody, an anti-PDL1 antibody; or an anti-CTLA4 antibody.

In another aspect, provided herein are methods of treating gastric cancer in a subject in need thereof, comprising administering to the subject an isolated humanized antibody that binds to human TREM2 (SEQ ID NO:15) and competes for binding to mouse TREM2 (SEQ ID NO:17) with the 37017 antibody (SEQ ID NOs: 31 and 32).

In some embodiments, the antibody comprises: a CDR-H1 comprising the sequence set forth in SEQ ID NO: 9 or 39, a CDR-H2 comprising the sequence set forth in SEQ ID NO:10 or 40, a CDR-H3 comprising the sequence set forth in SEQ ID NO:11 or 41, a CDR-L1 comprising the sequence set forth in SEQ ID NO: 12 or 42, a CDR-L2 comprising the sequence set forth in SEQ ID NO: 13 or 43, and a CDR-L3 comprising the sequence set forth in SEQ ID NO: 14 or 44. In some embodiments, the antibody is afucosylated and comprises the VH sequence shown in SEQ ID NO: 1; the VL sequence shown in SEQ ID NO: 2; and an active human IgG1 Fc region.

In some embodiments, the antibody comprises a VH sequence comprising an A to T substitution at position 97 of the sequence shown in SEQ ID NO: 7; and a K to R substitution at position 98 of the sequence shown in SEQ ID NO: 7. In some embodiments, the antibody comprises the VH sequence shown in SEQ ID NO: 1, 3, or 5. In some embodiments, the antibody comprises the VH sequence shown in SEQ ID NO: 1, 3, or 5 and the VL sequence shown in SEQ ID NO: 2, 4, or 6. In some embodiments, the antibody comprises the VH sequence shown in SEQ ID NO: 1.

In some embodiments, the antibody comprises the VH sequence shown in SEQ ID NO: 1 and the VL sequence shown in SEQ ID NO: 2. In some embodiments, the antibody is the 37012 antibody. In some embodiments, the antibody comprises the heavy chain sequence shown in SEQ ID NO: 25 and the light chain sequence shown in SEQ ID NO: 26.

In another aspect, provided herein are methods of treating gastric cancer in a subject in need thereof, comprising administering to the subject an isolated antibody that binds to human TREM2 (SEQ ID NO:15), wherein the antibody 0 competes for binding to mouse TREM2 (SEQ ID NO:17) with the 37017 antibody (SEQ ID NOs: 31 and 32); and h) comprises a human Fc region.

In another aspect, provided herein are methods of treating gastric cancer in a subject in need thereof, comprising administering to the subject an isolated humanized antibody wherein the antibody comprises: a CDR-H1 comprising the sequence set forth in SEQ ID NO: 9 or 39, a CDR-H2 comprising the sequence set forth in SEQ ID NO:10 or 40, a CDR-H3 comprising the sequence set forth in SEQ ID NO:11 or 41, a CDR-L1 comprising the sequence set forth in SEQ ID NO: 12 or 42, a CDR-L2 comprising the sequence set forth in SEQ ID NO: 13 or 43, and a CDR-L3 comprising the sequence set forth in SEQ ID NO: 14 or 44.

In some embodiments, the antibody comprises a VH sequence comprising an A to T substitution at position 97 of the sequence shown in SEQ ID NO:7; and a K to R substitution at position 98 of the sequence shown in SEQ ID NO:7. In some embodiments, the antibody comprises the VH sequence shown in SEQ ID NO: 1, 3, or 5. In some embodiments, the antibody comprises the VH sequence shown in SEQ ID NO: 1, 3, or 5 and the VL sequence shown in SEQ ID NO: 2, 4, or 6. In some embodiments, the antibody comprises the VH sequence shown in SEQ ID NO: 1. The method of claim 16, wherein the antibody comprises the VH sequence shown in SEQ ID NO: 1 and the VL sequence shown in SEQ ID NO: 2. In some embodiments, the antibody is the 37012 antibody. In some embodiments, the antibody comprises the heavy chain sequence shown in SEQ ID NO: 25 and the light chain sequence shown in SEQ ID NO: 26.

In some embodiments, the antibody binds to human TREM2 with a $K_D$ of less than or equal to about 1, 2, 3, 4, or $5 \times 10^{-9}$M, as measured by surface plasmon resonance (SPR) assay.

In some embodiments, the antibody is capable of specifically killing, depleting, or disabling TREM2+ myeloid cells; optionally non-stimulatory myeloid cells; optionally intratumoral myeloid cells.

In some embodiments, the antibody has antibody-dependent cell-mediated cytotoxicity (ADCC) activity. In some embodiments, the antibody has antibody-mediated cellular phagocytosis (ADCP) activity. In some embodiments, the antibody has complement-dependent cytotoxicity (CDC) activity.

In some embodiments, the antibody is at least one of: a monoclonal antibody, a neutral antibody, an antagonistic antibody, an agonist antibody, a poly clonal antibody, an IgG1 antibody, an IgG3 antibody, an afucosylated antibody, a bispecific antibody, a human antibody, a chimeric antibody, a full-length antibody, and an antigen binding fragment thereof. In some embodiments, the antibody is a monoclonal antibody. In some embodiments, the antibody is multispecific. In some embodiments, the antibody is afucosylated.

In some embodiments, the antibody is an antigen-binding fragment thereof, a Fab, Fab', F(ab')2, Fv, scFv, (scFv)2, single chain antibody molecule, dual variable domain antibody, single variable domain antibody, linear antibody, or V domain antibody.

In some embodiments, the antibody comprises a scaffold, optionally wherein the scaffold is Fc, optionally human Fc. In some embodiments, the antibody comprises a heavy chain constant region of a class selected from IgG, IgA, IgD, IgE, and IgM. In some embodiments, the antibody comprises a heavy chain constant region of the class IgG and a subclass selected from IgG1, IgG2, IgG3, and IgG4. In some embodiments, the antibody comprises a heavy chain constant region of IgG1.

In some embodiments, Fc comprises one or more modifications, wherein the one or more modifications result in increased half-life, increased ADCC activity, increased ADCP activity, or increased CDC activity compared with the Fc without the one or more modifications. In some embodiments, the Fc binds an Fcγ Receptor selected from the group consisting of: FcγRI, FcγRIIa, FcγRIIb, FcγRIIc, FcγRIIIa, and FcγRIIIb.

In some embodiments, the antibody binds to the extracellular domain of TREM2 on TREM2+ myeloid cells, optionally wherein the myeloid cells are intratumoral.

In some embodiments, the antibody binds to the extracellular domain of TREM2 on myeloid cells, wherein the myeloid cells are non-stimulatory myeloid cells that are CD45+, HLA-DR+, CD11c+. CD14+, and BDCA3−, wherein the antibody kills, disables, or depletes the non-stimulatory myeloid cells via ADCC, CDC, and/or ADCP to a level that is less than the level of non-stimulatory myeloid cells present in the cancer prior to the contacting of the non-stimulatory myeloid cells with the antibody, wherein the non-stimulatory myeloid cells are present in a population of immune cells comprising stimulatory myeloid cells that are CD45+, HLA-DR+, CD14−, CD11c+, BDCA1−, and BDCA3+ and the non-stimulatory myeloid cells, and wherein the killing, disabling, or depleting of the non-stimulatory myeloid cells treats the cancer.

In some embodiments, the contacting enhances an immune response in the subject. In some embodiments, the enhanced immune response is an adaptive immune response. In some embodiments, the enhanced immune response is an innate immune response. In some embodiments, the subject has previously received, is concurrently receiving, or will subsequently receive an immunotherapy.

In some embodiments, immunotherapy is at least one of: a checkpoint inhibitor; a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; and an epigenetic modulator. In some embodiments, the immunotherapy is selected from the group consisting of: an anti-PD1 antibody, an anti-PDL1 antibody; or an anti-CTLA4 antibody.

In another aspect, provided herein are methods of enhancing an immune response comprising administering to a subject an isolated humanized antibody that binds to human TREM2 (SEQ ID NO:15) and competes for binding to mouse TREM2 (SEQ ID NO:17) with the 37017 antibody (SEQ ID NOs: 31 and 32). In some aspects the subject has a solid tumor. In some aspects, the solid tumor is an ovarian tumor. In some aspects, the solid tumor is a gastric tumor. In some aspects the immune response includes ADCC, CDC, and/or ADCP.

In some embodiments, the antibody comprises: a CDR-H1 comprising the sequence set forth in SEQ ID NO: 9 or 39, a CDR-H2 comprising the sequence set forth in SEQ ID NO:10 or 40, a CDR-H3 comprising the sequence set forth in SEQ ID NO:11 or 41, a CDR-L1 comprising the sequence set forth in SEQ ID NO: 12 or 42, a CDR-L2 comprising the sequence set forth in SEQ ID NO: 13 or 43, and a CDR-L3 comprising the sequence set forth in SEQ ID NO: 14 or 44.

In some embodiments, the antibody is afucosylated and comprises the VH sequence shown in SEQ ID NO: 1; the VL sequence shown in SEQ ID NO: 2; and an active human IgG1 Fc region. In some embodiments, the antibody comprises a VH sequence comprising an A to T substitution at position 97 of the sequence shown in SEQ ID NO:7; and a K to R substitution at position 98 of the sequence shown in SEQ ID NO:7.

In some embodiments, the antibody comprises the VH sequence shown in SEQ ID NO: 1, 3, or 5. In some embodiments, the antibody comprises the VH sequence shown in SEQ ID NO: 1, 3, or 5 and the VL sequence shown in SEQ ID NO: 2, 4, or 6. In some embodiments, the antibody comprises the VH sequence shown in SEQ ID NO: 1. In some embodiments, the antibody comprises the VH sequence shown in SEQ ID NO: 1 and the VL sequence shown in SEQ ID NO: 2. In some embodiments, the antibody is the 37012 antibody. In some embodiments, the antibody comprises the heavy chain sequence shown in SEQ ID NO: 25 and the light chain sequence shown in SEQ ID NO: 26.

In another aspect, provided herein are methods of enhancing an immune response comprising administering to a subject an isolated antibody that binds to human TREM2 (SEQ ID NO:15), wherein the antibody i) competes for binding to mouse TREM2 (SEQ ID NO:17) with the 37017 antibody (SEQ ID NOs: 31 and 32); and i) comprises a human Fc region. In some aspects the subject has a solid tumor. In some aspects, the solid tumor is an ovarian tumor. In some aspects, the solid tumor is a gastric tumor. In some aspects the immune response includes ADCC, CDC, and/or ADCP.

In another aspect, provided herein are methods of enhancing an immune response comprising administering to a subject an isolated humanized antibody wherein the antibody comprises: a CDR-H1 comprising the sequence set forth in SEQ ID NO: 9 or 39, a CDR-H2 comprising the sequence set forth in SEQ ID NO:10 or 40, a CDR-H3 comprising the sequence set forth in SEQ ID NO:11 or 41, a CDR-L comprising the sequence set forth in SEQ ID NO: 12 or 42, a CDR-L2 comprising the sequence set forth in SEQ ID NO: 13 or 43, and a CDR-L3 comprising the sequence set forth in SEQ ID NO: 14 or 44. In some aspects the subject has a solid tumor. In some aspects, the solid tumor is an ovarian tumor. In some aspects, the solid tumor is a gastric tumor. In some aspects the immune response includes ADCC, CDC, and/or ADCP.

In some embodiments, the antibody comprises a VH sequence comprising an A to T substitution at position 97 of the sequence shown in SEQ ID NO:7; and a K to R substitution at position 98 of the sequence shown in SEQ ID NO:7.

In some embodiments, the antibody comprises the VH sequence shown in SEQ ID NO: 1, 3, or 5. In some embodiments, the antibody comprises the VH sequence shown in SEQ ID NO: 1, 3, or 5 and the VL sequence shown in SEQ ID NO: 2, 4, or 6. In some embodiments, the antibody comprises the VH sequence shown in SEQ ID NO: 1. In some embodiments, the antibody comprises the VH sequence shown in SEQ ID NO: 1 and the VL sequence shown in SEQ ID NO: 2.

In some embodiments, the antibody is the 37012 antibody. In some embodiments, the antibody comprises the heavy chain sequence shown in SEQ ID NO: 25 and the light chain sequence shown in SEQ ID NO: 26. In some embodiments, the antibody binds to human TREM2 with a $K_D$ of less than or equal to about 1, 2, 3, 4, or $5 \times 10^{-9}$ M, as measured by surface plasmon resonance (SPR) assay.

In some embodiments, the subject has ovarian cancer. In some embodiments, the subject has gastric cancer.

In some embodiments, the subject has previously received, is concurrently receiving, or will subsequently receive an immunotherapy. In some embodiments, the immunotherapy is at least one of: a checkpoint inhibitor; a checkpoint inhibitor of T cells; anti-PD1 antibody; anti- PDL1 antibody; anti-CTLA4 antibody; adoptive T cell therapy; CAR-T cell therapy; a dendritic cell vaccine; a monocyte vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; and an epigenetic modulator. In some embodiments, the immunotherapy is selected from the group consisting of: an anti-PD1 antibody, an anti-PDL1 antibody; or an anti-CTLA4 antibody.

In some embodiments, the antibody is capable of specifically killing, depleting, or disabling TREM2+ myeloid cells; optionally non-stimulatory myeloid cells; optionally intratumoral myeloid cells.

In some embodiments, the antibody has antibody-dependent cell-mediated cytotoxicity (ADCC) activity. In some embodiments, the antibody has antibody-mediated cellular phagocytosis (ADCP) activity. In some embodiments, the antibody has complement-dependent cytotoxicity (CDC) activity.

In some embodiments, the antibody has receptor-ligand blocking, agonist, or antagonist activity. In some embodiments, the antibody has agonist activity.

In some embodiments, the antibody induces increased expression of at least one cytokine or chemokine in a cell as compared to an isotype control antibody. In some embodiments, the at least one cytokine or chemokine is selected from the group consisting of: IFN-$\gamma$, TNF-$\alpha$, CXCL1, or CXCL10. In some embodiments, the cytokine or chemokine is CXCL10.

In some embodiments, the enhanced immune response is an adaptive immune response. In some embodiments, the enhanced immune response is an innate immune response. In some embodiments, the antibody induces a memory immune response.

In some embodiments, the cell is a TREM2+ cell. In some embodiments, the TREM2+ cell is selected from the group consisting of: dendritic cells, tumor associated macrophages (TAMs) and neutrophils.

In some embodiments, the subject is human.

BRIEF DESCRIPTION OF THE DRAWINGS

FIG. 9F shows statistical analyses of the group average tumor volumes on day 32 after implant for each treatment group.

FIG. 12A shows TREM2 expression in ovarian cancers. FIG. 12B shows TREM2 expression in ovarian cancers. FIG. 12C shows TREM2 expression in gastric cancers. FIG. 12D shows TREM2 expression liver cancers. FIG. 12E shows TREM2 expression in prostate cancers. FIG. 12F shows TREM2 expression in pancreatic cancers. FIG. 12G shows TREM2 expression in bladder cancers. FIG. 12H shows TREM2 expression in lung cancers. FIG. 12M shows TREM2 expression in melanoma. FIG. 12N shows TREM2 expression in endometrial cancers. FIG. 12O shows TREM2 expression in lung adenocarcinomas.

FIG. 13A shows anti-TREM2 antibody treatment resulted in decreased tumor size in vivo the EMT6 model. FIG. 13B shows anti-TREM2 antibody therapy decreased the number of MHCII$^{low}$ TAMs and increased the number of MHCII$^{high}$ TAMs as compared to isotype antibody alone. FIG. 13C shows anti-TREM2 antibody therapy increased the number of CD8+ T cells and NKp46+ NK cells as compared to isotype antibody alone.

FIG. 17A shows TREM2 expression levels in ovarian cancer inversely correlate with patient survival possibility. FIG. 17B shows TREM2 expression levels in ovarian cancer inversely correlate with patient survival possibility. FIG. 17C shows TREM2 expression levels in ovarian cancer inversely correlate with patient survival possibility.

DETAILED DESCRIPTION

Definitions

Figures 1A, 1B, 1C:
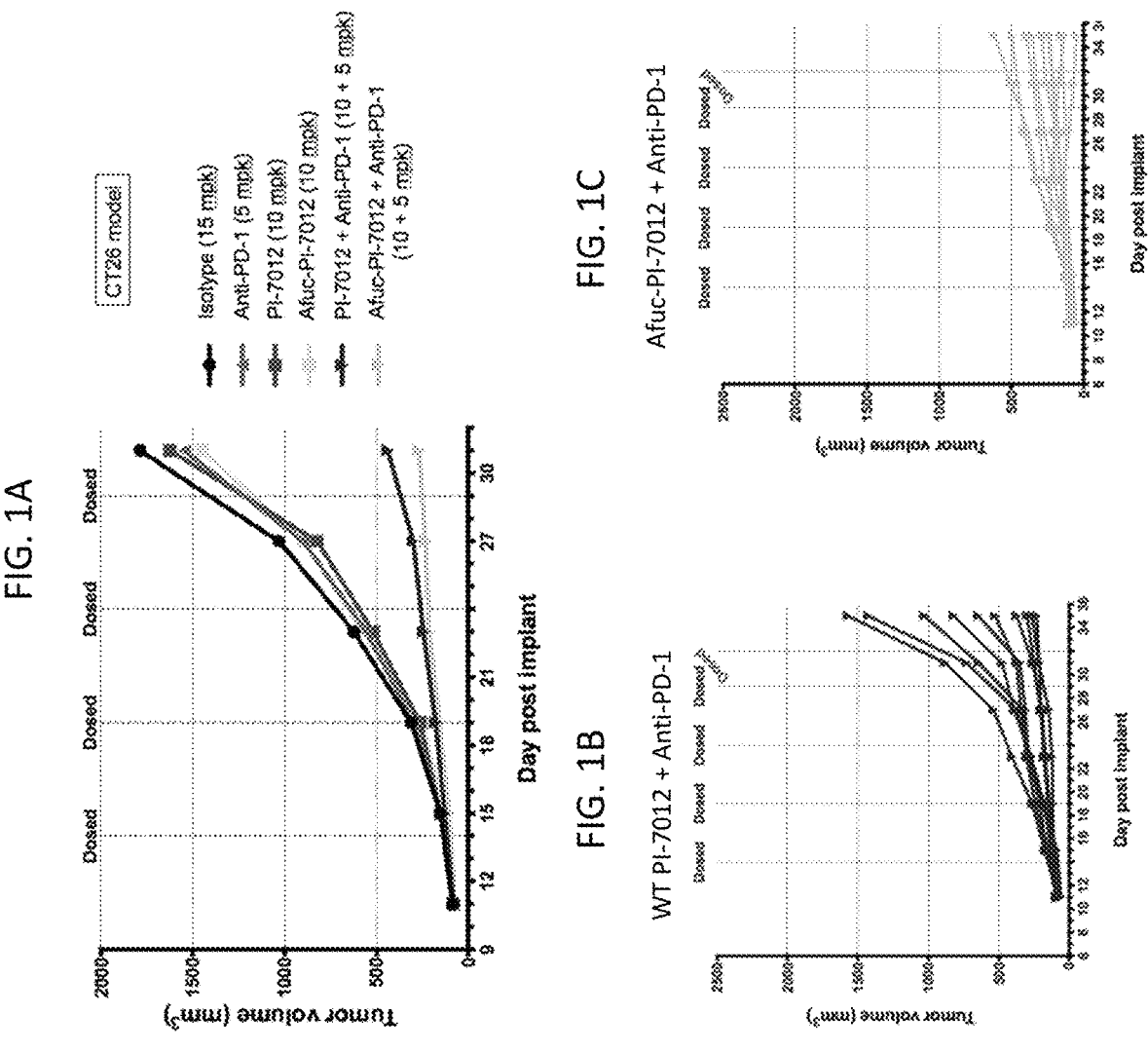
FIG. 1A shows anti-TREM2 PI-7012-mediated anti-tumor activity in combination with anti-PD-1 in the CT-26 syngeneic mouse tumor model. Afucosylation of PI-7012 improves anti-tumor activity in combination with anti-PD-1. Shown are the average tumor volumes (10 mice/group).
FIG. 1B shows individual tumor volumes for PI-7012.
FIG. 1C shows individual tumor volumes for afucosylated-PI-7012 (afuc-PI-7012).

For purposes of interpreting this specification, the following definitions will apply and whenever appropriate, terms used in the singular will also include the plural and vice versa. In the event that any definition set forth below conflicts with any document incorporated herein by reference, the definition set forth shall control.

It is understood that aspects and embodiments of the invention described herein include "comprising," "consisting," and "consisting essentially of" aspects and embodiments.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as "consisting essentially of" a component, the composition may additionally contain any amount of pharmaceutically acceptable carriers, vehicles, or diluents and other such components which do not substantially affect the condition being treated.

The term "optionally" is meant, when used sequentially, to include from one to all of the enumerated combinations and contemplates all subcombinations.

An "effective amount" or "therapeutically effective amount" as used herein refers to an amount of therapeutic compound, such as an anti-TREM2 antigen binding agent or anti-TREM2 antibody, administered to an individual, either as a single dose or as part of a series of doses, which is effective to produce or contribute to a desired therapeutic effect, either alone or in combination with another therapeutic modality. Examples of a desired therapeutic effect is enhancing an immune response, slowing or delaying tumor development; stabilization of disease; amelioration of one or more symptoms. An effective amount may be given in one or more dosages.

The term "treating" as used herein, refers to retarding or reversing the progress of a condition, such as cancer. The term "treatment," as used herein, refers to the act of treating a condition, such as cancer.

An "individual" or "subject" as used herein refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human. In some embodiments, the individual is mouse.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

The term "about" as used herein refers to the usual error range for the respective value readily known to the skilled person in this technical field. An exemplary error range is plus or minus 5%. Reference to "about" a value or parameter herein includes (and describes) embodiments that are directed to that value or parameter per se.

It must be noted that, as used in the specification and the appended claims, the singular forms "a," "an" and "the" include plural referents unless the context clearly dictates otherwise.

For any of the structural and functional characteristics described herein, methods of determining these characteristics are known in the art.

Antibodies

Structure

The present application provides antibodies and compositions comprising an antibody which binds a TREM2 protein including antibodies that disable non-stimulatory myeloid cells.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies.

The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes). e.g., IgG1, $IgG_2$, IgG3, IgG4, IgA1, and $IgA_2$. The heavy chain constant domains that correspond to the different classes of immunoglobulins are called $\alpha$, $\delta$, $\epsilon$, $\gamma$, and $\mu$, respectively.

An exemplary immunoglobulin (antibody) structural unit is composed of two pairs of polypeptide chains, each pair having one "light" (about 25 kD) and one "heavy" chain (about 50-70 kD). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antibody provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

In some embodiments, the antibodies provided herein comprise a heavy chain. In one embodiment, the heavy chain is an IgA. In one embodiment, the heavy chain is an IgD. In one embodiment, the heavy chain is an IgE. In one embodiment, the heavy chain is an IgG. In one embodiment, the heavy chain is an IgM. In one embodiment, the heavy chain is an IgG1. In one embodiment, the heavy chain is an IgG2. In one embodiment, the heavy chain is an IgG3. In one embodiment, the heavy chain is an IgG4. In one embodiment, the heavy chain is an IgA1. In one embodiment, the heavy chain is an IgA2.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Pluckthun, *J. Mol. Biol.*, 2001, 309:657-70 ("AHo" numbering scheme); each of which is incorporated by reference in its entirety.

Table A provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

TABLE A

Residues in CDRs according to Kabat and Chothia numbering schemes.

| CDR | Kabat | Chothia |
|-----|-------|---------|
| L1 | L24-L34 | L24-L34 |
| L2 | L50-L56 | L50-L56 |
| L3 | L89-L97 | L89-L97 |

TABLE A-continued

Residues in CDRs according to Kabat and Chothia numbering schemes.

| CDR | Kabat | Chothia |
|-----|-------|---------|
| H1 (Kabat Numbering) | H26-H35* | H26-H35* |
| H1 (Chothia Numbering) | H26-H35 | H26-H35 |
| H2 | H50-H58 | H50-H58 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

As used herein, the term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a poly peptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')₂" fragments contain two Fab' fragments joined, near the hinge region, by disulfide bonds. F(ab')₂ fragments may be generated, for example, by recombinant methods or by pepsin digestion of an intact antibody. The F(ab') fragments can be dissociated, for example, by treatment with IS-mercaptoethanol.

"Fv" fragments comprise a non-covalently-linked dimer of one heavy chain variable domain and one light chain variable domain.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies, vol.* 113, Rosenburg and Moore eds., Springer-Verlag. New York, pp. 269-315 (1994). HER2 antibody scFv fragments are described in WO93/16185; U.S. Pat. Nos. 5,571,894; and 5,587,458.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$, or $V_L$-$V_H$). Any suitable Fc domain known in the art or described herein may be used. In some cases, the Fc domain comprises an IgG4 Fc domain.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al., *FEBS Letters,* 1998, 414:521-526 and Muyldermans et al., *Trends in Biochem. Sci.,* 2001, 26:230-245, each of which is incorporated by reference in its entirety. Single domain antibodies are also known as sdAbs or nanobodies. Sdabs are fairly stable and easy to express as fusion partner with the Fc chain of an antibody (Harmsen M M. De Haard H J (2007). "Properties, production, and applications of camelid single-domain antibody fragments". Appl. Microbiol Biotechnol. 77(1): 13-22).

The terms "full length antibody," "intact antibody." and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "epitope" means a portion of an antigen that specifically binds to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to TREM2 variants with different point-mutations, or to chimeric TREM2 variants.

A "multispecific antibody" is an antibody that comprises two or more different antigen-binding domains that collectively specifically bind two or more different epitopes. The two or more different epitopes may be epitopes on the same antigen (e.g., a single TREM2 molecule expressed by a cell) or on different antigens (e.g., different TREM2 molecules expressed by the same cell, or a TREM2 molecule and a non-TREM2 molecule). In some aspects, a multi-specific antibody binds two different epitopes (i.e., a "bispecific antibody"). In some aspects, a multi-specific antibody binds three different epitopes (i.e., a "trispecific antibody").

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

"Effector functions" refer to those biological activities mediated by the Fc region of an antibody, which activities may vary depending on the antibody isotype. Examples of antibody effector functions include C1q binding to activate complement dependent cytotoxicity (CDC). Fc receptor binding to activate antibody-dependent cellular cytotoxicity (ADCC), and antibody dependent cellular phagocytosis (ADCP), receptor ligand blocking, agonism, or antagonism.

Anti-TREM2 antibodies can include those described herein such as the clones set forth in the tables. In some embodiments, the antibody comprises an alternative scaffold. In some embodiments, the antibody consists of an alternative scaffold. In some embodiments, the antibody consists essentially of an alternative scaffold. In some embodiments, the antibody comprises an antibody fragment. In some embodiments, the antibody consists of an antibody fragment. In some embodiments, the antibody consists essentially of an antibody fragment. A "TREM2 antibody," "anti-TREM2 antibody," or "TREM2-specific antibody" is an antibody, as provided herein, which specifically binds to the antigen TREM2. In some embodiments, the antibody binds the extracellular domain of TREM2. In certain embodiments, a TREM2 antibody provided herein binds to an epitope of TREM2 that is conserved between or among TREM2 proteins from different species.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. The humanized antibody is less likely to induce an immune response, and/or induces a less severe immune response, as compared to the non-human species antibody, when it is administered to a human subject. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. Examples of how to make humanized antibodies can be found in U.S. Pat. Nos. 6,054,297, 5,886,152 and 5,877,293, each of which is incorporated by reference in its entirety. For further details, see Jones et al., *Nature,* 1986, 321:522-525; Riechmann et al., *Nature,* 1988, 332:323-329; and Presta. *Curr. Op. Struct. Bol.,* 1992, 2:593-596, each of which is incorporated by reference in its entirety.

In one embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies. In one embodiment, all of the variable and constant domains are derived from human immunoglobulin sequences (a fully human antibody). These antibodies may be prepared in a variety of ways including through the immunization with an antigen of interest of a mouse that is genetically modified to express antibodies derived from human heavy and/or light chain-encoding genes.

In some embodiments, the antibodies provided herein comprise an antibody fragment. In some embodiments, the antibodies provided herein consist of an antibody fragment. In some embodiments, the antibodies provided herein consist essentially of an antibody fragment. In some embodiments, the antibody fragment is an Fv fragment. In some embodiments, the antibody fragment is a Fab fragment. In some embodiments, the antibody fragment is a F(ab')$_2$ fragment. In some embodiments, the antibody fragment is a Fab' fragment. In some embodiments, the antibody fragment is an scFv (sFv) fragment. In some embodiments, the antibody fragment is an scFv-Fc fragment. In some embodiments, the antibody fragment is a fragment of a single domain antibody.

Sequences of TREM2 Antibodies $V_H$ Domains

In some embodiments, an antibody provided herein comprises a $V_H$ sequence selected from SEQ ID NOs: 1, 3, 5, and 7. In some embodiments, an antibody provided herein comprises a VH sequence of SEQ ID NO:1. In some embodiments, an antibody provided herein comprises a $V_H$ sequence of SEQ ID NO:3. In some embodiments, an antibody provided herein comprises a $V_H$ sequence of SEQ ID NO:5. In some embodiments, an antibody provided herein comprises a $V_H$ sequence of SEQ ID NO:7.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 1, 3, 5, and 7. In some embodiments, an antibody provided herein comprises a $V_H$ sequence provided in SEQ ID NOs: 1, 3, 5, and 7, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

$V_L$ Domains

In some embodiments, an antibody provided herein comprises a $V_L$ sequence selected from SEQ ID NOs: 2, 4, 6, and 8. In some embodiments, an antibody provided herein comprises a $V_L$ sequence of SEQ ID NO:2. In some embodiments, an antibody provided herein comprises a $V_L$ sequence of SEQ ID NO:4. In some embodiments, an antibody provided herein comprises a $V_L$ sequence of SEQ ID NO:6. In some embodiments, an antibody provided herein comprises a $V_L$ sequence of SEQ ID NO:8.

In some embodiments, an antibody provided herein comprises a $V_L$ sequence having at least about 50%, 60%, 70%, 80%, 90%, 95%, or 99% identity to an illustrative $V_L$ sequence provided in SEQ ID NOs: 2, 4, 6, and 8. In some embodiments, an antibody provided herein comprises a $V_L$ sequence provided in SEQ ID NOs: 2, 4, 6, and 8, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

$V_H$-$V_L$ Combinations

In some embodiments, an antibody provided herein comprises a $V_H$ sequence selected from SEQ ID NOs: 1, 3, 5, and 7; and a $V_L$ sequence selected from SEQ ID NOs: 2, 4, 6, and 8.

In some embodiments, an antibody provided herein comprises a $V_H$ sequence of SEQ ID NO:1 and a $V_L$ sequence of SEQ ID NO:2. In some embodiments, an antibody provided herein comprises a $V_H$ sequence of SEQ ID NO:3 and a $V_L$ sequence of SEQ ID NO:4. In some embodiments, an antibody provided herein comprises a $V_H$ sequence of SEQ ID NO:5 and a $V_L$ sequence of SEQ ID NO:6. In some embodiments, an antibody provided herein comprises a $V_H$ sequence of SEQ ID NO:7 and a $V_L$ sequence of SEQ ID NO:8. In certain aspects, any of SEQ ID NOs: 1, 3, 5, and 7 can be combined with any of SEQ ID NOs: 2, 4, 6, and 8. For example, SEQ ID NO:1 can be combined with any of SEQ ID NO: 2, 4, 6, or 8. As another example, SEQ ID NO:2 can be combined with any of SEQ ID NO: 1, 3, 5, or 7.

In some embodiments, an antibody provided herein comprises a $V_H$ sequence having at least about 50%, 60%, 70%, 80%, 90%, 95%, or 99% identity to an illustrative VH sequence provided in SEQ ID NOs: 1, 3, 5, and 7; and a $V_L$ sequence having at least about 50%, 60%, 70%, 80%, 90%, 95%, or 99% identity to an illustrative VL sequence provided in SEQ ID NOs: 2, 4, 6, and 8. In some embodiments, an antibody provided herein comprises a VH sequence provided in SEQ ID NOs: 1, 3, 5, and 7, with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a VL sequence provided in SEQ ID NOs: 2, 4, 6, and 8, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

CDRs

In some embodiments, an antibody provided herein comprises one to three CDRs of a $V_H$ domain selected from SEQ ID NOs: 1, 3, 5, and 7. In some embodiments, an antibody provided herein comprises two to three CDRs of a $V_H$ domain selected from SEQ ID NOs: 1, 3, 5, and 7. In some embodiments, an antibody provided herein comprises three CDRs of a VH domain selected from SEQ ID NOs: 1, 3, 5, and 7. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 1, 3, 5, and 7. In some embodiments, the CDR-H1 is a CDR-H1 of a VH domain selected from SEQ ID NOs: 1, 3, 5, and 7, with up to 1, 2, 3, 4, or 5 amino acid substitutions. In some embodiments, the CDR-H2 is a CDR-H2 of a VH domain selected from SEQ ID NOs: 1, 3, 5, and 7, with up to 1, 2, 3, 4, 5, 6, 7, or 8 amino acid substitutions. In some embodiments, the CDR-H3 is a CDR-H3 of a VH domain selected from SEQ ID NOs: 1, 3, 5, and 7, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VL domain selected from SEQ ID NOs: 2, 4, 6, and 8. In some embodiments, an antibody provided herein comprises two to three CDRs of a VL domain selected from SEQ ID NOs: 2, 4, 6, and 8. In some embodiments, an antibody provided herein comprises three CDRs of a VL domain selected from SEQ ID NOs: 2, 4, 6, and 8. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

CDRs for VH and VL as defined using Kabat, Chothia, AbM, Contact, and IMGT are shown in Table A1 below.

TABLE A1

| Region | Definition | Sequence Fragment | SEQ ID NO |
|--------|-----------|-------------------|-----------|
| CDR-H1 | Chothia | GFTFSNY--- | 45 |
|        | AbM | GFTFSNYYMA | 39 |
|        | Kabat | -----NYYMA | 46 |
|        | Contact | ----SNYYMA | 47 |
|        | IMGT | GFTFSNYY-- | 48 |
| CDR-H2 | Chothia | -----TNSGGS--------- | 49 |
|        | AbM | ---SLTNSGGSTY------- | 40 |
|        | Kabat | ---SLTNSGGSTYYADSVKG | 50 |
|        | Contact | WVSSLTNSGGSTY------- | 51 |

TABLE A1-continued

| Region | Definition | Sequence Fragment | SEQ ID NO |
|--------|------------|-------------------|-----------|
| | IMGT | ----LTNSGGST-------- | 52 |
| CDR-H3 | Chothia | --EWAGSGYFDY | 41 |
| | AbM | --EWAGSGYFDY | 41 |
| | Kabat | --EWAGSGYFDY | 41 |
| | Contact | TREWAGSGYFD- | 53 |
| | IMGT | TREWAGSGYFDY | 54 |
| CDR-L1 | Chothia | KASQNVGNNLA-- | 42 |
| | AbM | KASQNVGNNLA-- | 42 |
| | Kabat | KASQNVGNNLA-- | 42 |
| | Contact | ------GNNLAWY | 55 |
| | IMGT | ---QNVGNN---- | 56 |
| CDR-L2 | Chothia | ----YTSNRFT | 43 |
| | AbM | ----YTSNRFT | 43 |
| | Kabat | ----YTSNRFT | 43 |
| | Contact | LLIYYTSNRF- | 57 |
| | IMGT | ----YT----- | 58 |
| CDR-L3 | Chothia | QRIYNSPWT | 44 |
| | AbM | QRIYNSPWT | 44 |
| | Kabat | QRIYNSPWT | 44 |
| | Contact | QRIYNSPW- | 59 |
| | IMGT | QRIYNSPWT | 44 |

In some embodiments, the CDRs are CDRs having at least about 50%, 75%, 80%, 85%, 90%, or 95% identity with a CDR-L1, CDR-L2, or CDR-L3 of SEQ ID NOs: 2, 4, 6, and 8. In some embodiments, the CDR-L1 is a CDR-L1 of a VL domain selected from SEQ ID NOs: 2, 4, 6, and 8, with up to 1, 2, 3, 4, or 5 amino acid substitutions. In some embodiments, the CDR-L2 is a CDR-L2 of a VL domain selected from SEQ ID NOs: 2, 4, 6, and 8, with up to 1, 2, 3, 4, 5, 6, 7, or 8 amino acid substitutions. In some embodiments, the CDR-L3 is a CDR-L3 of a VL domain selected from SEQ ID NOs: 2, 4, 6, and 8, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VH domain selected from SEQ ID NOs: 1, 3, 5, and 7 and one to three CDRs of a VL domain selected from SEQ ID NOs: 2, 4, 6, and 8. In some embodiments, an antibody provided herein comprises two to three CDRs of a VH domain selected from SEQ ID NOs: 1, 3, 5, and 7 and two to three CDRs of a VL domain selected from SEQ ID NOs: 2, 4, 6, and 8. In some embodiments, an antibody provided herein comprises three CDRs of a VH domain selected from SEQ ID NOs: 1, 3, 5, and 7 and three CDRs of a VL domain selected from SEQ ID NOs: 2, 4, 6, and 8. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, an antibody provided herein comprises a CDR-H3 selected of SEQ ID NO: 11 or 41. In some aspects, the CDR-H3 has at least about 50%, 75%, 80%, 85%, 90%, or 95% identity with a CDR-H3 of SEQ ID NO: 11 or 41. In some embodiments, the CDR-H3 is a CDR-H3 selected of SEQ ID NO: 11 or 41, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H2 of SEQ ID NO: 10 or 40. In some aspects, the CDR-H2 has at least about 50%, 75%, 80%, 85%, 90%, or 95% identity with a CDR-H2 of SEQ ID NO: 10 or 40. In some embodiments, the CDR-H2 is a CDR-H2 of SEQ ID NO: 10 or 40, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO: 9 or 39. In some aspects, the CDR-H1 has at least about 50%, 75%, 80%, 85%, 90%, or 95% identity with a CDR-H1 of SEQ ID NO: 9 or 39. In some embodiments, the CDR-H1 is a CDR-H1 of SEQ ID NO: 9 or 39, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 11 or 41 and a CDR-H2 of SEQ ID NO:10. In some embodiments, an antibody provided herein comprises a CDR-H3 of SEQ ID NO: 11 or 41, a CDR-H2 of SEQ ID NO: 10 or 40, and a CDR-H1 of SEQ ID NO: 9 or 39. In some embodiments, the CDR-H3 has at least about 50%, 75%, 80%, 85%, 90%, or 95% identity with a CDR-H3 of SEQ ID NO: 11 or 41, the CDR-H2 has at least about 50%, 75%, 80%, 85%, 90%, or 95% identity with a CDR-H2 of SEQ ID NO: 10 or 40, and the CDR-H1 has at least about 50%, 75%, 80%, 85%, 90%, or 95% identity with a CDR-H1 of SEQ ID NO: 9 or 39. In some embodiments, the CDR-H3 is a CDR-H3 of SEQ ID NO: 11 or 41, with up to 1, 2, 3, 4, 5, 6, 7, or 8 amino acid substitutions; the CDR-H2 is a CDR-H2 of SEQ ID NO: 10 or 40, with up to 1, 2, 3, 4, 5, 6, 7, or 8 amino acid substitutions; and the CDR-H1 is a CDR-H1 of SEQ ID NO: 9 or 39, with up to 1, 2, 3, 4, or 5 amino acid substitutions.

In some aspects, the amino acid substitutions are conservative amino acid substitutions. In some embodiments, the antibody described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 of SEQ ID NO: 14 or 44. In some aspects, the CDR-L3 has at least about 50%, 75%, 80%, 85%, 90%, or 95% identity with a CDR-L3 of SEQ ID NO: 14 or 44. In some embodiments, the CDR-L3 is a CDR-L3 of SEQ ID NO: 14 or 44, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L2 of SEQ ID NO: 13 or 43. In some aspects, the CDR-L2 has at least about 50%, 75%, 80%, 85%, 90%, or 95% identity with a CDR-L2 of SEQ ID NO: 13 or 43. In some embodiments, the CDR-L2 is a CDR-L2 of SEQ ID NO: 13 or 43, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L1 of SEQ ID NO: 12 or 42. In some aspects, the CDR-L1 has at least about 50%, 75%, 80%, 85%, 90%, or 95% identity with a CDR-L1 of SEQ ID NO: 12 or 42. In some embodiments, the CDR-L1 is a CDR-L1 of SEQ ID NO: 12 or 42, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 of SEQ ID NO: 14 or 44 and a CDR-L2 of SEQ ID NO: 13 or 43. In some embodiments, an antibody provided herein comprises a CDR-L3 of SEQ ID NO: 14 or 44, a CDR-L2 of SEQ ID NO: 13 or 43, and a CDR-L1 of SEQ ID NO: 12 or 42. In some embodiments, the CDR-L3 has at least about 50%, 75%, 80%, 85%, 90%, or 95% identity with a CDR-L3 of SEQ ID NO: 14 or 44, the CDR-L2 has at least about 50%, 75%, 80%, 85%, 90%, or 95% identity with a CDR-L2 of SEQ ID NO: 13 or 43, and the CDR-L1 has at least about 50%, 75%, 80%, 85%, 90%, or 95% identity with a CDR-L1 of SEQ ID NO: 12 or 42. In some embodiments, the CDR-L3 is a CDR-L3 of SEQ ID NO: 14 or 44, with up to 1, 2, 3, 4, or 5 amino acid substitutions, the CDR-L2 is a CDR-L2 of SEQ ID NO: 13 or 43, with up to 1, 2, 3, or 4 amino acid substitutions; and the CDR-L1 is a CDR-L1 of SEQ ID NO: 12 or 42, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 11 or 41, a CDR-H2 of SEQ ID NO: 10 or 40, a CDR-H1 of SEQ ID NO: 9 or 39, a CDR-L3 of SEQ ID NO: 14 or 44, a CDR-L2 of SEQ ID NO: 13 or 43, and a CDR-L1 of SEQ ID NO: 12 or 42. In some embodiments, the CDR-H3 has at least about 50%, 75%, 80%, 85%, 90%, or 95% identity with a CDR-H3 of SEQ ID NO: 11 or 41, the CDR-H2 has at least about 50%, 75%, 80%, 85%, 90%, or 95% identity with a CDR-H2 of SEQ ID NO: 10 or 40, the CDR-H1 has at least about 50%, 75%, 80%, 85%, 90%, or 95% identity with a CDR-H1 of SEQ ID NO: 9 or 39, the CDR-L3 has at least about 50%, 75%, 80%, 85%, 90%, or 95% identity with a CDR-L3 of SEQ ID NO: 14 or 44, the CDR-L2 has at least about 50%, 75%, 80%, 85%, 90%, or 95% identity with a CDR-L2 of SEQ ID NO: 13 or 43, and the CDR-L1 has at least about 50%, 75%, 80%, 85%, 90%, or 95% identity with a CDR-L1 of SEQ ID NO: 12 or 42. In some embodiments, the CDR-H3 is a CDR-H3 of SEQ ID NO: 11 or 41, with up to 1, 2, 3, 4, 5, 6, 7, or 8 amino acid substitutions; the CDR-H2 is a CDR-H2 of SEQ ID NO: 10 or 40, with up to 1, 2, 3, 4, 5, 6, 7, or 8 amino acid substitutions; the CDR-H1 is a CDR-H1 of SEQ ID NO: 9 or 39, with up to 1, 2, 3, 4, or 5 amino acid substitutions; the CDR-L3 is a CDR-L3 of SEQ ID NO: 14 or 44, with up to 1, 2, 3, 4, or 5 amino acid substitutions; the CDR-L2 is a CDR-L2 of SEQ ID NO: 13 or 43, with up to 1, 2, 3, or 4 amino acid substitutions; and the CDR-L1 is a CDR-L1 of SEQ ID NO: 12 or 42, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO:9, a CDR-H2 of SEQ ID NO:10, a CDR-H3 of SEQ ID NO:11, a CDR-L1 of SEQ ID NO:12, a CDR-L2 of SEQ ID NO:13, and a CDR-L1 of SEQ ID NO:14. In some embodiments, an antibody provided herein comprises a CDR-H1 of SEQ ID NO:39, a CDR-H2 of SEQ ID NO:40, a CDR-H3 of SEQ ID NO:41, a CDR-L1 of SEQ ID NO:42, a CDR-L2 of SEQ ID NO:43, and a CDR-L1 of SEQ ID NO:44.

Fc Region

The term "Fc domain" or "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, MD, 1991. An "Fc polypeptide" of a dimeric Fc as used herein refers to one of the two polypeptides forming the dimeric Fc domain. i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence. An Fc can be of the class IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor. FcRn, which is responsible for the transfer of maternal IgGs to the fetus (Guyer et al., J. Immunol. 117:587 (1976); and Kim et al., J. Immunol. 24:249 (1994)).

In some embodiments, an antibody is an IgG1 antibody. In some embodiments, an antibody is an IgG3 antibody. In some embodiments, an antibody is an IgG2 antibody. In some embodiments, an antibody is an IgG4 antibody.

Modifications in the CH2 domain can affect the binding of FcRs to the Fc. A number of amino acid modifications in the Fc region are known in the art for selectively altering the affinity of the Fc for different Fc-gamma (Fcγ) receptors. In one embodiment, the Fc comprises one or more modifications to promote selective binding of Fc-gamma receptors. Exemplary mutations that alter the binding of FcRs to the Fc are listed below:

S298A/E333A/K334A, S298A/K333A/K334A/K326A (Lu Y, Vernes J M, Chiang N, et al. J Immunol Methods. 2011 Feb. 28; 365(1-2):132-41);

F243L/R292P/Y300L/V305I/P396L, F243L/R292P/Y300L/L235V/P396L (Stavenhagen J B, Gorlatov S, Tuaillon N, et al. Cancer Res. 2007 Sep. 15; 67(18): 8882-90; Nordstrom J L, Gorlatov S, Zhang W, et al. Breast Cancer Res. 2011 Nov. 30; 13(6):R123);

F243L (Stewart R, Thom G, Levens M. et al. Protein Eng Des Sel. 2011 September; 24(9):671-8.), S298A/E333A/K334A (Shields R L, Namenuk A K, Hong K, et al. J Biol Chem. 2001 Mar. 2; 276(9):6591-604);

S239D/I332E/A330L, S239D/I332E (Lazar G A, Dang W, Karki S, et al. Proc Natl Acad Sci USA. 2006 Mar. 14; 103(11):4005-10);

S239D/S267E, S267E/L328F (Chu S Y, Vostiar I, Karki S, et al. Mol Immunol. 2008 September; 45(15):3926-33);

S239D/D265S/S298A/I332E, S239E/S298A/K326A/A327H, G237F/S298A/A330L/I332E, S2 39D/I332E/S298A, S239D/K326E/A330L/I332E/S298A, G236A/S239D/D270L/I332E, S239E/S267E/H 268D, L234F/S267E/N325L, G237F/V266L/S267D and other mutations listed in WO2011/120134 and WO2011/120135, herein incorporated by reference. *Therapeutic Antibody Engineering* (by William R. Strohl and Lila M. Strohl, Woodhead Publishing series in Biomedicine No 11, ISBN 1 907568 37 9, October 2012) lists mutations on page 283.

In some embodiments an antibody described herein includes modifications to improve its ability to mediate effector function. Such modifications are known in the art and include afucosylation, or engineering of the affinity of the Fc towards an activating receptor, mainly FCGR3a for ADCC, and towards C1q for CDC. The Table B, below, summarizes various designs reported in the literature for effector function engineering.

In certain embodiments, an antibody provided herein comprises an Fc region with one or more amino acid substitutions which improve ADCC, such as a substitution at one or more of positions 298, 333, and 334 of the Fc region. In some embodiments, an antibody provided herein comprises an Fc region with one or more amino acid substitutions at positions 239, 332, and 330, as described in Lazar et al., *Proc. Natl. Acad. Sci. USA*, 2006, 103:4005-4010, incorporated by reference in its entirety.

In some embodiments, an antibody provided herein comprises one or more alterations that improves or diminishes C1q binding and/or CDC. See U.S. Pat. No. 6,194,551; WO 99/51642; and Idusogie et al., *J. Immunol.*, 2000, 164: 41784184, each of which is incorporated by reference in its entirety.

Thus, in one embodiment, an antibody described herein can include a dimeric Fc that comprises one or more amino acid modifications as noted in Table B that confer improved effector function. In another embodiment, the antibody can be afucosylated to improve effector function.

TABLE B

| CH2 domains and effector function engineering | | |
|---|---|---|
| Reference | Mutations | Effect |
| Lu, 2011, Ferrara 2011, Mizushima 2011 | Afucosylated | Increased ADCC |

TABLE B-continued

CH2 domains and effector function engineering

| Reference | Mutations | Effect |
|---|---|---|
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Fc modifications reducing FcγR and/or complement binding and/or effector function are known in the art. Recent publications describe strategies that have been used to engineer antibodies with reduced or silenced effector activity (see Strobl, W R (2009), Cuff Opin Biotech 20:685-691, and Strobl, W R and Strohl L M, "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the binge or CH2 regions of the Fc. For example, US Patent Publication No. 2011/0212087 (Strobl). International Patent Publication No. WO 2006/105338 (Xencor), US Patent Publication No. 2012/0225058 (Xencor), US Patent Publication No. 2012/0251531 (Genentech), and Strop et al ((2012) J. Mol. Biol. 420: 204-219) describe specific modifications to reduce FcγR or complement binding to the Fc.

Specific, non-limiting examples of known amino acid modifications to reduce FcγR or complement binding to the Fc include those identified in the following Table C:

TABLE C

Modifications to reduce FcγR or complement binding to the Fc

| Company | Mutations |
|---|---|
| GSK | N297A |
| Ortho Biotech | L234A/L235A |
| Protein Design labs | IGG2 V234A/G237A |
| Wellcome Labs | IGG4 L235A/G237A/E318A |
| GSK | IGG4 S228P/L236E |
| Alexion | IGG2/IGG4combo |
| Merck | IGG2 H268Q/V309L/A330S/A331S |
| Bristol-Myers | C220S/C226S/C229S/P238S |
| Seattle Genetics | C226S/C229S/E3233P/L235V/L235A |
| Amgen | *E. coli* production, non glyco |
| Medimune | L234F/L235E/P331S |
| Trubion | Hinge mutant, possibly C226S/P230S |

Methods of producing antibodies with little or no fucose on the Fc glycosylation site (Asn 297 EU numbering) without altering the amino acid sequence are well known in the art. The GlymaxX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells. (von Horsten et al. (2010) Glycobiology. 2010 December; 20 (12):1607-18.) Examples of cell lines capable of producing defucosylated antibody include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., *Arch. Biochem. Biophys.,* 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., *Biotech. Bioeng.,* 2004, 87: 614-622; Kanda et al., *Biotechnol. Bioeng.,* 2006, 94:680-688; and WO 2003/085107; each of which is incorporated by reference in its entirety). Another approach to obtaining antibodies with lowered levels of fucosylation can be found in U.S. Pat. No. 8,409,572, which teaches selecting cell lines for antibody production for their ability to yield lower levels of fucosylation on antibodies Antibodies can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

In some aspects, an antibody provided herein comprises an IgG1 domain with reduced fucose content at position Asn 297 compared to a naturally occurring IgG1 domain. Such Fc domains are known to have improved ADCC. See Shields et al., *J. Biol. Chem.,* 2002, 277:26733-26740, incorporated by reference in its entirety. In some aspects, such antibodies do not comprise any fucose at position Asn 297. The amount of fucose may be determined using any suitable method, for example as described in WO 2008/077546, incorporated by reference in its entirety.

In some embodiments, an antibody provided herein comprises a bisected oligosaccharide, such as a biantennary oligosaccharide attached to the Fc region of the antibody that is bisected by GlcNAc. Such antibody variants may have reduced fucosylation and/or improved ADCC function. Examples of such antibody variants are described, for example, in WO 2003/011878; U.S. Pat. No. 6,602,684; and U.S. Pat. Pub. No. 2005/0123546; each of which is incorporated by reference in its entirety.

Other illustrative glycosylation variants which may be incorporated into the antibodies provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., *J. Mol. Biol.,* 2004, 336:1239-1249; and Yamane-Ohnuki et al., *Biotech. Bioeng.,* 2004, 87: 614-622; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO 1997/30087; WO 1998/58964; and WO 1999/22764; each of which his incorporated by reference in its entirety.

Examples of cell lines capable of producing defucosylated antibodies include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., *Arch. Biochem. Biophys.*, 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., *Biotech. Bioeng.*, 2004, 87: 614-622; Kanda et al., *Biotechnol. Bioeng.*, 2006, 94:680-688; and WO 2003/085107, each of which is incorporated by reference in its entirety).

In some embodiments, an antibody has antibody-dependent cellular phagocytosis (ADCP) activity. ADCP can occur when antibodies bind to antigens on the surface of pathogenic or tumorigenic target-cells. Phagocytic cells bearing Fc receptors on their cell surface, including monocytes and macrophages, recognize and bind the Fc region of antibodies bound to target-cells. Upon binding of the Fc receptor to the antibody-bound target cell, phagocytosis of the target cell can be initiated. ADCP can be considered a form of ADCC.

In some embodiments, the antibodies are capable of forming an immune complex. For example, an immune complex can be a tumor cell covered by antibodies.

In some aspects, an anti-TREM2 antibody does not substantially bind myeloid cells present outside of cancer tissue. In some aspects, an anti-TREM2 antibody does not substantially bind stimulatory myeloid cells present in cancer tissue.

In some embodiments the antibodies are monoclonal antibodies.

In some embodiments the antibodies are polyclonal antibodies.

In some embodiments the antibodies are produced by hybridomas. In other embodiments, the antibodies are produced by recombinant cells engineered to express the desired variable and constant domains.

In some embodiments the antibodies may be single chain antibodies or other antibody derivatives retaining the antigen specificity and the lower hinge region or a variant thereof.

In some embodiments the antibodies may be polyfunctional antibodies, recombinant antibodies, human antibodies, humanized antibodies, fragments or variants thereof. In particular embodiments, the antibody fragment or a derivative thereof is selected from a Fab fragment, a Fab'2 fragment, a CDR and ScFv.

In some embodiments, antibodies are specific for surface antigens, such as TREM2 protein. In some embodiments, therapeutic antibodies are specific for tumor antigens (e.g., molecules specifically expressed by tumor cells). In particular embodiments, the therapeutic antibodies may have human or non-human primate IgG1 or IgG3 Fc portions.

Binding

With regard to the binding of an antibody to a target molecule, the terms "bind." "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule.

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

The term "$k_d$" (sec$^{-1}$), as used herein, refers to the dissociation rate constant of a particular antibody-antigen interaction. This value is also referred to as the $k_{off}$ value.

The term "$k_a$" (M$^{-1}$×sec$^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D=k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" (M$^{-1}$), as used herein, refers to the association equilibrium constant of a particular antibody-antigen interaction. $K_A=k_a/k_d$.

When used herein in the context of two or more antibodies, the term "competes with" or "cross-competes with" indicates that the two or more antibodies compete for binding to an antigen (e.g., TREM2). In one exemplary assay. TREM2 is coated on a surface and contacted with a first TREM2 antibody, after which a second TREM2 antibody is added. In another exemplary assay, a first TREM2 antibody is coated on a surface and contacted with TREM2, and then a second TREM2 antibody is added. If the presence of the first TREM2 antibody reduces binding of the second TREM2 antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the antibodies for TREM2 and the valency of the antibodies. The assays described in this definition are illustrative, and a skilled artisan can utilize any suitable assay to determine if antibodies compete with each other. Suitable assays are described, for example, in Cox et al., "Immunoassay Methods," in *Assay Guidance Manual [Internet]*, Updated Dec. 24, 2014 (www.ncbi.nlm.nih.gov/books/ NBK92434/; accessed Sep. 29, 2015); Silman et al., *Cytometry*, 2001, 44:30-37; and Finco et al., *J. Pharm. Biomed Anal.*, 2011, 54:351-358; each of which is incorporated by reference in its entirety.

In some embodiments, an antibody provided herein binds human TREM2 with a $K_D$ of less than or equal to about 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 1.95, 2, 3, 4, 5, 6, 7, 8, 9, or $10 \times 10^{-9}$ M, as measured by Biacore assay. In some embodiments, the $K_D$ of the antibody provided herein is between about 0.001-0.01, 0.01-0.1, 0.01-0.05, 0.05-0.1, 0.1-0.5, 0.5-1, 0.25-0.75, 0.25-0.5, 0.5-0.75, 0.75-1, 0.75-2, 1.1-1.2, 1.2-1.3, 1.3-1.4, 1.4-1.5, 1.5-1.6, 1.6-1.7, 1.7-1.8, 1.8-1.9, 1.9-2, 1-2, 1-5, 2-7, 3-8, 3-5, 4-6, 5-7, 6-8, 7-9, 7-10, or $5-10 \times 10^{-9}$ M, as measured by Biacore assay.

In some embodiments, the antibody provided herein binds human TREM2 with a $K_D$ of less than or equal to about 2, 1.98, 1.95, 1.9, 1.85, 1.8, 1.75, 1.7, 1.65, 1.6, 1.55, 1.50, 1.45, or $1.4 \times 10^{-9}$ M, or less, as measured by Biacore assay. In some embodiments, the antibody provided herein binds human TREM2 with a $K_D$ between 1.9-1.8, 1.8-1.7, 1.7-1.6, 1.6-1.5, or $1.9-1.5 \times 10^{-9}$ M as measured by Biacore assay. In some embodiments, the antibody provided herein binds human TREM2 with a $K_d$ of less than or equal to about 10, 9.56, 9.5, 9.0, 8.88, 8.84, 8.5, 8, 7.5, 7.32, 7, 6.5, 6, 5.5, 5, 4.5, 4, 3.5, 3, 2.5, 2, 1.5, or $1 \times 10^{-4}$ (l/s), or less, as measured by Biacore assay. In some embodiments, the antibody provided herein binds human TREM2 with a $K_d$ between 7-10, 7-8, 8-9, 9-10, 7-7.5, 7.5-8, 8.-8.5, 8.5-9, 9-9.5, or $9.5-10 \times 10^{-4}$ (l/s) as measured by Biacore assay. In some embodiments, the antibody provided herein binds human TREM2 with a $K_a$ of greater than or equal to about 4, 4.1, 4.2, 4.3, 4.4, 4.5, 4.6, 4.7, 4.8, 4.9, 45, 5.1, 5.2, 5.3, 5.4, 5.5, 5.6, 5.7, 5.8, 5.9, 6, 7, 8, 9, or $10 \times 10^5$ (l/Ms), or more, as measured by Biacore assay. In some embodiments, the antibody provided herein binds human TREM2 with a $K_a$ between 4-7, 4-4.5, 4.5-5, 5-5.5, 5.5-6, 6-6.5, or 6.5-7, 7-8, 8-9, or $9-10 \times 10^5$ (l/Ms) as measured by Biacore assay.

In some embodiments, the antibody provided herein binds human TREM2 with an EC50 of less than or equal to 2, 1.9, 1.8, 1.7, 1.6, 1.5, 1.4, 1.3, 1.2, 1.1, 0.9, 0.8, 0.7, 0.6, 0.5, 0.4, 0.3, 0.2, or 0.1 nM as measured by measured by flow cytometry. In some embodiments, the antibody binds human TREM2 with an EC50 between 0.6-1.4 nM as measured by measured by flow cytometry. In some embodiments, the antibody binds human TREM2 with an EC50 of about 0.5, 0.6, 0.9, 1.1, 1.2, 1.3, 1.4, or 1.5 nM as measured by measured by flow cytometry.

In some embodiments, the antibody provided herein binds mouse TREM2 with an EC50 of less than or equal to 2, 1.9, 1.8, 1.7, 1.6, 1.5, 1.4, 1.3, 1.2, 1.1, 0.9, 0.8, 0.7, 0.6, 0.5, 0.4, 0.3, 0.2, or 0.1 nM as measured by measured by flow cytometry. In some embodiments, the antibody binds mouse TREM2 with an EC50 between 0.6-1.4 nM as measured by measured by flow cytometry. In some embodiments, the antibody binds mouse TREM2 with an EC50 of about 0.5, 0.6, 0.9, 1.1, 1.2, 1.3, 1.4, or 1.5 nM as measured by measured by flow cytometry.

In some embodiments, the antibody provided herein does not bind human TREM2 with an EC50 great than or equal to 20 nM or more as measured by measured by flow cytometry. In some embodiments, the antibody provided herein does not bind mouse TREM2 with an EC50 great than or equal to 3 nM or more as measured by measured by flow cytometry.

To screen for antibodies which bind to an epitope on a target antigen bound by an antibody of interest (e.g., TREM2), a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art.

Competition between antibodies can be determined by an assay in which an antibody under test inhibits or blocks specific binding of a reference antibody to a common antigen (see, e.g., Junghans et al., Cancer Res. 50:1495, 1990; Fendly et al. Cancer Research 50: 1550-1558; U.S. Pat. No. 6,949,245). A test antibody competes with a reference antibody if an excess of a test antibody (e.g., at least 2×, 5×, 10×, 20×, or 100×) inhibits or blocks binding of the reference antibody by, e.g., at least 50%, 60%, 70%, 75%, 80%, 85%, 90%, 95%, or 99% as measured in a competitive binding assay. Antibodies identified by competition assay (competing antibody) include antibodies binding to the same epitope as the reference antibody and antibodies binding to an adjacent epitope sufficiently proximal to the epitope bound by the reference antibody for steric hindrance to occur. For example, a second, competing antibody can be identified that competes for binding to TREM2 with a first antibody described herein. In certain instances, the second antibody can block or inhibit binding of the first antibody by, e.g., at least 50%, 60%, 70%, 75%, 80%, 85%, 90%, 95%, or 99% as measured in a competitive binding assay. In certain instances, the second antibody can displace the first antibody by greater than 50%, 60%, 70%, 75%, 80%, 85%, 90%, 95%, or 99%.

Function

In some embodiments, the antibody has antibody-dependent cellular cytotoxicity (ADCC) activity. ADCC can occur when antibodies bind to antigens on the surface of pathogenic or tumorigenic target-cells. Effector cells bearing Fc gamma receptors (FcγR or FCGR) on their cell surface, including cytotoxic T-cells, natural killer (NK) cells, macrophages, neutrophils, eosinophils, dendritic cells, or monocytes, recognize and bind the Fc region of antibodies bound to the target-cells. Such binding can trigger the activation of intracellular signaling pathways leading to cell death. In particular embodiments, the antibody's immunoglobulin Fc region subtypes (isotypes) include human IgG1 and IgG3. As used herein, ADCC refers to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci. (USA)* 95:652-656 (1998).

In some embodiments, the antibody has complement-dependent cytotoxicity (CDC) activity. Antibody-induced CDC is mediated through the proteins of the classical complement cascade and is triggered by binding of the complement protein C1q to the antibody. Antibody Fc region binding to C1q can induce activation of the complement cascade. In particular embodiments, the antibody's immunoglobulin Fc region subtypes (isotypes) include human IgG1 and IgG3. As used herein, CDC refers to the ability of a molecule to lyse a target in the presence of complement. The complement activation pathway is initiated by the binding of the first component of the complement system (C1q) to a molecule (e.g. polypeptide (e.g., an antibody)) complexed with a cognate antigen. To assess complement activation, a CDC assay, e.g. as described in Gazzano-Santoro et al., *J. Immunol. Methods* 202:163 (1996), may be performed.

In some embodiments, an antibody is an agonistic antibody. An agonistic antibody can induce (e.g., increase) one or more activities or functions of NSMs after the antibody binds a TREM2 protein expressed on the cell. The agonistic antibody may bind to and activate NSMs, causing changes in proliferation of the cell or modifying antigen presentation capabilities. The agonistic antibody may bind to and activate NSMs, triggering intracellular signaling pathways that lead to modified cell growth or apoptosis.

In some embodiments, an antibody is an antagonistic antibody. An antagonistic antibody can block (e.g. decrease) one or more activities or functions of NSMs after the antibody binds a TREM2 protein expressed on the cell. For example, the antagonist antibody may bind to and block ligand binding to one or more NSM proteins, preventing differentiation and proliferation of the cell or modifying antigen presentation capabilities. The antagonist antibody may bind to and prevent activation of a TREM2 protein by its ligand, modifying intracellular signaling pathways that contribute to cell growth and survival.

In some embodiments an antibody is a depleting antibody. A depleting antibody is one that would kill a non-stimulatory myeloid cell upon contact through the antibody's interaction with other immune cells of molecules. For example, antibodies, when bound to cells bearing TREM2 proteins, could engage complement proteins and induce complement-dependent cell lysis. Antibodies, when bound to cells bearing TREM2 proteins, could also trigger neighboring cells bearing Fc receptors to kill them by antibody-dependent cellular cytotoxicity (ADCC).

In some embodiments, an antibody is a neutralizing antibody, and the antibody neutralizes one or more biological activities of NSMs. In some embodiments, TREM2 protein is expressed on the surface of non-stimulatory myeloid cells and the antibody recognizes the extracellular domain of TREM2 protein.

In some embodiments an antibody is selective for NSMs (preferentially binds to TREM2). In certain embodiments, an antibody that selectively binds to NSMs has a dissociation constant (Kd) of range of 0.0001 nM to 1 µM. In certain embodiments, an antibody specifically binds to an epitope on a TREM2 protein that is conserved among the protein from different species. In another embodiment, selective binding includes, but does not require, exclusive binding.

In one embodiment an anti-TREM2 antibody bound to its target is responsible for causing the in vivo depletion of non-stimulatory myeloid cells to which it is bound. In some embodiments, effector proteins induced by clustered antibodies can trigger a variety of responses, including release of inflammatory cytokines, regulation of antigen production, endocytosis, or cell killing. In one embodiment the antibody is capable of recruiting and activating complement or mediating antibody-dependent cellular cytotoxicity (ADCC) in vivo, or mediating phagocytosis by binding Fc receptors in vivo. The antibody may also deplete non-stimulatory myeloid cells by inducing apoptosis or necrosis of the non-stimulatory myeloid cell upon binding.

In some embodiments the disabling of non-stimulatory myeloid cells is in vitro and is achieved: a) by killing of the non-stimulatory myeloid cells; b) magnetic bead depletion of the non-stimulatory myeloid cells; or c) Fluorescence-activated cell sorting (FACS) sorting of the non-stimulatory myeloid cells.

In some embodiments, an antibody is bound to, or conjugated to an effector molecule. In particular embodiments, an antibody is conjugated to at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment.

In certain embodiments an antibody is conjugated to a drug, e.g., a toxin, a chemotherapeutic agent, an immune modulator, or a radioisotope. Several methods of preparing ADCs (antibody drug conjugates) are known in the art and are described in U.S. Pat. No. 8,624,003 (pot method), U.S. Pat. No. 8,163,888 (one-step), and U.S. Pat. No. 5,208,020 (two-step method), for example. An antibody or antigen-binding fragment thereof can be conjugated to at least one agent including a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody, and a second antibody fragment that is antigen binding.

Non-Stimulatory Myeloid Cells (NSMs)

Provided herein are methods and compositions for disabling and/or detecting non-stimulatory myeloid cells (NSMs) comprising the use of an anti-TREM2 antibody. Also provided herein are methods and compositions for targeting and/or detecting non-stimulatory myeloid cells expressing a NSM protein.

Also provided herein are methods and compositions for disabling and/or detecting non-stimulatory myeloid cells comprising the use of antibody directed at a non-human homolog of human NSM protein, in that non-human individual.

As used herein, non-stimulatory myeloid cells are myeloid cells that are not sufficiently effective at stimulating an immune response (e.g. not as effective at stimulating an anti-tumor response in a tumor microenvironment compared to stimulatory myeloid cells). In some embodiments, non-stimulatory myeloid cells are not as effective at presenting an antigen (e.g. a tumor antigen) to T-cells or not as effective at stimulating tumor specific T-cell responses as compared to a stimulatory myeloid cell. In some embodiments, non-stimulatory myeloid cells can display a decreased ability to uptake, process, and/or present tumor-associated antigens to a T cell as compared to a stimulatory myeloid cell. Non-stimulatory myeloid cells may contain a reduced ability or no ability to re-prime cytotoxic T lymphocytes or in some cases cannot stimulate effective tumor-cell killing. Non-stimulatory myeloid cells may display lower expression of gene and cell-surface markers involved in antigen processing, antigen presentation and/or antigen co-stimulation including, without limitation, CD80, CD86, MHCI, and MHCII compared to stimulatory myeloid cells.

Non-stimulatory myeloid cells, when compared to stimulatory myeloid cells, may display the lower expression of genes associated with cross-presentation, co-stimulation, and/or stimulatory cytokines, including, without limitation, any one or more of TAP1, TAP2, PSMB8, PSMB9, TAPBP, PSME2, CD24a, CD274, BTLA, CD40, CD244, ICOSL, ICAM1, TIM3, PDL2, RANK, FLT3, CSF2RB, CSF2RB2, CSF2RA, IL12b, XCR1, CCR7, CCR2, CCL22, CXCL9, and CCL5, and increased expression of anti-inflammatory cytokine IL-10. In some embodiments, non-stimulatory myeloid cells are dependent on the transcription factor IRF4 and the cytokines GM-CSF or CSF-1 for differentiation and survival. In some embodiments, non-stimulatory myeloid cells can contribute to tumoral angiogenesis by secreting vascular endothelial growth factor (VEGF) and nitric oxide synthase (NOS) and support tumor growth by secreting epidermal growth factor (EGF).

In some embodiments, non-stimulatory myeloid cells are tumor-associated macrophages (TAM), neutrophils, monocytes, or dendritic cells (DC). In some embodiments, the non-stimulatory myeloid cell is not a dendritic cell (DC). In some embodiments, non-stimulatory myeloid cells are neutrophils.

In some embodiments, non-stimulatory myeloid cells are tumor-associated macrophages (TAMs). TAMs are macrophages present near or within cancerous tumors, and are derived from circulating monocytes or resident tissue macrophages.

In some embodiments the non-stimulatory myeloid cells and the stimulatory myeloid cells are distinguished on the basis of the markers they express, or the markers they selectively express. The expression of a cell surface markers can be described as '+' or 'positive'. The absence of a cell surface marker can be described as '−' or 'negative'. The expression of a cell surface marker can be further described as 'high' (cells expressing high levels of the makers) or 'low' (cells expressing low levels of the markers), which indicates the relative expression of each marker on the cell surface. The level of markers may be determined by various methods known in the art, e.g. immuno-staining and FACS analysis, or gel electrophoresis and Western blotting.

In some embodiments, non-stimulatory myeloid cells are dendritic cells (DCs). In some embodiments, dendritic cells can be distinguished by a spikey or dendritic morphology. In one embodiment, the non-stimulatory dendritic cell is at least CD45+, HLA-DR+, CD14−, CD11c+, and BDCA1+ (also referred to as DC1 cells). In one embodiment, the non-stimulatory dendritic cell is not CD45+, HLA-DR+, CD14−, CD11c+, and BDCA3+ (also referred to as DC2 cells). In one embodiment, a dendritic cell that is CD45+, HLA-DR+, CD14−, CD11c+, and BDCA3+ is a stimulatory-myeloid cell.

In some embodiments, non-stimulatory myeloid cells are tumor associated macrophages. In some embodiments, for example in humans, the non-stimulatory tumor associated macrophages are at least CD45+, HLA-DR+, CD14+. In some embodiments the non-stimulatory tumor associated macrophages are at least CD45+, HLA-DR+, CD14−, CD11b$^+$. In some embodiments the non-stimulatory tumor associated macrophages are at least CD45$^+$, HLA-DR$^+$, CD14$^+$, CD11c$^+$. In some embodiments the non-stimulatory tumor associated macrophages are at least CD45$^+$, HLA-DR$^+$, CD14$^+$, BDCA3$^−$. In some embodiments the non-stimulatory tumor associated macrophages are at least CD45$^−$, HLA-DR$^+$, CD14$^+$, BDCA3$^−$, CD11b$^+$. In some embodiments the non-stimulatory tumor associated macrophages are at least CD45$^+$, HLA-DR$^+$, CD14$^+$, BDCA3$^−$, CD11c$^+$. In some embodiments the non-stimulatory tumor associated macrophages are at least CD45$^+$, HLA-DR$^+$, CD14$^+$, CD11b$^+$, and CD11c$^+$. In some embodiments the non-stimulatory tumor associated macrophages are at least CD45$^+$, HLA-DR$^+$, CD14$^+$, BDCA3$^−$, CD11b$^+$, and CD11c$^+$.

In some embodiments the methods and compositions of the present invention are useful for targeting TAMs and DCs in other mammals, for example in mice. In such embodiments, mice TAMs and DCs are contacted with a TREM2 antibody. In one embodiment, for example in mice, the tumor-associated macrophage is at least CD45+, HLA-DR+, CD14+, CD11b$^{high}$, and CD11c$^{low}$ (also referred to as TAM1). In one embodiment, for example in mice, tumor-associated macrophages are at least CD45+, HLA-DR+, CD14+, CD11b$^{low}$, and CD11c$^{high}$ (also referred to as TAM2). The term "CD11b$^{high}$ macrophages", as used herein, relates to macrophages expressing high levels of CD11b. The term "CD11b$^{low}$ macrophages." as used herein, relates to macrophages that express on their surface a level of CD11b that is substantially lower than that of CD11b$^{high}$ macrophages. The term "CD11$^{high}$", as used herein, relates to macrophages expressing high levels of CD11c. The term "CD11c$^{low}$ macrophages", as used herein, relates to macrophages that express on their surface a level of CD11c that is substantially lower than that of Cd11c$^{high}$ macrophages.

In some embodiments, the non-stimulatory myeloid cells of the invention include one or more of TAM and DC1 cells.

In some embodiments, for example in mice, the non-stimulatory myeloid cells of the invention include one or more of TAM1, TAM2, and DC1 cells. In such embodiments the non-stimulatory myeloid cells of the invention are contacted with a TREM2 antibody.

In some embodiments, the non-stimulatory myeloid cells are myeloid cells are intratumoral.

In some embodiments, the non-stimulatory myeloid cells are localized within the margins of the tumoral lesions or in the transformed tumor ducts, where they come into contact with cognate T-cells. In one embodiment, the localization of the non-stimulatory myeloid cell is modified, so that the cells are no longer localized at the tumor margin or are no longer in contact with T-cells.

In some embodiments, the non-stimulatory myeloid cells are in a population of immune cells comprising stimulatory myeloid cells and non-stimulatory myeloid cells. In some embodiments, the non-stimulatory myeloid cells are in a population of immune cells comprising only non-stimulatory myeloid cells. The populations of immune cells of the present invention may be pure, homogenous, heterogeneous, derived from a variety of sources (e.g. diseased tissue, tumor tissue, healthy tissue, cell banks), maintained in primary cell cultures, maintained in immortalized cultures, and/or maintained in ex vivo cultures.

In some embodiments, the non-stimulatory myeloid cells are tumor-associated macrophages.

In some embodiments, the non-stimulatory myeloid cells are dendritic cells.

In some embodiments, the non-stimulatory myeloid cells are CD45$^+$, HLA-DR$^+$, CD14$^−$, CD11c$^+$, and BDCA1$^+$. In some embodiments, the non-stimulatory myeloid cells comprise cells that are CD45$^+$, HLA-DR$^+$, CD14$^−$, CD11c$^+$, and BDCA1$^+$. In some embodiments, the non-stimulatory myeloid cells consist of cells that are CD45$^+$, HLA-DR$^+$, CD14$^−$, CD11c$^+$, and BDCA1$^+$. In some embodiments, the non-stimulatory myeloid cells consist essentially of cells that are CD45$^+$, HLA-DR$^+$, CD14$^−$, CD11c$^+$, and BDCA1.

In some embodiments, the non-stimulatory myeloid cells are CD45$^+$, HLA-DR$^+$, CD14$^+$, BDCA3$^−$. In some embodiments, the non-stimulatory myeloid cells comprise cells that are CD45$^+$, HLA-DR$^+$, CD14$^+$, BDCA3$^−$. In some embodiments, the non-stimulatory myeloid cells consist of cells that are CD45$^+$, HLA-DR$^+$, CD14$^+$, BDCA3$^-$. In some embodiments, the non-stimulatory myeloid cells consist essentially of cells that are CD45$^+$, HLA-DR$^+$, CD14$^+$, BDCA3$^-$.

In some embodiments, the non-stimulatory myeloid cells are CD45$^+$, HLA-DR$^+$, CD14$^+$, CD11b$^+$. In some embodiments, the non-stimulatory myeloid cells comprise cells that are CD45$^+$, HLA-DR$^+$, CD14$^+$, CD11b$^+$. In some embodiments, the non-stimulatory myeloid cells consist of cells that are CD45$^+$, HLA-DR$^+$, CD14$^+$, CD11b$^+$. In some embodiments, the non-stimulatory myeloid cells consist essentially of cells that are CD45$^+$, HLA-DR$^+$, CD14$^+$, CD11b$^+$.

In some embodiments, the non-stimulatory myeloid cells are CD45$^+$, HLA-DR$^+$, CD14$^+$, CD11c$^+$. In some embodiments, the non-stimulatory myeloid cells comprise cells that are CD45$^+$, HLA-DR$^+$, CD14$^+$, CD11c. In some embodiments, the non-stimulatory myeloid cells consist of cells that are CD45$^+$, HLA-DR$^+$, CD14$^+$, CD11c$^+$. In some embodiments, the non-stimulatory myeloid cells consist essentially of cells that are CD45$^+$, HLA-DR$^+$, CD14$^+$, CD11c$^+$.

In some embodiments, the non-stimulatory myeloid cells are CD45$^+$, HLA-DR$^+$, CD14$^+$, BDCA3$^-$, and CD11c$^+$. In some embodiments, the non-stimulatory myeloid cells comprise cells that are CD45$^+$, HLA-DR$^+$, CD14$^+$, BDCA3$^-$, and CD11c$^+$. In some embodiments, the non-stimulatory myeloid cells consist of cells that are CD45$^-$, HLA-DR$^-$, CD14$^-$, BDCA3$^-$, and CD11c$^+$. In some embodiments, the non-stimulatory myeloid cells consist essentially of cells that are CD45$^+$, HLA-DR$^+$, CD14$^+$, BDCA3$^-$, and C11c$^+$.

In some embodiments, the non-stimulatory myeloid cells are CD45$^+$, HLA-DR$^+$, CD14$^+$, BDCA3$^-$, CD11b$^+$. In some embodiments, the non-stimulatory myeloid cells comprise cells that are CD45$^+$, HLA-DR$^+$, CD14$^+$, BDCA3–, CD11b$^+$. In some embodiments, the non-stimulatory myeloid cells consist of cells that are CD45$^+$, HLA-DR$^+$, CD14$^+$, BDCA3$^-$, CD11b$^+$. In some embodiments, the non-stimulatory myeloid cells consist essentially of cells that are CD45$^+$, HLA-DR$^+$, CD14$^+$, BDCA3$^-$, CD11b$^+$.

In some embodiments, the non-stimulatory myeloid cells are CD45$^+$, HLA-DR$^+$, CD14$^+$, CD11b$^+$, and CD11c$^+$. In some embodiments, the non-stimulatory myeloid cells comprise cells that are CD45$^+$, HLA-DR$^+$, CD14$^+$, CD11b$^+$, and CD11c$^+$. In some embodiments, the non-stimulatory myeloid cells consist of cells that are CD45$^+$, HLA-DR$^+$, CD14$^+$, CD11b$^+$, and CD11c$^+$. In some embodiments, the non-stimulatory myeloid cells consist essentially of cells that are CD45$^+$, HLA-DR$^+$, CD14$^+$, CD11b$^+$, and CD11c$^+$.

In some embodiments, the non-stimulatory myeloid cells are CD45$^+$, HLA-DR$^+$, CD14$^+$, BDCA3$^-$, CD11b$^+$, and CD11c$^+$. In some embodiments, the non-stimulatory myeloid cells comprise cells that are CD45$^+$, HLA-DR$^+$, CD14$^+$, BDCA3$^-$, CD11b$^+$, and CD11c$^+$. In some embodiments, the non-stimulatory myeloid cells consist of cells that are CD45$^+$, HLA-DR$^+$, CD14$^+$. BDCA3$^+$, CD11b$^+$, and CD11c$^+$. In some embodiments, the non-stimulatory myeloid cells consist essentially of cells that are CD45$^+$, HLA-DR$^+$, CD14$^+$, BDCA3$^-$, CD11b$^+$, and CD11c$^+$.

In some embodiments, the non-stimulatory myeloid cells are not CD45$^+$, HLA-DR$^+$, CD14$^-$, CD11c$^+$, and BDCA3$^+$. In some embodiments, the non-stimulatory myeloid cells comprise cells that are not CD45$^+$, HLA-DR$^+$, CD14$^-$, CD11c$^+$, and BDCA3$^-$.

In some embodiments, for example in mice, the non-stimulatory myeloid cells are CD45$^+$, HLA-DR$^+$, CD14$^+$, CD11b$^{high}$, and CD11c$^{low}$. In some embodiments, for example in mice, the non-stimulatory myeloid cells comprise cells that are CD45$^+$, HLA-DR$^+$, CD14$^+$, CD11$^{high}$ and CD11c$^{low}$. In some embodiments, for example in mice, the non-stimulatory myeloid cells consist of cells that are CD45$^+$, HLA-DR$^+$, CD14$^+$, CD11b$^{high}$, and CD11c$^{low}$. In some embodiments, for example in mice, the non-stimulatory myeloid cells consist essentially of cells that are CD45$^+$, HLA-DR$^+$, CD14$^+$, CD11b$^{high}$, and CD11c$^{low}$. In such embodiments the non-stimulatory mice myeloid cells are contacted with a TREM2 antibody.

In some embodiments, for example in mice, the non-stimulatory myeloid cells are CD45$^+$. HLA-DR$^+$, CD14$^+$, CD11b$^{low}$, and CD11c$^{high}$. In some embodiments, for example in mice, the non-stimulatory myeloid cells comprise cells that are CD45$^+$, HLA-DR$^+$, CD14$^+$, CD11b$^{low}$, and CD11c$^{high}$. In some embodiments, for example in mice, the non-stimulatory myeloid cells consist of cells that are CD45$^+$, HLA-DR$^+$, CD14$^+$, CD11b$^{low}$, and CD11c$^{high}$. In some embodiments, for example in mice, the non-stimulatory myeloid cells consist essentially of cells that are CD45$^+$, HLA-DR$^+$, CD14$^+$, CD11b$^{low}$, and CD11c$^{high}$. In such embodiments the non-stimulatory mice myeloid cells are contacted with a TREM2 antibody.

In some embodiments, the non-stimulatory myeloid cells are in a cancer tissue.

In some embodiments, the population of immune cells is in a cancer tissue.

In some embodiments, the non-stimulatory cells and stimulatory myeloid cells are in a cancer tissue.

In some embodiments, the biological sample comprises a population of immune cells comprising non-stimulatory myeloid cells and stimulatory myeloid cells.

NSM cells can refer collectively to DC1, TAM1, and TAM2 cells present in tumor tissues and which may be distinguished from other cell types by their expression of NSM cell markers. For example, genes and associated proteins which are expressed or translated in greater abundance in NSM cells than SDC's may act as NSM markers. An exemplary NSM marker is CD11b. Additional exemplary NSM markers are listed in Table A. NSM cells can express TREM2, MS4A7, C5AR1, LYVE1, ABCC3, LILRB4, MRC1/CD206, SIGLEC1, STAB1, TMEM37, MERTK, and TMEM119 on their cell surface. In some aspects, NSM cells do not express at least one of KIT, CCR7, BATF3, FLT3, ZBTB46, IRF8, BTLA, MYCL1, CLEC9A, BDCA3, and XCR1.

In one embodiment, NSM cells express one or more of the NSM marker genes listed in Table A. In another embodiment, NSM cells express 2, 3, 4, 5, 6, 7, 8, 9, 10, 11, 12, 13, 14, 15, 16, 17, 18 or more of the NSM markers listed in Table D. In another embodiment. NSM cells express most or all of the NSM markers listed in Table D. In another embodiment. NSM cells are identified as expressing MRC1, MS4A7, C1QC, APOE, C1QB, C1QA, and C5AR1.

TABLE D

| SDC Markers | NSM Markers |
| --- | --- |
| KIT | C5AR1 |
| CCR7 | LYVE1 |
| BATF3 | ABCC3 |
| FLT3 | MRC1 |
| ZBTB46 | SIGLEC1 |
| IRF8 | STAB1 |
| BTLA | C1QB |
| MYCL1 | C1QA |
| CLEC9A | TMEM37 |
| BDCA3 | MERTK |
| XCR1 | C1QC |
| | TMEM119 |

TABLE D-continued

| SDC Markers | NSM Markers |
| --- | --- |
| | MS4A7 |
| | APOE |
| | CYP4F18 |
| | TREM2 |
| | TLR7 |
| | LILRB4 |

Stimulatory Myeloid Cells

As used herein, stimulatory myeloid cells (also called SDCs in certain aspects) are myeloid cells that are effective at stimulating an immune response (e.g. more effective at stimulating an anti-tumor response in a tumor microenvironment compared to non-stimulatory myeloid cells). In some embodiments, stimulatory myeloid cells are effective at presenting an antigen (e.g. a tumor antigen) to T-cells or are effective at stimulating tumor specific T-cell responses as compared to a non-stimulatory myeloid cell. In some embodiments, stimulatory myeloid cells can display an increased ability to uptake, process, and/or present tumor-associated antigens to a T cell as compared to a non-stimulatory myeloid cell. Stimulatory myeloid cells can have an increased ability to re-prime cytotoxic T lymphocytes or in some cases stimulate effective tumor-cell killing relative to non-stimulatory myeloid cells. Stimulatory myeloid cells may display higher expression of gene and cell-surface markers involved in antigen processing, antigen presentation and/or antigen co-stimulation including, without limitation, CD80, CD86, MHCI, and MHCII compared to non-stimulatory myeloid cells.

Exemplary stimulatory myeloid cell markers are listed in Table A. For example, in human SDC's, the expression of Xcr1, Clec9a, and BDCA3 (CD141) are markers of SDC identity. It will be noted that in mice, CD103 can also be used as a strong marker of SDC identity, although it is not expressed in human SDC's.

In one embodiment, SDC's are tumor infiltrating myeloid cells having dendritic cell identity and which also express one or more of the SDC markers listed in Table A. In another embodiment, SDC's are tumor infiltrating myeloid cells having dendritic cell identity and which also express two, three, four, five, six, seven, eight, nine or all of the SDC markers listed in Table A. In another embodiment, SDC's are identified as tumor infiltrating myeloid dendritic cells expressing BDCA3, KIT, CCR7, BATF3, FLT3, ZBTB46, IRF8, BTLA, MYCL1, XCR1 and CLEC9A. SDC's cells can express at least one of KIT, CCR7, BATF3, FLT3, ZBTB46, IRF8, BTLA, MYCL1, CLEC9A, BDCA3, and XCR1. In some embodiments. SDC's do not substantially express TREM2, MS4A7, C5AR1, LYVE1, ABCC3, LILRB4, MRC1/CD206, SIGLEC1, STAB1, TMEM37, MERTK, and/or TMEM119 on their cell surface. In some embodiments, SDC's do not substantially express C5AR1, LYVE1, ABCC3, MRC1, SIGLEC1, STAB1, C1QB, C1QA, TMEM37, MERTK, C1QC, TMEM119, MS4A7, APOE, CYP4F18, TREM2, TLR7, and/or LILRB4. Flow cytometry and PCR, among other art recognized assays, can be used to assess expression of a marker disclosed herein.

Stimulatory myeloid cells can be CD45$^+$, HLA-DR$^+$, CD14$^-$, CD11c$^+$, and BDCA3$^+$.

Stimulatory myeloid cells can be CD45$^+$, HLA-DR$^+$, and BDCA3$^+$. Stimulatory myeloid cells can be CD45$^+$, HLA-DR$^+$, CD14$^-$, and BDCA3$^+$. Stimulatory myeloid cells can be CD45$^+$, HLA-DR$^+$, CD11c$^+$, and BDCA3$^+$.

Proteins, Nucleotides, and Homologs

Provided herein are methods and compositions for disabling and/or detecting non-stimulatory human myeloid cells that express NSM proteins. In some embodiments, the invention is directed to disabling and/or detecting non-stimulatory myeloid cells from non-human mammalian cells that express a NSM protein homolog. For example, NSM proteins in the mouse can express a comparable restricted pattern of expression as its human homolog. Thus in one embodiment, provided herein are methods and compositions for disabling and/or detecting non-stimulatory mouse myeloid cells that express an NSM protein. Also provided herein are similar methods and compositions for disabling and/or detecting non-stimulatory cells from any individual that expresses a homolog of a NSM protein, with a similar expression pattern, which cells exhibit a comparable pattern of expression as that of the NSM protein.

NSM proteins or nucleotides can include at least one or more of C5AR1, LYVE1, ABCC3, MRC1, SIGLEC1, STAB1, C1QB, C1QA, TMEM37, MERTK, C1QC, TMEM119, MS4A7, APOE, CYP4F18, TREM2, TLR7, and LILRB4, and homologs thereof. SDC proteins or nucleotides can include at least one or more of KIT. CCR7, BATF3, FLT3, ZBTB46, IRF8, BTLA, MYCL1, CLEC9A, BDCA3, and XCR1, and homologs thereof. Cell surface NSM proteins can include at least one or more of TREM2, MS4A7, C5AR1, LYVE1, ABCC3, LILRB4, MRC1/CD206, SIGLEC1, STAB1, TMEM37, MERTK, and TMEM119. Cell surface NSM proteins can be targeted by one or more anti-TREM2 antibodies, alone or in combination. Generally NSMs are positive for NSM proteins or nucleotides and negative for SDC proteins or nucleotides; conversely SDCs are generally positive for SDC proteins or nucleotides and negative for NSM proteins or nucleotides.

The antibodies described herein comprise at least one polypeptide, though they typically comprise a dimer of a HC/LC, i.e., four polypeptides. Also described are polynucleotides encoding the polypeptides described herein. The antibodies are typically isolated.

As used herein, "isolated" means an agent (e.g., a polypeptide or polynucleotide) that has been identified and separated and/or recovered from a component of its natural cell culture environment. Contaminant components of its natural environment are materials that would interfere with diagnostic or therapeutic uses for the antibody, and may include enzymes, hormones, and other proteinaceous or non-proteinaceous solutes. Isolated also refers to an agent that has been synthetically produced, e.g., via human intervention.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and sele-nocysteine. Amino acid analogs refers to compounds that have the same basic chemical structure as a naturally occur-ring amino acid, i.e., a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having prop-erties known in the art to be characteristic of amino acids. Examples of non-naturally occurring amino acids include, but are not limited to, α-methyl amino acids (e.g. α-methyl alanine), D-amino acids, histidine-like amino acids (e.g., 2-amino-histidine, β-hydroxy-histidine, homohistidine), amino acids having an extra methylene in the side chain ("homo" amino acids), and amino acids in which a carbox-ylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing coun-terparts. Thus, the construction of peptides, etc., incorporat-ing D-amino acids can be particularly useful when greater intracellular stability is desired or required. More specifi-cally, D-peptides, etc., are resistant to endogenous pepti-dases and proteases, thereby providing improved bioavail-ability of the molecule, and prolonged lifetimes in vivo when such properties are desirable. Additionally, D-pep-tides, etc., cannot be processed efficiently for major histo-compatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Also included in the invention are polynucleotides encod-ing polypeptides of the antibodies. The term "polynucle-otide" or "nucleotide sequence" is intended to indicate a consecutive stretch of two or more nucleotide molecules. The nucleotide sequence may be of genomic. cDNA, RNA, semisynthetic or synthetic origin, or any combination thereof.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleo-tides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroami-dates, and the like). Unless otherwise indicated, a particular nucleic acid sequence also implicitly encompasses conser-vatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Conservatively modified variants" applies to both amino acid and nucleic acid sequences. With respect to particular nucleic acid sequences. "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methio-nine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables provid-ing functionally similar amino acids are known to those of ordinary skill in the art. Such conservatively modified vari-ants are in addition to and do not exclude polymorphic variants, interspecies homologs, and alleles described herein.

Conservative substitution tables providing functionally similar amino acids are known to those of ordinary skill in the art. The following eight groups each contain amino acids that are conservative substitutions for one another: 1) Ala-nine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and [0139] 8) Cysteine (C), Methionine (M) (see. e.g., Creighton, Proteins: Struc-tures and Molecular Properties (W H Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a per-centage of amino acid residues or nucleotides that are the same (i.e., about 60/o identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. Alignment for purposes of determining percent amino acid sequence identity can be achieved in various ways that are within the skill in the art, for instance, using publicly available computer software such as BLAST. BLAST-2, ALIGN, MEGALIGN (DNASTAR), CLUSTALW, CLUSTAL OMEGA, or MUSCLE software. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence described herein or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package. Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403410, respectively. Software for performing BLAST analyses is publicly available through the National Center for Biotechnology Information available at the World Wide Web at ncbi.nlm.nih.gov. The BLAST algorithm parameters W. T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see. e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, or other nucleic acids, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology-Hybridization with Nucleic Probes. "Overview of principles of hybridization and the strategy of nucleic acid assays" (1993).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. The engineered proteins are expressed and produced by standard molecular biology techniques.

By "isolated nucleic acid molecule or polynucleotide" is intended a nucleic acid molecule. DNA or RNA, which has been removed from its native environment. For example, a recombinant polynucleotide encoding a polypeptide contained in a vector is considered isolated. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts, as well as positive and negative strand forms, and double-stranded forms. Isolated polynucleotides or nucleic acids described herein, further include such molecules produced synthetically, e.g., via PCR or chemical synthesis. In addition, a polynucleotide or a nucleic acid, in certain embodiments, includes a regulatory element such as a promoter, ribosome binding site, or a transcription terminator.

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridizing preferentially to a template nucleic acid.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

A derivative, or a variant of a polypeptide is said to share "homology" or be "homologous" with the peptide if the amino acid sequences of the derivative or variant has at least 50% identity with a 100 amino acid sequence from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

In some aspects, a polypeptide comprises an amino acid sequence that is at least 80, 85, 90, 91, 92, 93, 94, 95, 96, 97, 98, 99, or 100% identical to a relevant (e.g., polypeptide and/or antibody) amino acid sequence or fragment thereof set forth in the Table(s) or accession number(s) disclosed herein. In some aspects, an isolated antibody or protein disclosed herein comprises an amino acid sequence encoded by a polynucleotide that is at least 80, 85, 90, 91, 92, 93, 94, 95, 96, 97, 98, 99, or 100% identical to a relevant nucleotide sequence or fragment thereof set forth in Table(s) or accession number(s) disclosed herein. In some aspects, a nucleotide sequence comprises a nucleotide sequence that is at least 80, 85, 90, 91, 92, 93, 94, 95, 96, 97, 98, 99, or 100% identical to a nucleotide sequence disclosed herein such as those set forth in the Table(s) or accession number(s) disclosed herein.

Pharmaceutical Compositions

The present application provides compositions comprising the antibodies including pharmaceutical compositions comprising any one or more of the antibodies described herein with one or more pharmaceutically acceptable excipients. In some embodiments the composition is sterile. The pharmaceutical compositions generally comprise an effective amount of an antibody.

These compositions can comprise, in addition to one or more of the antibodies disclosed herein, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration. e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Whether it is a polypeptide, antibody (e.g., anti-TREM2 antibody), nucleic acid, small molecule or other pharmaceutically useful compound that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc., is within the responsibility of general practitioners and other medical doctors, and typically takes account of the disorder to be treated, the condition of the individual subject, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

Methods

Methods of Preparation

Antibodies described herein can be produced using recombinant methods and compositions, e.g., as described in U.S. Pat. No. 4,816,567.

In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody) or an amino acid sequence comprising the VHH of a single domain antibody. In a further embodiment, one or more vectors (e.g., expression vectors) comprising such nucleic acid are provided. In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antigen-binding polypeptide construct, or (2) a first vector comprising a nucleic acid that encodes an amino acid sequence comprising the VL of the antigen-binding polypeptide construct and a second vector comprising a nucleic acid that encodes an amino acid sequence comprising the VH of the antigen-binding polypeptide construct. In one embodiment, the host cell is eukaryotic, e.g. a Chinese Hamster Ovary (CHO) cell, or human embryonic kidney (HEK) cell, or lymphoid cell (e.g., Y0, NS0, Sp20 cell). In one embodiment, a method of making an antibody is provided, wherein the method comprises culturing a host cell comprising nucleic acid encoding the antibody, as provided above, under conditions suitable for expression of the antibody, and optionally recovering the antibody from the host cell (or host cell culture medium).

For recombinant production of the antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

The term "substantially purified" refers to a construct described herein, or variant thereof that may be substantially or essentially free of components that normally accompany or interact with the protein as found in its naturally occurring environment, i.e. a native cell, or host cell in the case of recombinantly produced heteromultimer that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein.

When the heteromultimer or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the heteromultimer or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" heteromultimer produced by the methods described herein, has a purity level of at least about 30%, at least about 35%, at least about 40/0, at least about 45%, at least about 50%/0, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Suitable host cells for cloning or expression of antibody-encoding vectors include prokaryotic or eukaryotic cells described herein.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome. Host cells can include CHO, derivatives of CHO, NS0, Sp2O, CV-1, VERO-76, HeLa, HepG2, Per.C6, or BHK.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyruni pernix*, etc.) phylogenetic domain.

For example, antibody may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology. Vol.* 248 (B.K.C. Lo, ed., Humana Press, Totowa. N.J., 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibodies are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described. e.g., in Mather, *Biol. Reprod* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology. Vol.* 248 (B.K.C. Lo, ed., Humana Press, Totowa. N.J.), pp. 255-268 (2003).

In one embodiment, the antibodies described herein are produced in stable mammalian cells, by a method comprising: transfecting at least one stable mammalian cell with: nucleic acid encoding the antibody, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the antibody in the expressed product.

In some embodiments is the method of producing an antibody in stable mammalian cells as described herein wherein the expression product of the at least one stable mammalian cell comprises a larger percentage of the desired glycosylated antibody as compared to the monomeric heavy or light chain polypeptides, or other antibodies.

In some embodiments is the method of producing a glycosylated antibody in stable mammalian cells described herein, said method comprising identifying and purifying the desired glycosylated antibody. In some embodiments, the said identification is by one or both of liquid chromatography and mass spectrometry.

If required, the antibodies can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antibodies. For example, the bacterial proteins A and G bind to the Fc region. Likewise, the bacterial protein L binds to the Fab region of some antibodies. Purification can often be enabled by a particular fusion partner. For example, antibodies may be purified using glutathione resin if a GST fusion is employed, $Ni^{+2}$ affinity chromatography if a His-tag is employed or immobilized anti-flag antibody if a flag-tag is used. For general guidance in suitable purification techniques, see, e.g. incorporated entirely by reference Protein Purification: Principles and Practice, $3^{rd}$ Ed., Scopes, Springer-Verlag, NY, 1994, incorporated entirely by reference. The degree of purification necessary will vary depending on the use of the antibodies. In some instances no purification is necessary.

In certain embodiments the antibodies are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, antibodies described herein can be chemically synthesized using techniques known in the art (e.g., see Creighton, 1983, Proteins: Structures and Molecular Principles. W. H. Freeman & Co., N.Y. and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alanine, fluoro-amino acids, designer amino acids such as methyl amino acids, C-methyl amino acids, N-methyl amino acids, and amino acid analogs in general. Furthermore, the amino acid can be D (dextrorotary) or L (levorotary).

Methods of Use

In one aspect, the present application provides methods of contacting non-stimulatory myeloid cells with an anti-TREM2 antibody, such as a human antibody, which results in the disabling of the non-stimulatory myeloid cells.

In another aspect, the present application provides methods of contacting non-stimulatory myeloid cells with an anti-TREM2 mouse antibody, which results in the disabling of the non-stimulatory myeloid cells.

In some embodiments the non-stimulatory cells are one or more of DC1 cells, and TAM cells.

In some embodiments, the present application provides methods of disabling non-stimulatory myeloid cells, comprising contacting the non-stimulatory myeloid cells with a TREM2 antibody, thereby killing the non-stimulatory myeloid cells. Disabling refers to rendering a cell partially or completely non-functional. In some embodiments, the disabling of the non-stimulatory myeloid cells leads to inducing growth arrest in the cells. In some embodiments, the disabling of the non-stimulatory myeloid cells leads to apoptosis in the cells. In some embodiments, the disabling of the non-stimulatory cells leads to lysis of the cells, as for example by complement dependent cytotoxicity (CDC) or antibody-dependent cell cytotoxicity (ADCC). In some embodiments, the disabling of the non-stimulatory myeloid cells leads to necrosis in the cells. In some embodiments, the disabling of the non-stimulatory myeloid cells leads to inducing growth arrest in the cells. In some embodiments, the disabling of the non-stimulatory myeloid cells leads to inactivating the cells. In some embodiments, the disabling of the non-stimulatory myeloid cells leads to neutralizing the activity of a TREM2 protein in the cells. In some embodiments, the disabling of the non-stimulatory myeloid cells leads to reduction in proliferation of the cells. In some embodiments, the disabling of the non-stimulatory myeloid cells leads to differentiation of the cells. In some embodiments, the disabling of the non-stimulatory myeloid cells leads to a decrease in the cells' ability to act as inhibitory antigen presenting cells or leads to an increase in the cells' ability to act as activating antigen-presenting cells. In some embodiments, the disabling of the non-stimulatory myeloid cells leads to the mislocalization of the cells within tumor tissue or tumor microenvironment (TME). In some embodiments, the disabling of the non-stimulatory myeloid cells leads to an altered spatial organization of the cells within tumor tissue or tumor microenvironment. In some embodiments, the disabling of the non-stimulatory myeloid cells leads to an altered temporal expression of the cells within tumor tissue or TME. In some embodiments, the method further comprises removing the non-stimulatory myeloid cells.

In any and all aspects of disabling non-stimulatory myeloid cells as described herein, any increase or decrease or alteration of an aspect of characteristic(s) or function(s) is as compared to a cell not contacted with an anti-TREM2 antibody.

In another aspect, the present application provides methods of contacting non-stimulatory myeloid cells with an anti-TREM2 antibody, which results in the modulation of function of the non-stimulatory myeloid cells. The modulation can be any one or more of the following. In some embodiments the non-stimulatory cells are one or more of DC1 cells, TAM1 cells, and TAM2 cells. In some embodiments, the modulation of function leads to the disabling of non-stimulatory myeloid cells. In some embodiments, the modulation of function of the non-stimulatory myeloid cells leads to an increase in the cells' abilities to stimulate both native and activated CD8+ T-cells, for example, by increasing the ability of non-stimulatory cells to cross-present tumor antigen on MHCI molecules to naive CD8+ T-cells. In some embodiments, the modulation increases the T-cell stimulatory function of the non-stimulatory myeloid cells, including, for example, the cells' abilities to trigger T-cell receptor (TCR) signaling, T-cell proliferation, or T-cell cytokine production. In one embodiment, the survival of the non-stimulatory cell is decreased or the proliferation of the non-stimulatory cell is decreased. In one embodiment, the ratio of stimulatory myeloid cells to non-stimulatory myeloid cells is increased.

In any and all aspects of decreasing the function of non-stimulatory myeloid cells as described herein, any increase or decrease or alteration of an aspect of characteristic(s) or function(s) is as compared to a cell not contacted with an anti-TREM2 antibody.

In some embodiments, the present application provides methods of killing (also referred to as inducing cell death) non-stimulatory myeloid cells, comprising contacting the non-stimulatory myeloid cells with an anti-TREM2 antibody, thereby killing the non-stimulatory myeloid cells. In some embodiments the killing is increased relative to non-stimulatory myeloid cells that have not been contacted with an anti-TREM2 antibody. In some embodiments, the contacting induces apoptosis in the non-stimulatory myeloid cells. In some embodiments, the contacting induces apoptosis in the non-stimulatory myeloid cells. In some embodiments, the non-stimulatory myeloid cells are in a population of immune cells comprising non-stimulatory myeloid cells and stimulatory myeloid cells. In some embodiments, the method further comprises removing the non-stimulatory myeloid cells. In some embodiments, 10%-80% of the cells are killed. In some embodiments, at least 10%, 20%, 30%, 40%, 50%, 60%, 70%/o, or 80% of the cells are killed.

In some embodiments, the present application provides methods of increasing the ratio of stimulatory myeloid cells to non-stimulatory myeloid cells in a population of immune cells comprising stimulatory myeloid cells and non-stimulatory myeloid cells, comprising contacting the population of immune cells with an anti-TREM2 antibody. In some embodiments the ratio is increased relative to a population of cells that have not been contacted with an anti-TREM2 antibody. In some embodiments the ratio of DC2 cells to DC1 cells is increased. In some embodiments the ratio of DC2 cells to TAM1 cells is increased. In some embodiments the ratio of DC2 cells to TAM2 cells is increased. In some embodiments the ratio of DC2 cells to TAM1+TAM2 cells is increased. In some embodiments the ratio of DC2 cells to TAM1+DC1 cells is increased. In some embodiments the ratio of DC2 cells to DC1+TAM2 cells is increased. In some embodiments the ratio of DC2 cells to DC1+TAM1+TAM2 cells is increased. In some embodiments, at least the ratio is increased by 10%, 20%, 30%, 40%, 50%, 60%, 70%, 80%, 90%, or 100)%.

In some embodiments the ratio of stimulatory myeloid cells to non-stimulatory myeloid cells prior to contacting ranges from 0.001:1-0.1:1. In some embodiments the ratio of stimulatory myeloid cells to non-stimulatory myeloid cells following the contacting ranges from 0.1:1-100:1.

In some embodiments, the non-stimulatory myeloid cells are reduced in number. In some embodiments the stimulatory myeloid cells are DC2 cells. In some embodiments, the non-stimulatory myeloid cells are killed, for example by necrosis, or apoptosis. In some embodiments, the non-stimulatory myeloid cells are induced to undergo growth arrest. In some embodiments the non-stimulatory myeloid cells no longer proliferate. In some embodiments the spatial localization of the non-stimulatory myeloid cells is altered, and the ratio is increased in a particular region of the TME. In some embodiments the temporal expression of the non-stimulatory myeloid cells is altered, and the ratio is increased during a particular time during the development of the tumor.

In some embodiments, the contacting is in vitro. In some embodiments, the contacting is in vivo. In some particular embodiments, the contacting is in vivo in a human. In some embodiments, the contacting is effected by administering an anti-TREM2 antibody. In some embodiments, the individual receiving the antibody (such as a human) has cancer.

In another aspect, the invention provides methods of treating an immune-related condition (e.g., cancer) in an individual comprising administering to the individual an effective amount of a composition comprising an anti-TREM2 antibody. In another aspect, the invention provides methods of enhancing an immune response in an individual comprising administering to the individual an effective amount of a composition comprising an anti-TREM2 antibody. In some embodiments these methods are further provided in combination with other co-therapies such as a PDL blockade therapy, anti-PD-1 antibodies, anti-PD-L1 antibodies, anti-PD-L2 antibodies, a CTLA4 blockade therapy, anti-CTLA4 antibodies, generalized checkpoint blockade therapy in which inhibitory molecules on T cells are blocked, adoptive T-cell therapy, CAR T-cell therapy, dendritic cell or other cellular therapies, as well as conventional chemotherapies.

In some embodiments, the method further comprises determining the expression level of TREM2 protein in a biological sample from the individual. In some embodiments the biological sample includes, but is not limited to a body fluid, a tissue sample, an organ sample, urine, feces, blood, saliva, CSF and any combination thereof. In some embodiments the biological sample is derived from a tumor tissue. In some embodiments, the expression level comprises the mRNA expression level of mRNA encoding TREM2 protein. In some embodiments, the expression level of TREM2 protein comprises the protein expression level of NSM. In some embodiments the expression level of TREM2 protein is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometry, HPLC, qPCR, RT-qPCR, multiplex qPCR or RT-qPCR, RNA-seq, microarray analysis, SAGE, MassARRAY technique, and FISH, and combinations thereof.

In another aspect, the present application provides methods for determining the presence or absence of non-stimulatory myeloid cells in general, or for determining the presence or absence of particular non-stimulatory myeloid cells (for example DC1 cells, TAM1 cells, and/or TAM2 cells) comprising: contacting a population of cells comprising non-stimulatory myeloid cells with an anti-TREM2 antibody; and quantifying the number non-stimulatory myeloid cells. In another aspect, the present application provides methods for determining the presence or absence of non-stimulatory myeloid cells comprising: contacting a population of immune cells comprising non-stimulatory myeloid cells and stimulatory myeloid cells with an anti-TREM2 antibody; detecting a complex or moiety indicating the binding of the antibody to the cell and optionally quantifying the number of non-stimulatory myeloid cells in the population. In another aspect, methods of determining the relative ratio of non-stimulatory myeloid cells to stimulatory myeloid cells are provided, comprising: contacting a population of immune cells comprising non-stimulatory myeloid cells and stimulatory myeloid cells with an anti-TREM2 antibody; quantifying the number of stimulatory myeloid cells and non-stimulatory myeloid cells; and determining the relative ratio of non-stimulatory myeloid cells to stimulatory myeloid cells.

In embodiments described herein for detection and/or quantification, an anti-TREM2 antibody binds to a TREM2 protein, but does not necessarily have to affect a biological response, such as ADCC, although it may have an effect on a biological response.

In another aspect, the present invention provides methods for identifying an individual who may respond to immunotherapy (e.g. with an anti-TREM2 antibody) for the treatment of an immune-related condition (e.g. cancer) comprising: detecting the expression level of TREM2 protein in a biological sample from the individual; and determining based on the expression level of TREM2 protein, whether the individual may respond immunotherapy, wherein an elevated level of TREM2 protein in the individual relative to that in a healthy individual indicates that the individual may respond to immunotherapy. In some embodiments, these methods may also be used for diagnosing an immune-related condition (e.g. cancer) in the individual and are based the expression level of TREM2 protein, wherein an elevated level of TREM2 protein in the individual relative to that in a healthy individual indicates that the individual suffers from cancer. In some embodiments, the expression level comprises the mRNA expression level of mRNA encoding TREM2 protein. In other embodiments, the expression level of TREM2 protein comprises the protein expression level of TREM2 protein. In some embodiments the expression level of TREM2 protein is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE. MassARRAY technique, and FISH, and combinations thereof. In these embodiments, an anti-TREM2 antibody binds to the TREM2 protein, but does not necessarily have to affect a biological response, such as ADCC. In some embodiments the biological sample is derived from a tumor tissue. In some embodiments the biological sample includes, but is not limited to a body fluid, a tissue sample, an organ sample, urine, feces, blood, saliva, CSF and any combination thereof.

Also disclosed herein is a method of enhancing a subject immune response to tumors or enhancing the efficacy of immunotherapy treatments. In general, a treatment that increases the abundance of SDC's will improve subject outcome, such as recurrence-free survival time, and will enhance the efficacy of cancer immunotherapy treatments. A treatment can increase the relative or absolute abundance of SDC cells in a subject's tumor. A treatment can decrease the relative or absolute abundance of NSM cells in a subject's tumor.

Exemplary methods of the general treatment strategy include increasing the numbers of SDC's by systemic introduction of Flt3L. Another method is treatment of a subject's autologous bone-marrow or blood cells with Flt3L while simultaneously blocking CSF1. Expression, for example by retrovirus, of SDC transcription factors such as IRF8, Myc11 or BATF3 or ZBTB46 in bone-marrow or blood progenitor populations may also be used to drive SDC development. Another strategy of treatment includes the systematic elimination of NSM cells while selectively sparing the SDC. This can generate an overall favorable change in the ratio of these populations. Elimination of NSM cells may be accomplished by any means, including the administration (systemic or localized to the tumor) of antibodies against TREM2 surface proteins.

In some embodiments, SDC-enhancing treatments are applied as a therapeutic treatment to better enable the subject's native immune system in controlling or eradicating the cancer. In another embodiment, the SDC-enhancing treatments of the invention are applied in combination with a therapeutic treatment such as an immunotherapy treatment (such application being prior to, concurrent with, or after the immunotherapy treatment) wherein the SDC-enhancing treatment acts as an accessory or adjuvant treatment to increase the efficacy of the therapeutic treatment.

Enhancing an immune response encompasses increasing, maintaining, initiating, or inducing an immune response after administration of an isolated antibody that binds to TREM2 as compared to an immune response after administration of an isotype control antibody. In some embodiments, enhancing an immune response comprises increasing an immune response as compared to an isotype control antibody. In some embodiments, enhancing an immune response comprises maintaining an immune as compared to an isotype control antibody. In some embodiments, enhancing an immune response comprises initiating an immune response as compared to an isotype control antibody. In some embodiments, enhancing an immune response comprises inducing an immune response as compared to an isotype control antibody.

In some embodiments, the treatment enhances an immune response in the subject. In some embodiments, the enhanced immune response is an adaptive immune response. In some embodiments, the enhanced immune response is an innate immune response. In some embodiments, the antibody induces a memory immune response.

In some embodiments, the antibody induces increased expression of at least one cytokine or chemokine in a cell as compared to an isotype control antibody.

In some embodiments, the at least one cytokine or chemokine is selected from the group consisting of: IFN-γ, TNF-α, CXCL1, or CXCL10.

In some embodiments, the cytokine or chemokine is CXCL10.

Methods of Administration

In some embodiments, the methods provided herein are useful for the treatment of an immune-related condition in an individual. In one embodiment, the individual is a human and the antibody is a TREM2 antibody. In another embodiment, the individual is a mouse and the antibody is a TREM2 antibody.

In some embodiments, for in vivo administration of the anti-TREM2 antibodies described herein, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease or disorder to be treated, the treatment is sustained until a desired suppression of symptoms is achieved. An exemplary dosing regimen comprises administering an initial dose of an anti-TREM2 antibody of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 μg/kg to about 2 mg/kg (such as about 3 sg/kg, about 10 μg/kg, about 30 μg/kg, about 100 μg/kg, about 300 μg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-TREM2 antibody administered, can vary over time independently of the dose used.

In some embodiments, the methods provided herein (such as methods of enhancing an immune response or effecting the disabling of non-stimulatory myeloid cells) are useful for the treatment of cancer and as such an individual receiving an anti-TREM2 antibody or an anti-TREM2 antibody has cancer.

Any suitable cancer may be treated with the antibodies provided herein. The cancer can be any carcinoma, adenocarcinoma, soft tissue, sarcoma, teratomas, melanoma, leukemia, Hodgkin lymphoma, non-Hodgkin lymphoma, or brain cancer known in the medical field. In some embodiments, the cancer is a solid cancer. In some embodiments, the cancer is a liquid cancer. In some embodiments, the cancer is immunoevasive. In some embodiments, the cancer is immunoresponsive. In some embodiments, the cancer is melanoma, kidney, hepatobiliary, head-neck squamous carcinoma (HNSC), pancreatic, colon, bladder, glioblastoma, prostate, lung, breast (mammary), ovarian, gastric, kidney, bladder, esophageal, renal, melanoma, leukemia, lymphoma, or mesothelioma. In some embodiments, the cancer is colon cancer, pancreatic cancer, or breast cancer.

In some embodiments the immune-related condition is an immune-related condition associated with the expression of TREM2 protein on non-stimulatory myeloid cells (in humans) or the expression of a homolog of TREM2 protein in a non-human species. In some embodiments the immune-related condition is an immune-related condition associated with the overexpression of TREM2 protein on non-stimulatory myeloid cells, as compared to stimulatory myeloid-cells. In some embodiments the overexpression of the TREM2 mRNA or the TREM2 protein is about at least 2 fold, 5 fold, 10 fold, 25 fold, 50 fold, or 100 fold higher as compared to stimulatory myeloid cells.

In some embodiments, an antibody is administered intravenously, intramuscularly, subcutaneously, topically, orally, transdermally, intraperitoneally, intraorbitally, by implantation, by inhalation, intrathecally, intraventricularly, or intranasally. An effective amount of an anti-TREM2 antibody may be administered for the treatment of cancer. The appropriate dosage of the anti-TREM2 antibody may be determined based on the type of cancer to be treated, the type of the anti-TREM2 antibody, the severity and course of the cancer, the clinical condition of the individual, the individual's clinical history and response to the treatment, and the discretion of the attending physician.

Combination Therapies

In some embodiments, an antibody provided herein is administered with at least one additional therapeutic agent. Any suitable additional therapeutic agent may be administered with an antibody provided herein. In some embodiments, the immunotherapy selected from a checkpoint inhibitor, a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; an antigen binding protein that binds both a T cell and an antigen presenting cell; a BiTE dual antigen binding protein; a toll-like receptor ligand; a cytokine; a cytotoxic therapy; a chemotherapy; a cytostatic agent; a radiotherapy; a small molecule inhibitor; a small molecule agonist; an immunomodulator, and an epigenetic modulator, an combinations thereof.

In some embodiments, the additional therapeutic agent is an antibody. In some embodiments, the additional therapeutic agent is an antibody that binds a protein or proteins on a tumor cell surface.

For the treatment of cancer, the anti-TREM2 antibody may be combined with one or more antibodies that inhibit immune checkpoint proteins. Of particular interest are immune checkpoint proteins displayed on the surface of a tumor cell. The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279), are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

The two ligands for PD-1 are PD-1 ligand 1 (PD-L1; also known as B7-H1 and CD274) and PD-L2 (also known as B7-DC and CD273). PD-L1 is expressed on cancer cells and through binding to its receptor PD-1 on T cells it inhibits T cell activation/function. Inhibitors that block the interaction of PD-1 with its cognate ligands on the cancer cells. PD-L1 and PD-L2, can result in both increased T cell activation and function, and prevent cancer cells from evading the immune system.

In some embodiments, the immunotherapy is an agent that interferes with PD-1 and PD-L1 or PD-L2 binding. In some embodiments, the immunotherapy is an anti-PD1 antibody. In some embodiments, the immunotherapy is an anti-PD-L1 antibody. In some embodiments, the immunotherapy is an anti-PD-L2 antibody.

Various PD-1, PD-L1, and PD-L2 antibodies are known in the art. In some embodiments, the additional therapeutic agent is at least one of: Atezolizumab (PD-L1), Avelumab (PD-L1), Durvalumab (PD-L1), Nivolumab (PD-1), Pembrolizumab (PD-1), Cemiplimab (PD-1), Ipilimumab (CTLA4), Tremelimumab (CTLA4), or any combination thereof.

The additional therapeutic agent can be administered by any suitable means. In some embodiments, an antibody provided herein and the additional therapeutic agent are included in the same pharmaceutical composition. In some embodiments, an antibody provided herein and the additional therapeutic agent are included in different pharmaceutical compositions.

In embodiments where an antibody provided herein and the additional therapeutic agent are included in different pharmaceutical compositions, administration of the antibody can occur prior to, simultaneously, and/or following, administration of the additional therapeutic agent. In some embodiments, administration of an antibody provided herein and the additional therapeutic agent occur within about one month of each other. In some embodiments, administration of an antibody provided herein and the additional therapeutic agent occur within about one week of each other. In some embodiments, administration of an antibody provided herein and the additional therapeutic agent occur within about one day of each other. In some embodiments, administration of an antibody provided herein and the additional therapeutic agent occur within about twelve hours of each other. In some embodiments, administration of an antibody provided herein and the additional therapeutic agent occur within about one hour of each other.

Kits and Articles of Manufacture

The present application provides kits comprising any one or more of the antibody compositions described herein. In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials (including sealed vials).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, Biochemistry (Worth Publishers. Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ Ed. (Plenum Press) Vols A and B (1992).

Example 1: Humanization of Anti-TREM2 Antibody

Humanization of Clone #237920

A monoclonal Rat $IgG_{2B}$ Clone #237920 (R&D Systems Cat #MAB17291) specific for mouse and human TREM2 was used for sequence determination and humanization. In brief, disulfide bonds in the antibody were reduced with dithiothreitol (DTT) and free sulfhydryl groups were alkylated with iodoacetamide. The alkylated antibody was digested with sequencing-grade endoproteinases, purified using spin columns, and sequence was determined by LC-MS/MS analysis. The sequences are shown below.

| SEQ ID NO | Name | Sequence | | | | |
|---|---|---|---|---|---|---|
| 33 | Rat IgG2B clone # 237920 heavy chain | EVQLVESGGG LTNSGGSTYY AGSGYFDYWG YFPEPVTVTW VAHPASSTKV KPKDILLLSQ YNSTFRVVSA PQVYVMGPPT PVMDSDGSFF G | LVQPGRSLKL RDSVKGRFTL QGVMVTVSSA NSGALSSDVH DKKVERRDGG NAKVTCVVVD LPLQHQDWMS EQLTEQTVSL MYSKLNVERS | SCAASGFTFS SRDNAKSTLY QTTAPSVYPL TFPAVLQSGL IGHKCPTCPT VSEEEPDVQF GKEFKCKVNN TCLTSGFLPN RWDSRAPFVC | NYYMAWVRQA LQMDSLRSED APGCGDTTSS YTLTSSVTSS CHKCPVPELL SWFVNNVEVH KALPSPIEKT DIGVEWTSNG SVVHEGLHNH | PTKGLEWVAS TATYYCTREW TVTLGCLVKG TWPSQTVTCN GGPSVFLFPP TAQTQPREEQ LSKPKGLVRK HIEKNYKNTE HVEKSLSRPP |
| 34 | Rat IgG2B clone # 237920 light chain | NIVMTQSPKS TSNRFTGVPD GTKLELKRAD DGTERRDGVL SSSPVVKSFN | MSLSVGDRVT RFTGGGYGTD AAPTVSIFPP DSVTDQDSKD RNEC | MNCKASQNVG FTLTINSVQA STEQLATGGA STYSMSSTLS | NNLAWYQQKP EDAAFYYCQR SVVCLMNNFY LTKADYESHN | GQSPKLLLYY IYNSPWTFGG PRDISVKWKI LYTCEVVHKT |

The VH and VL sequences were compared to libraries of known human germline sequences on the NCBI website (http://www.ncbi.nlm.nih.gov/igblast/; Ye, J. et al. Nucleic Acids Research 41:W34-W40 (2013)). The databases used were IMGT human VH genes (F+ORF, 273 germline sequences) and IMGT human VLkappa genes (F+ORF, 74 germline sequences).

For 237920 VH, human germline IGHV3-23(allele 1) was chosen as the acceptor sequence and the human heavy chain IGHJ4(allele 1) joining region (J gene) was chosen from human joining region sequences compiled at IMGT® the international ImMunoGeneTics information System® www.imgt.org (founder and director: Marie-Paule Lefranc, Montpellier, France).

For 237920 VL, human germline IGKV1-39(allele 1) was chosen as the acceptor sequence and human light chain IGKJ2(allele 1) joining region (J gene) was chosen from human joining region sequences compiled at IMGT® the international ImMunoGeneTics information System® www.imgt.org (founder and director: Marie-Paule Lefranc, Montpellier, France).

CDRs were defined according to an Exemplary definition or the AbM definition (see the website of Dr. Andrew C. R. Martin www.bioinf.org.uk/abs/for a table comparing CDR definitions). Alteration of human germline framework (i.e., non-CDR residues in VH and VL) positions to corresponding parental murine sequence were used, e.g., to optimize binding of the humanized antibody.

Table 1A shows VL, VH, and full heavy and light chain sequences of the humanized versions of mAb 237920 that were created. 37017 is the parent humanized clone from which the other humanized versions were created via additional mutations. Table 1B shows the CDR sequences.

TABLE 1A

| SEQ ID NO | Name | Sequence |
|---|---|---|
| 1 | 37012_VH | EVQLLESGGGLVQPGGSLRLSCAASGFTFSNYYMAWVRQAPGKGLEWVSSLTNSGGSTYY ADSVKGRFTISRDNSKNTLYLQMNSLRAEDTAVYYCTREWAGSGYFDYWGQGTLVTVSS |
| 2 | 37012_VL | DIQMTQSPSSLSASVGDRVTITCKASQNVGNNLAWYQQKPGKAPKLLIYYTSNRFTGVPS RFSGSGSGTDFTLTISSLQPEDFATYYCQRIYNSPWTFGQGTKLEIK |
| 3 | 37013_VH | EVQLLESGGGLVQPGGSLRLSCAASGFTFSNYYMAWVRQAPGKGLEWVSSLTNSGGSTYY ADSVKGRFTISRDNSKNTLYLQMNSLRAEDTAVYYCTREWAGSGYFDYWGQGTLVTVSS |
| 4 | 37013_VL | DIQMTQSPSSLSASVGDRVTMTCKASQNVGNNLAWYQQKPGKAPKLLLYYTSNRFTGVPS RFSGSGSGTDFTLTISSVQPEDFATYYCQRIYNSPWTFGQGTKLELK |
| 5 | 37014_VH | EVQLLESGGGLVQPGGSLRLSCAASGFTFSNYYMAWVRQAPGKGLEWVASLTNSGGSTYY ADSVKGRFTLSRDNSKNTLYLQMNSLRAEDTAVYYCTREWAGSGYFDYWGQGTLVTVSS |
| 6 | 37014_VL | DIQMTQSPSSLSASVGDRVTITCKASQNVGNNLAWYQQKPGKAPKLLIYYTSNRFTGVPS RFSGSGSGTDFTLTISSLQPEDFATYYCQRIYNSPWTFGQGTKLEIK |
| 7 | 37017_VH | EVQLLESGGGLVQPGGSLRLSCAASGFTFSNYYMAWVRQAPGKGLEWVSSLTNSGGSTYY ADSVKGRFTISRDNSKNTLYLQMNSLRAEDTAVYYCAKEWAGSGYFDYWGQGTLVTVSS |
| 8 | 37017_VL | DIQMTQSPSSLSASVGDRVTITCKASQNVGNNLAWYQQKPGKAPKLLIYYTSNRFTGVPS RFSGSGSGTDFTLTISSLQPEDFATYYCQRIYNSPWTFGQGTKLEIK |
| 25 | Full 37012_H | EVQLLESGGGLVQPGGSLRLSCAASGFTFSNYYMAWVRQAPGKGLEWVSSLTNSGGSTYY ADSVKGRFTISRDNSKNTLYLQMNSLRAEDTAVYYCTREWAGSGYFDYWGQGTLVTVSSA STKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDEL |

TABLE 1A-continued

| SEQ ID NO | Name | Sequence |
|---|---|---|
| | | TKNQVSLTCLVKGFYPSDIAVEWESNGQPENNYKTTPPVLDSDGSFFLYSKLTVDKSRWQ QGNVFSCSVMHEALHNHYTQKSISISPGK |
| 26 | Full 37012_L | DIQMTQSPSSLSASVGDRVTITCKASQNVGNNLAWYQQKPGKAPKLLIYYTSNRFTGVPS RFSGSGSGTDFTLTISSLQPEDFATYYCQRIYNSPWTFGQGTKLEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 27 | Full 37013_H | EVQLLESGGGLVQPGGSLRLSCAASGFTFSNYYMAWVRQAPGKGLEWVSSLTNSGGSTYY ADSVKGRFTISRDNSKNTLYLQMNSLRAEDTAVYYCTREWAGSGYFDYWGQGTLVTVSSA STKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKLTVDKSRWQ QGNVFSCSVMHEALHNHYTQKSISISPGK |
| 28 | Full 37013_L | DIQMTQSPSSLSASVGDRVTMTCKASQNVGNNLAWYQQKPGKAPKLLLYYTSNRFTGVPS RFSGSGSGTDFTLTISSVQPEDFATYYCQRIYNSPWTFGQGTKLELKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 29 | Full 37014_H | EVQLLESGGGLVQPGGSLRLSCAASGFTFSNYYMAWVRQAPGKGLEWVASLTNSGGSTYY ADSVKGRFTLSRDNSKNTLYLQMNSLRAEDTAVYYCTREWAGSGYFDYWGQGTLVTVSSA STKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKLTVDKSRWQ QGNVFSCSVMHEALHNHYTQKSISISPGK |
| 30 | Full 37014_L | DIQMTQSPSSLSASVGDRVTITCKASQNVGNNLAWYQQKPGKAPKLLIYYTSNRFTGVPS RFSGSGSGTDFTLTISSLQPEDFATYYCQRIYNSPWTFGQGTKLEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 31 | Full 37017_H | EVQLLESGGGLVQPGGSLRLSCAASGFTFSNYYMAWVRQAPGKGLEWVSSLTNSGGSTYY ADSVKGRFTISRDNSKNTLYLQMNSLRAEDTAVYYCAKEWAGSGYFDYWGQGTLVTVSSA STKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKLTVDKSRWQ QGNVFSCSVMHEALHNHYTQKSISISPGK |
| 32 | Full 37017_L | DIQMTQSPSSLSASVGDRVTITCKASQNVGNNLAWYQQKPGKAPKLLIYYTSNRFTGVPS RFSGSGSGTDFTLTISSLQPEDFATYYCQRIYNSPWTFGQGTKLEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |

TABLE 1B

CDRs of humanized antibodies per the Exemplary system

| CDR | Sequence | SEQ ID NO |
|---|---|---|
| CDR-H1 | FSNYYMA | 9 |
| CDR-H2 | SLTNSGGSTY | 10 |
| CDR-H3 | EWAGSGY | 11 |
| CDR-L1 | NVGNNLA | 12 |
| CDR-L2 | YTSNRFT | 13 |
| CDR-L3 | RIYNSPW | 14 |

TABLE 1C

CDRs of humanized antibodies per the AbM system

| CDR | Sequence | SEQ ID NO |
|---|---|---|
| CDR-H1 | GFTFSNYYMA | 39 |
| CDR-H2 | SLTNSGGSTY | 40 |
| CDR-H3 | EWAGSGYFDY | 41 |
| CDR-L1 | KASQNVGNNLA | 42 |
| CDR-L2 | YTSNRFT | 43 |
| CDR-L3 | QRIYNSPWT | 44 |

Alignment of the Framework of the Humanized Antibodies

```
CDR-H1    EVQLLESGGGLVQPGGSLRLSCAASGFTFSNYYMAWVRQAPGKGLEWVSSLTNSGGSTYY 60

CDR-H2    EVQLLESGGGLVQPGGSLRLSCAASGFTFSNYYMAWVRQAPGKGLEWVSSLTNSGGSTYY 60

CDR-H3    EVQLLESGGGLVQPGGSLRLSCAASGFTFSNYYMAWVRQAPGKGLEWVASLTNSGGSTYY 60

3-23*01   EVQLLESGGGLVQPGGSLRLSCAASGFTFSSYAMSWVRQAPGKGLEWVSAISGSGGSTYY 60

CDR-H1    ADSVKGRFTISRDNSKNTLYLQMNSLRAEDTAVYYCAKEWAGSGYFDYWGQGTLVTVSS 119

CDR-H2    ADSVKGRFTISRDNSKNTLYLQMNSLRAEDTAVYYCTREWAGSGYFDYWGQGTLVTVSS 119

CDR-H3    ADSVKGRFTLSRDNSKNTLYLQMNSLRAEDTAVYYCTREWAGSGYFDYWGQGTLVTVSS 119

3-23*01   ADSVKGRFTISRDNSKNTLYLQMNSLRAEDTAVYYCAK---------WGQGTLVTVSS 109

CDR-L1    DIQMTQSPSSLSASVGDRVTITCKASQNVGNNLAWYQQKPGKAPKLLIYYTSNRFTGVPS 60

CDR-L2    DIQMTQSPSSLSASVGDRVTMTCKASQNVGNNLAWYQQKPGKAPKLLLYYTSNRFTGVPS 60

1-39*01   DIQMTQSPSSLSASVGDRVTITCRASQSISSYLNWYQQKPGKAPKLLIYAASSLQSGVPS 60

CDR-L1    RFSGSGSGTDFTLTISSLOPEDFATYYCQRIYNSPWTFGQGTKLEIK      107

CDR-L2    RFSGSGSGTDFTLTISSVQPEDFATYYCQRIYNSPWTFGQGTKLELK      107

1-39*01   RFSGSGSGTDFTLTISSLQPEDFATYYCQQSYSTP---PFGQGTKLEIK    106
```

In the VL domain, in CDRs, Asn28, Asn31, Asn32 and Asn53 have a low potential for deamidation based on sequence and conformation. Asn93 has a low to medium potential for deamidation and could show a low level of this post-translational modification. In the VH domain, Asn31 has a low potential for deamidation based on sequence and conformation. In CDR-H2 Asn53 has a medium potential for deamidation; to prevent post-translational modification, Asn53 could be altered to Gln, Ser or Ala and maintenance of binding determined experimentally. In CDR-H3 Trp100 may be solvent-exposed and have potential for oxidation, especially under stress conditions.

In-Solution Endoproteinase Digestion

In-solution endoproteinase digestions of the monoclonal antibody (mAb) were performed for mAb sequencing analysis. 50 µg of the antibody was reduced with DTT, alkylated using iodoacetamide, acetone precipitated and reconstituted in water at a concentration of 1 µg/µL. In-solution digestion of the antibody sample was performed by using 5 individual enzyme digestions: Asp-N, Chymotrypsin, Elastase, Trypsin and Pepsin following manufacturer's instructions. Samples were then lyophilized, resuspended in 0.1% TFA and purified using a C18 Zip-Tip. Samples were then dried by vacuum centrifugation and kept frozen until mass spectrometry analysis.

Mass Spectrometry

Intact Mass Measurement

The mAb sample was denatured, reduced, and acidified. The proteins were then analyzed using an Agilent 1100 HPLC connected to a Waters QToF Ultima Global mass spectrometer (LC-ESI-TOF MS). The appropriate LC-MS spectra were processed (combined, subtracted, smoothed and deconvoluted) using Waters MassLynx 4.1 software.

LC-MS/MS Analysis

The purified peptides were re-suspended in 0.1% formic acid and one half of each of the digests were analyzed on an Orbitrap analyzer (Q-Exactive, Thermo Fisher Scientific) outfitted with a nanospray source and EASY-nLC 1000 system (Thermo Fisher Scientific). Peptides were loaded onto a 50 cm (75 µm inner diameter) EASY-Spray column packed with PepMap®RSLC 2 µm C18 resin (Thermo Fisher Scientific) at a pressure of 800 Bar. Peptides were eluted at a rate of 250 nl/min using a gradient set up as 0%-30% acetonitrile in 0.1% formic acid over 60 min. Peptides were introduced by nano-electrospray ion source into the Q-Exactive mass spectrometer (Thermo Fisher Scientific). The instrument method consisted of one MS full scan (400-1600 m/z) in the Orbitrap mass analyzer with an automatic gain control (AGC) target of 1E6, maximum ion injection time of 120 ms and a resolution of 70000 followed by 10 data-dependent MS/MS scans with a resolution of 17500, an AGC target of SES, maximum ion time of 100 ms, and one microscan. The intensity threshold to trigger a MS/MS scan was set to an underfill ratio of 1.0%. Fragmentation occurred in the HCD collision cell with normalized collision energy set to 30. The dynamic exclusion was applied using a setting of 8 seconds.

Table 2 summarizes the biophysical characteristics of the humanized clones. Molecular Weight and Extinction Coefficient are estimated for the sum of the contributing protein chains in the quanternary structure. By default the calculation assumes equal and monomeric contribution from each chain. Extinction Coefficient is the predicted absorbance at 280 nm per molar protein in units of $M^{-1} cm^{-1}$. Potential post-translational modifications such as glycosylation, phosphorylation, and proteolysis are not considered in Molecular Weight or Extinction Coefficient estimates.

TABLE 2

| Antibody | Extinction Coefficient | Molecular Weight (Da) | Isoelectric Point | Titer (mg/L) |
|---|---|---|---|---|
| PI37012 | 226380 | 145004 | 8.41 | 255.9 |
| PI37013 | 226380 | 145012 | 8.41 | 249.7 |
| PI37014 | 226380 | 144972 | 8.41 | 259.9 |
| PI37017 | 226380 | 144870 | 8.45 | 198.61 |

Example 2: Production and Characterization of Anti-TREM2 Antibodies

Antibody Production and Characterization

Standard protein expression vectors were transfected into HEK293 using standard methods following which cells were grown for 7 days and harvested. In addition to HEK293, antibodies were also produced in 293 cells that were made deficient in mammalian a1,6-fucosyltransferase (FUT8) by CRISPR/Cas9 editing (Alexander Weiss, University of Toronto). Supernatant pH was adjusted with 1M Hepes pH 7.4 and sodium azide was added to prevent microbial growth. KanCap A resin was used to capture proteins and the antibodies were eluted with 50 mM Citrate pH 3.5, 100 mM NaCL after washing with PBS and PBS containing 1M sodium chloride. Immediately after elution, the solution was neutralized with 1M Tris (pH 8) containing 0.5M Arginine. Biophysical characterization was conducted on protein that was buffer exchanged to PBS using standard techniques. Protein was quantified by OD280, quantity and concentration was determined using calculated extinction coefficient. Reduced and non-reduced SDS-PAGE (Biorad criterion Tris/Glycine/SDS, 4-20%) or Perkin Elmer GXII capillary electrophoresis system, was used to determine purity and approximate molecular mass. Aggregation status was determined by HPLC, with detection at 280 nm using a Sepax Zenix-C SEC-300, 3 um, 300 Å, 4.6*150 mm size exclusion column and PBS running buffer.

Antibody Affinity Measurement Using Surface Plasmon Resonance (SPR)

Binding kinetics were determined by surface plasmon resonance using a Biacore T200 (GE Healthcare, UK) with human TREM2 His (Sino Biological, Beijing. P.R. China) or human captured on Series S CM5 chips through anti-His capture or TREM2 human IgG1 Fc fusion protein (in-house SEC purified to >95% purity) directly immobilized to chips by amine coupling. Serial dilutions of indicated antibodies were injected at 30 ul/minute for 2 minutes. PBS or system buffer was then injected at 30 ul/minute for 400 seconds to observe dissociation. Binding responses were corrected by subtraction of responses on a blank flow cell. For kinetic analysis, a 1:1 Langmuir model of global fittings of $k_{on}$ and $k_{off}$ values, was used. The $K_d$ values were determined from the ratios of $k_{on}$ and $k_f$r.

Table 3 shows antibody binding affinity to human TREM2-His measured by SPR.

TABLE 3

| Antibody | ka (1/Ms) | kd (1/s) | KD (M) | Rmax (RU) | Chi$^2$ (RU$^2$) |
|---|---|---|---|---|---|
| PI37012 | 1.70E+06 | 8.69E−03 | 5.12E−09 | 30.2053 | 1.1785 |
| PI37013 | 1.14E+06 | 5.49E−03 | 4.82E−09 | 33.8282 | 1.3772 |
| PI37014 | 5.11E+05 | 2.43E−03 | 4.74E−09 | 34.5363 | 1.3754 |

Table 4 shows antibody binding affinity to human TREM2-Fc measured by SPR.

TABLE 4

| Antibody | ka (1/Ms) | kd (1/s) | KD (M) | Rmax (RU) | Chi$^2$ (RU$^2$) |
|---|---|---|---|---|---|
| PI37012 | 4.96E+05 | 9.56E−04 | 1.93E−09 | 185.50 | 16.25 |
| Afuc P137012 | 4.47E+05 | 8.84E−04 | 1.98E−09 | 174.90 | 13.83 |
| PI37013 | 5.17E+05 | 8.88E−04 | 1.72E−09 | 190.63 | 19.07 |
| PI37014 | 4.71E+05 | 7.32E−04 | 1.55E−09 | 184.88 | 17.65 |
| PI37017 | 3.40E+05 | 6.14E−03 | 1.80E−08 | 35.05 | 4.58 |

At low ligand density (RL=500 RU), PI37017 binding kinetics to human TREM2-Fc did not result in a good fit. This data indicates that the A present at position 97 and the K present at position 98 of the sequence of SEQ ID NO:31 (clone 37017) likely causes a substantial loss of human TREM2 binding upon humanization of the rat IgG$_{2B}$ Clone

237920. Mutation of these framework residues (A97T and K98R) results in increased human TREM2 binding by the humanized clones. See, for example, clone 37012.

Example 3: Cellular Binding of Anti-TREM2 Antibodies

Cellular Binding (EC50 Measurement):

100,000 to 500,000 Expi 293 parental cells or Expi 293 cells over-expressing human or mouse TREM2 were plated in % well plates and dead cells were stained with Zombie Near Infrared (Biolegend). Titrations of indicated unconjugated antibodies were incubated with these cells within a range of 0 ug/ml to 10 ug/ml in a 1:3 dilution range across 8-10 points. Dependent on their isotype (higG1 or mIgG2a), these primary unconjugated antibodies were detected with Alexa Fluor 647 conjugated anti-human Fc or anti-mouse Fc secondary antibodies (Jackson Immunoresearch). Alexa Fluor 647 signal was measured by flow cytometry (BD Fortessa X-14, BD Biosciences). EC50 values were calculated by curve fitting signal generated from antibodies binding to over-expressing cells over background fluorescence generated from HEK293 parental cells in Graphpad Prism (Graphpad Software).

This data indicates that the A present at position 97 and the K present at position 98 of the sequence of SEQ ID NO:31 (clone 37017) likely causes a substantial loss of human TREM2 binding upon humanization of the rat IgG$_{2B}$ Clone #237920. Mutation of these framework residues (A97T and K98R) results in increased human TREM2 binding by the humanized clones. See, for example, clone 37012.

Table 5 shows half-maximal saturation binding of anti-TREM2 antibodies to cell surface TREM2.

TABLE 5

| Antibody | Cell Line | EC50 (nM) |
|---|---|---|
| 237920 | Expi-mTREM2 | 0.9 |
| 237920 | Expi-hTREM2 | 0.6 |
| PI37012 | Expi-mTREM2 | 0.5 |
| PI37012 | Expi-hTREM2 | 1.3 |
| PI37013 | Expi-mTREM2 | 1.2 |
| PI37013 | Expi-hTREM2 | 1.4 |
| PI37013 | Expi-mTREM2 | 1.2 |
| PI37014 | Expi-hTREM2 | 1.4 |
| PI37017 | Expi-mTREM2 | 3.6 |
| PI37017 | Expi-hTREM2 | 23.3 |

Example 4: PI-7012 Improves Anti-Tumor Activity in Combination with Anti-PD-1

Materials and Methods

CT26.WT (CRL-2638) cells were purchased from the American Type Culture Collection (ATCC). Antibodies for in vivo use were all tested for endotoxin and used at or below 0.2 EU/mg protein. The amino acid sequence of the anti-mouse PD-1 antibody from clone RMP1-14 (Absolute Antibody Inc. Cat #Ab00813-7.1) was determined by mass spectrometry (LC-MS/MS). A single point mutation [D265A] was introduced in the Fc region of the mouse IgG1 version of RMP1-14 antibody to eliminate binding to FcgRs, as described in the literature (Nimmerjahn and Ravetch 2005 Science 310: 1510-1512[1]). Mouse IgG1 [clone MOPC-21], and mouse IgG2a [clone C1.18.4] isotype controls were purchased from BioXCell. PI-7012 and Afuc-PI-7012 (having the CDR sequences of PI37012 and murinized with a mouse IgG2a format) were produced in Expi293 cells (Thermo Fisher Scientific) or 293/FUT8 knockout cells (University of Toronto) respectively in mouse IgG2a format and purified using MabSelect Protein A resin (GE Life Sciences). The antibodies were eluted with 0.1M citrate buffer (pH 3.0) and buffer exchanged before use.

All experimental procedures involving live animals were approved by the Institutional Animal Care and Use Committees at Murigenics. 6-8 week old female BALB/c mice were purchased from Taconic and used after one week of acclimatization to the animal facility. CT26 cells were harvested within 3 to 7 subcultures after thaw from liquid nitrogen stock and then used for in vivo experiments. Right ventro-lateral area of female Balb/C mice were shaved and prepared for injection a day in advance. On the day of tumor inoculation, the cells were harvested and used within 30 minutes. To establish subcutaneous tumors, $1 \times 10^6$ CT26 cells were implanted and mice were then monitored for tumor growth. Tumor volumes were calculated from caliper measurements of tumor dimensions using the formula $(L \times W2)/2$, where L is the longer measurement. When tumors reached an average size of 80-100 cubic mm, the mice were randomized to treatment groups as shown in Table 6:

TABLE 6

| Group | Treatment | Dose/Duration |
|-------|-----------|---------------|
| 1 | Mouse IgG2a + Mouse IgG1 | 10 mg/Kg + 5 mg/Kg i.p., q5d × 4 |
| 2 | Mouse IgG2a + Anti-PD-1 | 10 mg/Kg + 5 mg/Kg i.p., q5d × 4 |
| 3 | Anti-TREM2 [PI-7012] + Mouse IgG1 | 10 mg/Kg + 5 mg/Kg i.p., q5d × 4 |
| 4 | Anti-TREM2 [PI-7012] + Anti-PD-1 | 10 mg/Kg + 5 mg/Kg i.p., q5d × 4 |
| 5 | Anti-TREM2 [Afuc PI-7012] + Mouse IgG1 | 10 mg/Kg + 5 mg/Kg i.p., q5d × 4 |
| 6 | Anti-TREM2 [Afuc PI-7012] + Anti-PD-1 | 10 mg/Kg + 5 mg/Kg., q5d × 4 |

Tumor volumes and body weights were monitored twice per week and graphed for group comparison analyses by one-way ANOVA. Mice were euthanized when tumor volume reached about 2000 cubic mm, when body weights reduced more than 15% during the study, or for other health related concerns.
Results
We determined whether the affinity of mAb binding to certain FcgR via glycoengineering (ie, by generating afucosylated versions of the anti-TREM2 mAbs) could increase anti-tumor activity. PI-7012 and afuc-PI-7012 were tested in combination with anti-PD-1 in the CT26 tumor model. P1-7012 and afuc-PI-7012 displayed similar levels of tumor growth inhibition (79% vs 88% TGI). Treatment with afuc-PI-7012 resulted in a 30% cure rate. As seen in FIG. 1A, afuc-PI-7012 had increased anti-tumor activity when combined with anti-PD-1 than did P1-7012. The impact of afucosylation of P1-7012 on anti-tumor activity was more clearly seen in the analysis of the individual mouse tumor volumes (FIGS. 1B and 1C). This demonstrates that afucosylation of anti-TREM2 antibody provides a significant therapeutic advantage over core-fucosylated antibody.

Figure 2:
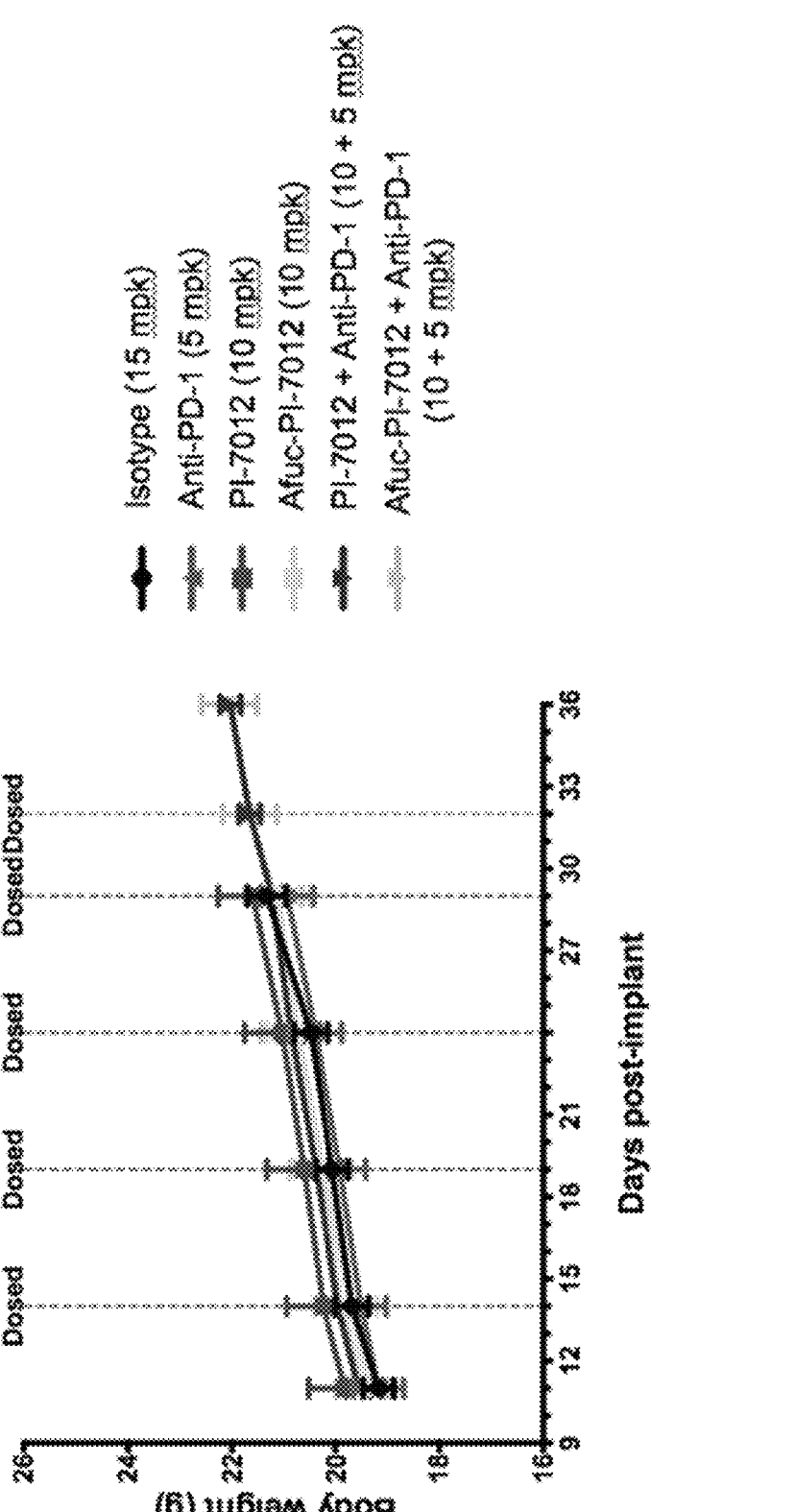
FIG. 2 No significant body weight loss with combination treatment. Ten mice in each group were treated with indicated antibodies and body weight recorded at frequent intervals. The mean body weight for each group was plotted against study days.

During the course of the study, there was no significant loss in body weight (FIG. 2) in any treatment group. Body weight loss is typically used as a surrogate measure for toxicity associated with treatment. This data indicates that short or long-term treatment with anti-TREM2 as single agent or in combination with anti-PD-1 was well-tolerated and occurred without any significant toxicity being observed.

Example 5: No Overt Toxicity Associated with Anti-TREM2 Therapy

Materials and Methods

Figure 3:
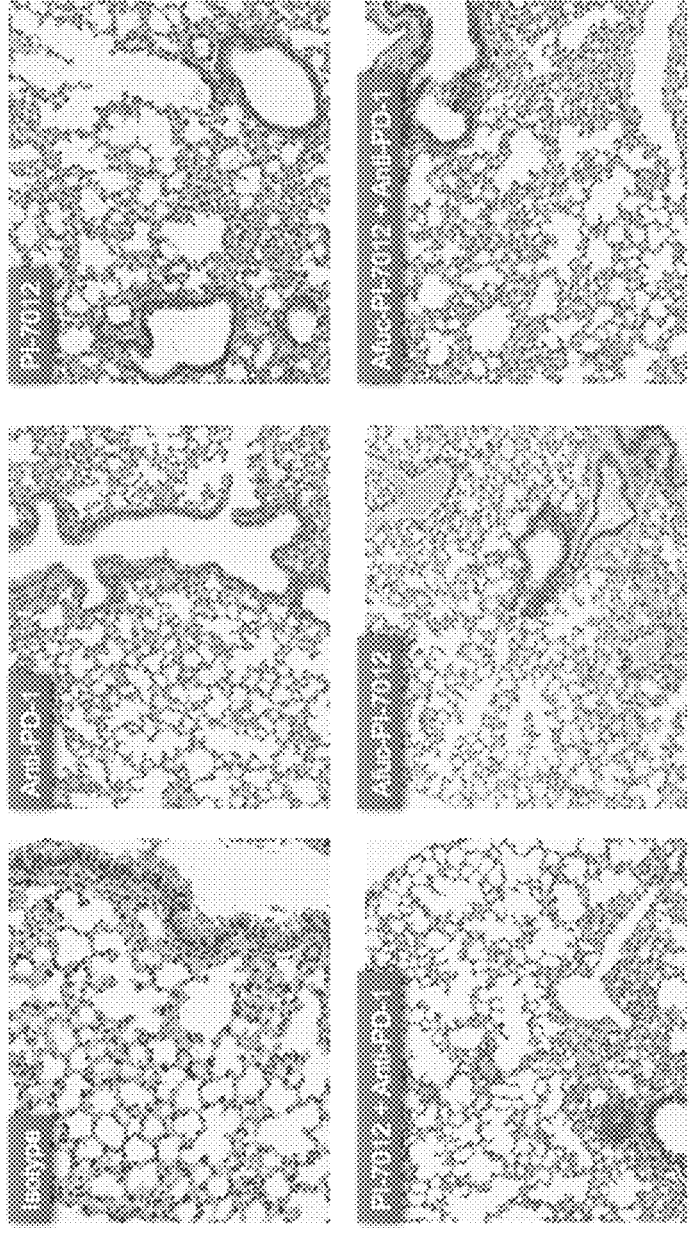
FIG. 3. In addition to H&E staining, tissues were also stained for macrophages using anti-CD68. The intracellular marker CD68 has been used widely in the literature as a reliable cytochemical marker to immunostain monocyte/macrophages in inflamed tissues and tumors. In the lung (Panel E), as well as in the other tissues analyzed, no discernable change in CD68+ macrophage numbers were observed in any of the treatment groups compared to the controls, indicating that anti-TREM2-mediated depletion occurred specifically in the TME.

Tissues (lung, liver, brain, kidney, and heart) from mice treated in the above example were preserved in 10% neutral buffered formalin for at least 24 hours, processed routinely for histology, cut at 5-6 µm, and sections were stained with hematoxylin and eosin. Stained slides were examined using low-power (40-100×) light microscopy, and an image was obtained through HistoWiz. CD68-positive cells were detected using an anti-CD68 antibody (AbD Serotec) and 8-9 fields of 40× sections were quantified using a light microscope.
Results
Gross morphological analysis by H&E staining of mouse tissues (lung, liver, heart, kidney, and brain) post-treatment did not reveal any morphological changes in the P1-7012, afuc-PI-7012, and anti-PD-1 combination treated mice, compared to isotype control treated mice (FIG. 3 shows staining of lung tissue).

Figures 4A, 4B:
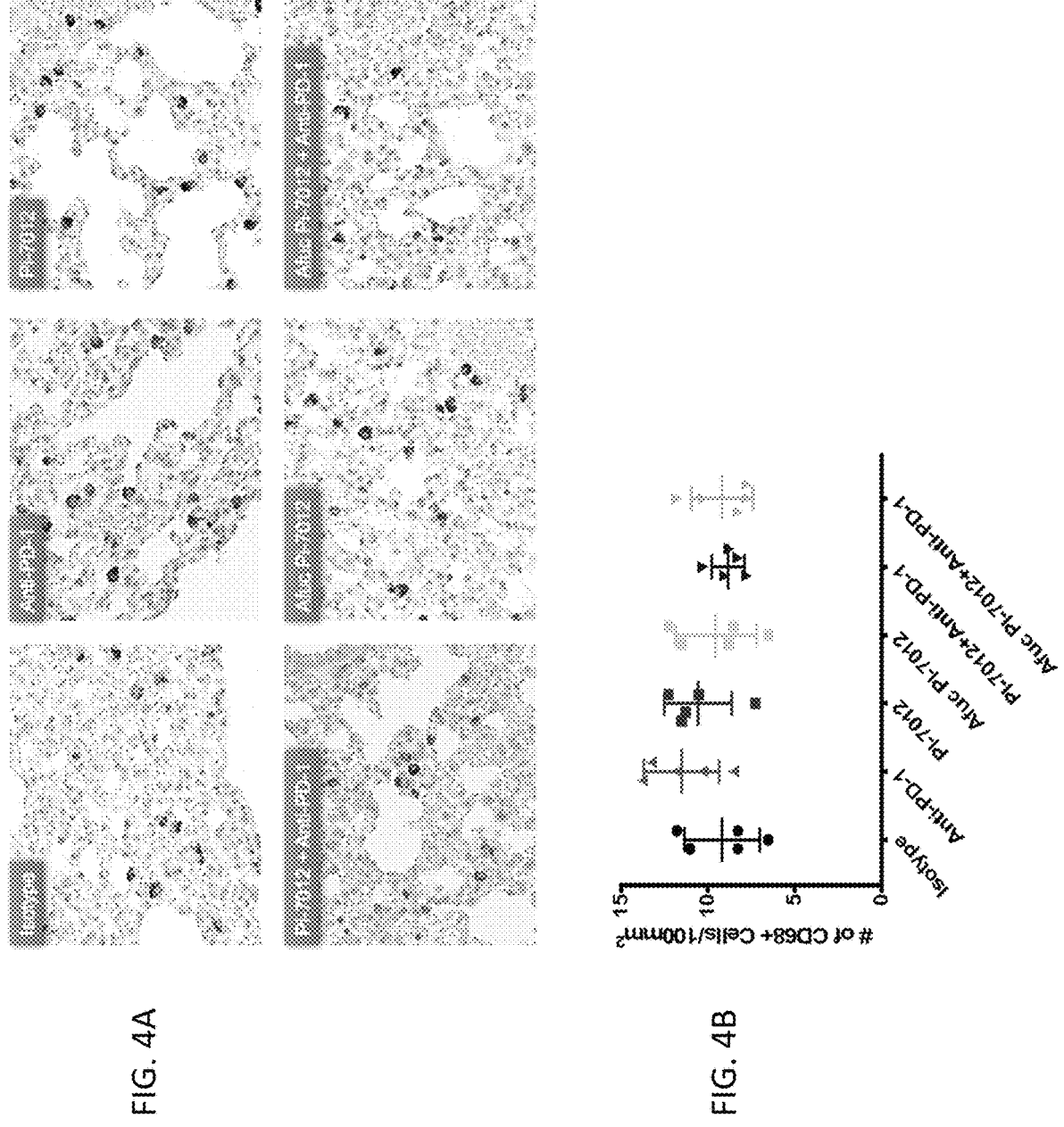
FIG. 4A shows anti-CD68 staining of FFPE lung tissue from the indicated treatment groups.
FIG. 4B shows were used for quantitation by light microscopy of eight to nine fields of each section.

In addition to H&E staining, tissues were also stained for macrophages using anti-CD68. The intracellular marker CD68 has been used widely in the literature as a reliable cytochemical marker to immunostain monocyte/macrophages in inflamed tissues and tumors. In the lung (FIG. 4A), as well as in the other tissues analyzed, no discernable change in CD68+ macrophage numbers (FIG. 4B) were observed in any of the treatment groups compared to the controls, indicating that anti-TREM2-mediated depletion occurred specifically in the TME.

Example 6: Limited TREM2 Expression in Healthy Mouse Tissues

Materials and Methods

Figure 5A:
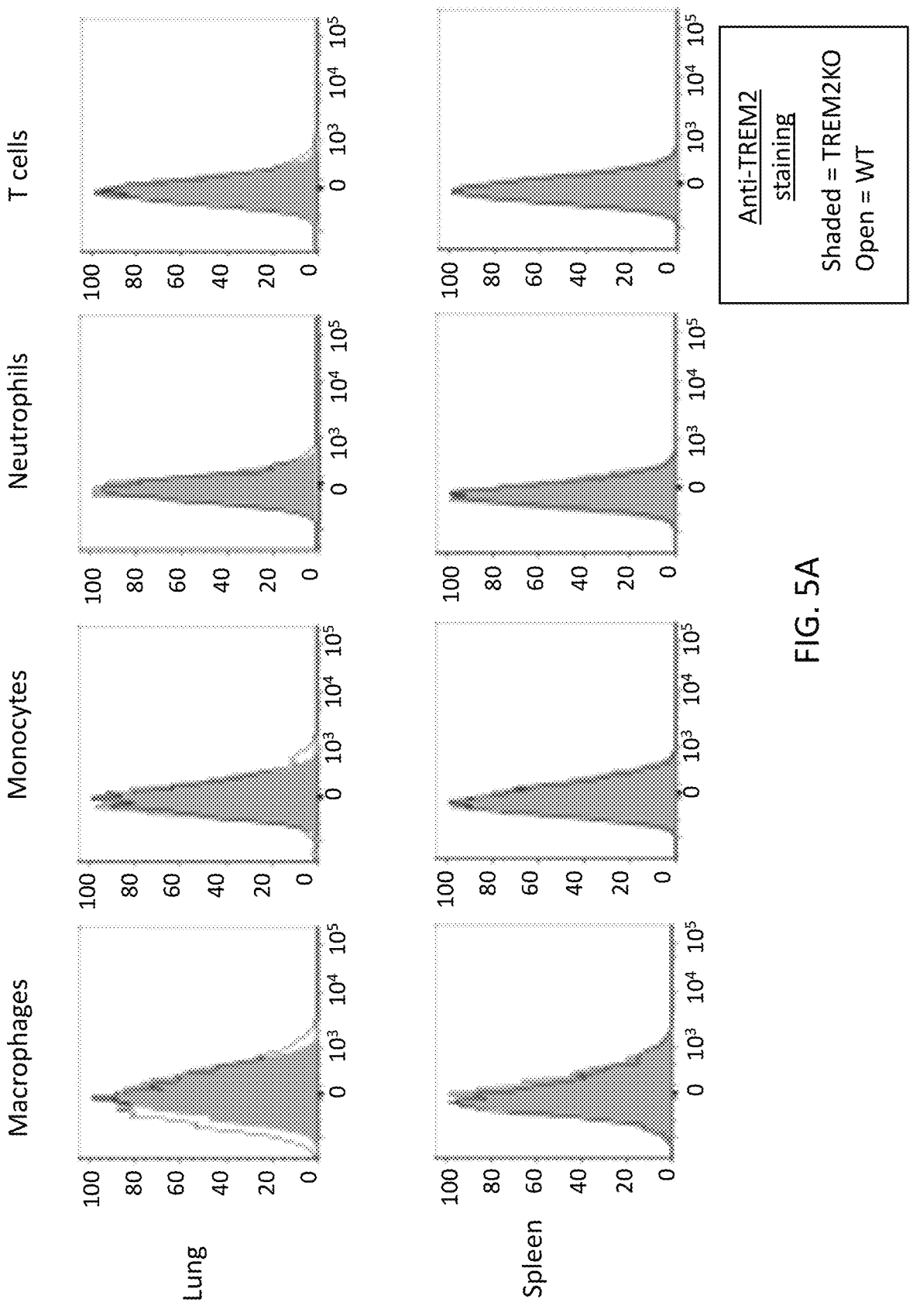
FIG. 5A shows TREM2 expression is absent or very low on cells in selected tissues.
Figure 5B:
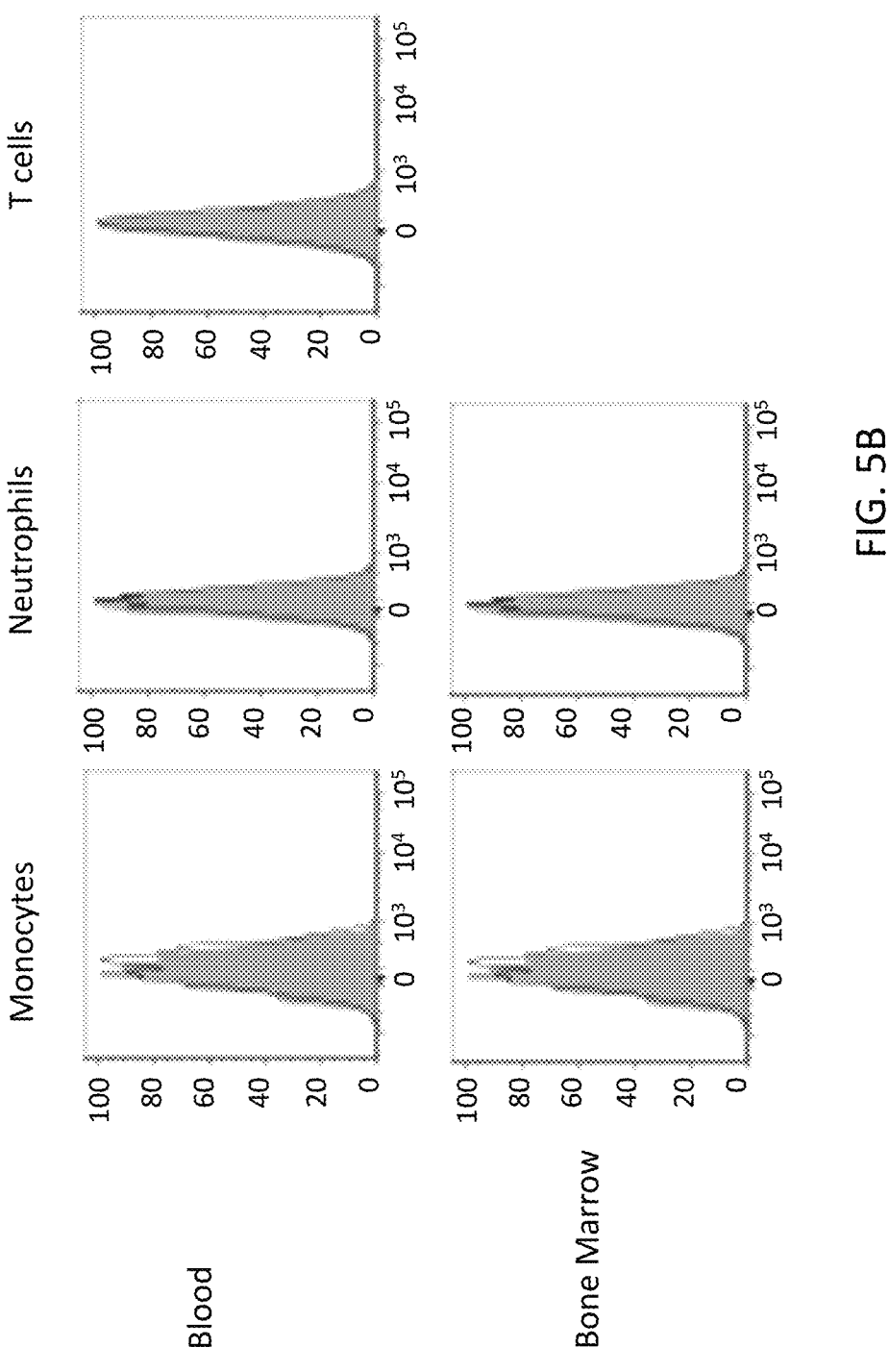
FIG. 5B shows TREM2 expression is absent or very low on cells in selected tissues. Shaded histograms are from TREM2KO and open histograms from wildtype mice. The antibody used for anti-TREM2 staining was clone 237920 from R&D Systems.

All animal studies were approved by the Murigenics Animal Studies Committee. C57BL/6J-Trem2$^{em2Adiuj}$/J (hereafter referred to as TREM2KO) and control C57BL/6J mice were from The Jackson Laboratory. Whole lungs, spleen, and bones were collected and processed immediately for flow cytometry. Blood was collected by cardiac puncture in parallel. The tissues were processed to single cell suspension using Miltenyi MACS tissue dissociation kits. Red blood cells were lysed using 1× red blood cell lysis buffer (Biolegend). Cells were stained with Fixable Viability Dye (ThermoFisher Scientific) before processing for cell surface staining. Anti-mouse immunophenotyping antibodies were diluted in FACS buffer (2% FBS, 2 mM EDTA, 1×PBS) along with Fc block and stained for 30 minutes on ice. After the staining, the cells were washed twice with FACS buffer and then fixed in 2% paraformaldehyde in PBS for 15 minutes. All data were collected on an LSR Fortessa flow cytometer (BD) or Attune flow cytometer (Thermo Fisher) and analyzed using FlowJo software. TREM2KO cell staining is shown in the shaded plots, wild type cell staining is shown in the open plots.
Results
TREM2 is expressed on activated macrophages, immature dendritic cells, osteoclasts, and microglia[2,3]. Cells expressing high levels of TREM2 are thought to participate in immune surveillance, cell-cell interactions, tissue debris clearance, and the resolution of latent inflammatory reactions.[4] The absence of TREM2 expression on these cells by gene knockdown or knockout impairs their capacity to phagocytose cellular debris and also increases their production of regulatory cytokines[5]. In a physiological setting, there is very low to no detectable expression of TREM2 in peripheral blood, spleen, liver, or lung as seen in FACS plots (FIG. 5). However, if lung or liver-resident macrophages are isolated and stained for TREM2 as pure cellular populations, TREM2 expression becomes detectable.

Example 7: TREM2 is Predominantly Expressed on Mouse TAMs

Materials and Methods

Tumor tissues were processed to isolate single cell suspension by standard methods. Briefly, tumors were finely minced with razor blades and digested in RPMI-1640 medium containing enzymes from Miltenyi MACS dissociation kits. The tumors were processed in GentleMACs as per manufacturer recommendations and incubated at 37 degrees C. for approximately 40 minutes. The digestion mixture was quenched with PBS containing 2 mM EDTA and 2% Fetal Bovine Serum. The single cell suspension was then passed through a 70 um filter and then cells were rinsed with FACS buffer. After centrifugation, the cell pellet was resuspended in FACS buffer and stained with antibody cocktail to identify tumor-associated macrophage and other immune cell populations. TREM2KO cell staining is shown in the shaded plots, wild type cell staining is shown in the open plots.

Results

Figure 6:
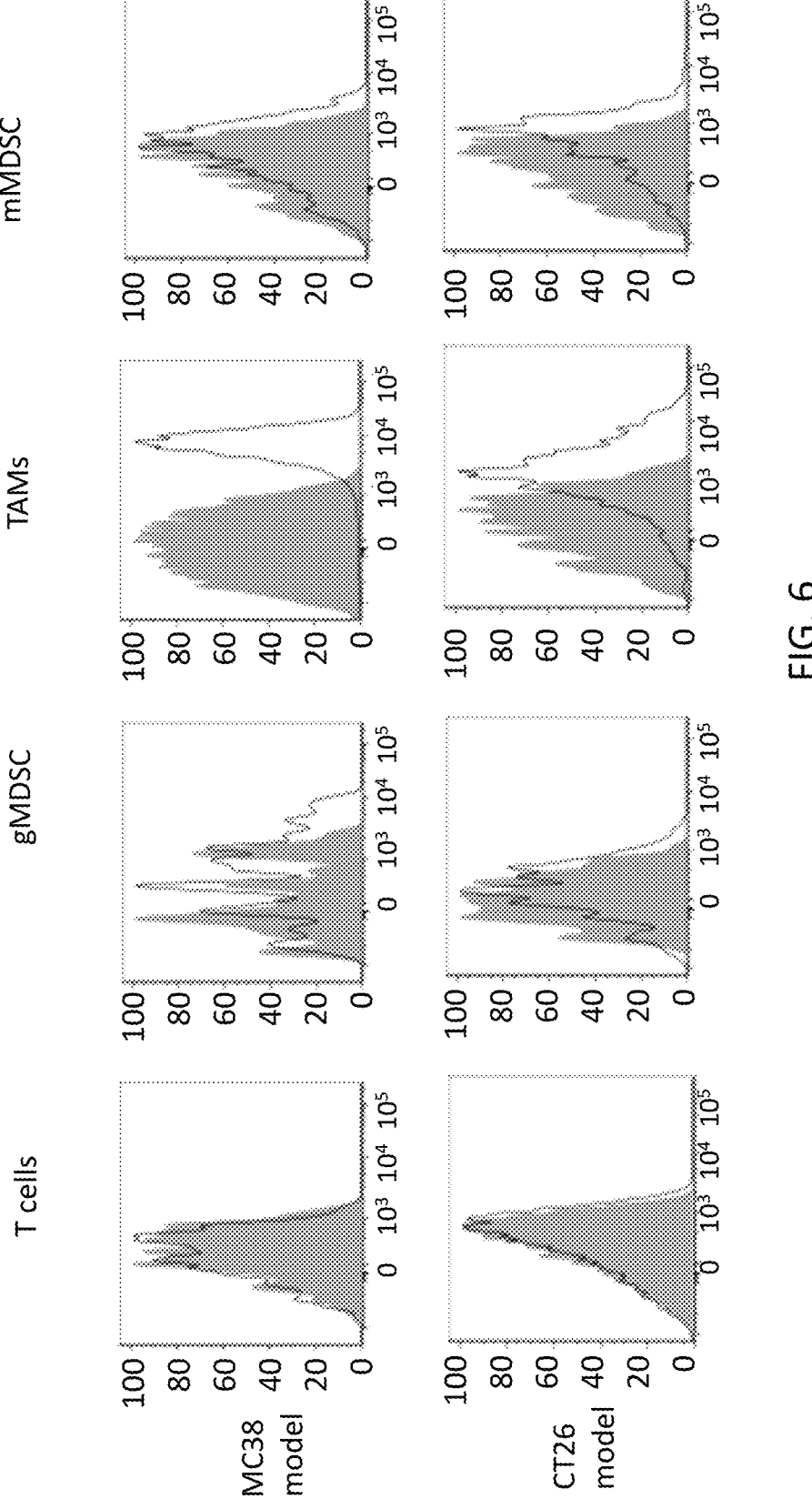
FIG. 6. Cell surface expression of TREM2 (open histogram) was significantly higher on TAMs compared to granulocytic or monocytic MDSCs within both MC38 and CT26 tumors. Lymphocytes do not express TREM2. Isotype control staining is shown in grey filled histogram.

T cells, B cells, NK cells and other non-myeloid cell populations as well as CD45-negative cells do not express detectable TREM2 expression on the cell surface. However, myeloid cell subsets including tumor-associated macrophages (TAMs) and myeloid derived suppressor cells (MDSCs) express TREM2 to varying degrees on the cell surface. Of the cell types that are positive for TREM2 in the tumor microenvironment, the density of receptor expression on TAMs was significantly higher than other cell types irrespective of the tumor origin (CT26 and MC38 shown in FIG. 6).

Example 8: Limited TREM2 Expression in Human Peripheral Blood Leukocytes

Materials and Methods

Peripheral blood mononuclear cells (PBMCs) and negatively sorted CD14+ monocytes obtained from normal human volunteers were provided by AllCells Inc. The CD14+ monocytes were differentiated in-vitro using standard protocol[5]. CD14+ monocytes were cultured in complete culture medium consisting of RPMI-1640 medium supplemented with 2 mM L-glutamine, 100 μg per ml streptomycin, 100 U per ml penicillin and 10% heat-inactivated FBS. To trigger differentiation to macrophages, 50 ng/mL M-CSF was added to the medium. Medium was supplemented every 2-3 days. After 7 days, macrophages were harvested by pipetting and the adherent cells were collected by subsequent trypsinisation. Cells were then centrifuged and resuspended in RPMI-1640 supplemented with antibiotics, 2% FBS and recombinant human IFN-g and 100 ng/mL LPS.

These macrophages were surface stained in parallel with PBMCs using standard myeloid cocktail to evaluate cell surface staining of TREM2 in cellular subsets. Cells stained with control mAb are shown in the shaded plots. Cells stained with anti-TREM2 mAb are shown in the open plots.

Results

Figure 7:
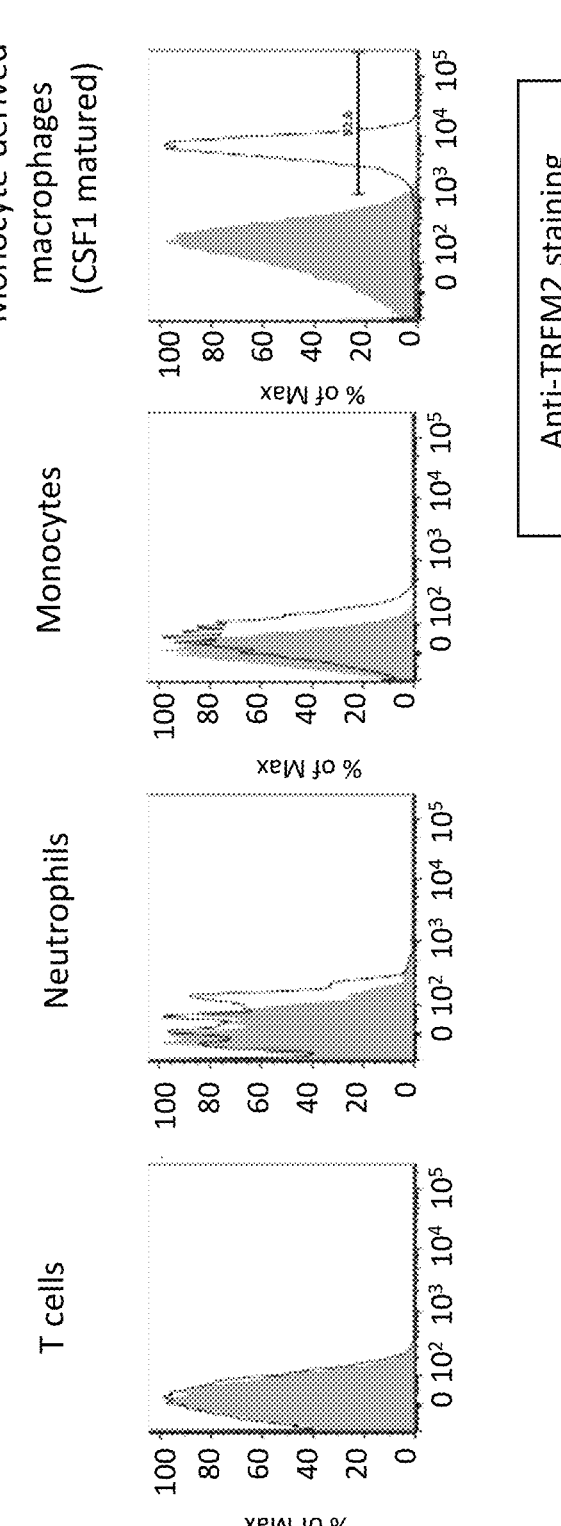
FIG. 7. Cell surface expression of TREM2 (open histogram) was significantly higher on CD14-derived macrophages compared to any PBMC subset. Human PBMC or macrophages were either surface stained for TREM2 (open histogram) or isotype control (grey histogram). PBMC subsets were discriminated as neutrophils, monocytes, or T cells using a pre-validated multicolor FACS panel.

As seen in FIG. 7, ex-vivo differentiated macrophages display significantly higher cell surface receptor density of TREM2 compared to any PBMC-based cell type evaluated. Similar to observations reported in the literature, monocytes and some neutrophils express lower levels of TREM2.

Example 9: TREM2 is Predominantly Expressed on Human TAMs

Materials and Methods

Human tumor tissues were obtained from Cooperative Human Tissue Network (CHTN). Fresh human tumor tissues were dissociated into single cell suspension using Miltenyi MACS dissociation kit and gentleMACS protocol. Single cell suspension of human tumor tissues were surface stained using pre-validate multi-color FACS panel. All data were collected on an LSR Fortessa flow cytometer (BD) or Attune flow cytometer (Thermo Fisher) and analyzed using FlowJo software. Numbers indicate the staining index for each population, defined as anti-TREM2 staining minus isotype control staining.

Results

Figure 8:
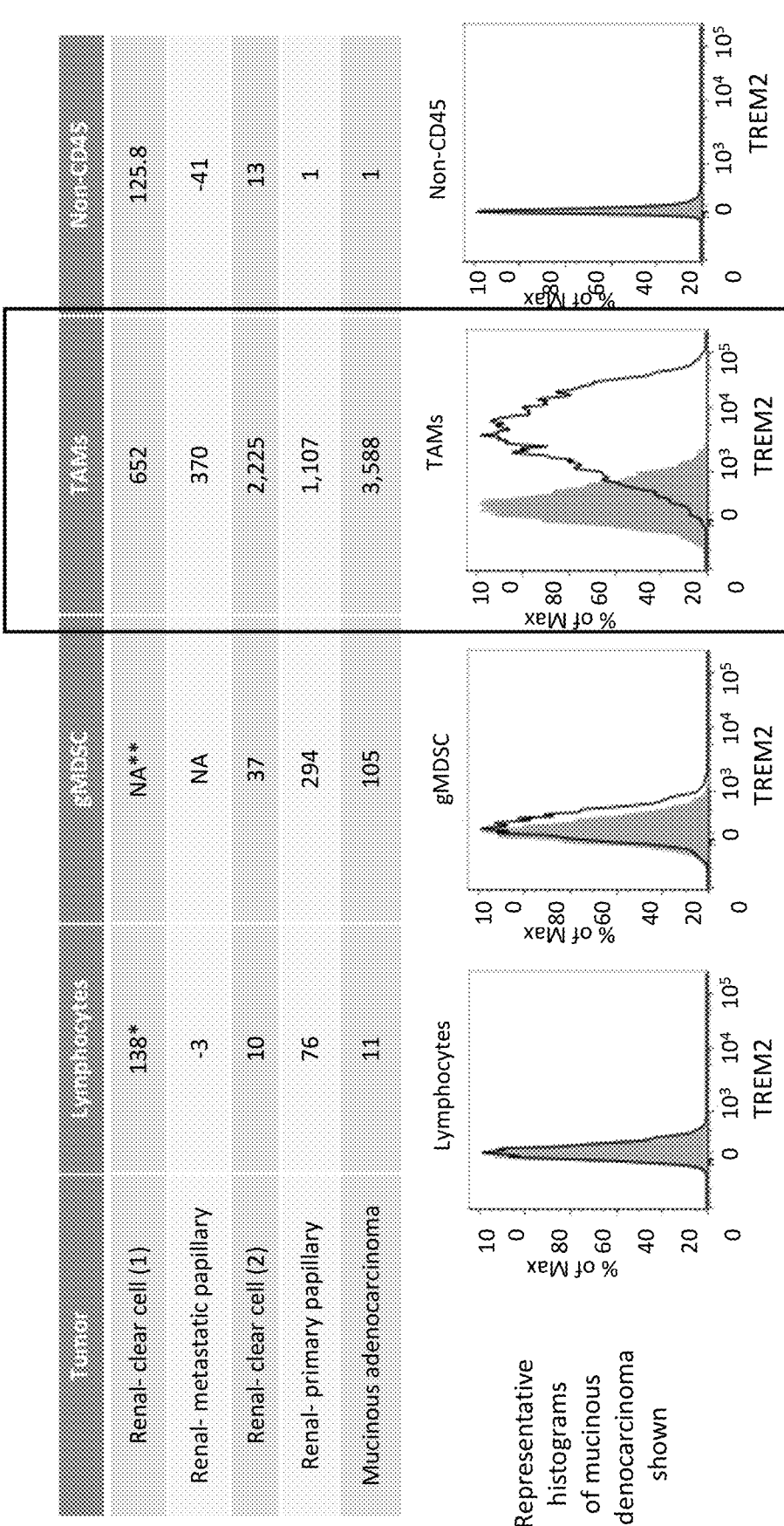
FIG. 8. Cell surface expression of TREM2 (open histogram) was significantly higher on TAMs compared to other infiltrates or non-CD45 positive cells. Single cell suspensions from human tumor tissues were either surface stained for TREM2 (open histogram) or isotype control (grey histogram). Immune and non-immune subsets were discriminated as using a pre-validated multicolor FACS panel.

Within the tumor microenvironment, TREM2 expression is differentially expressed to high levels on TAMs (FIG. 8) relative to other cells, making it a translationally relevant marker for TAMs. Representative histograms of TREM2 antibody (open) or isotype control (shaded) staining in various cell populations in mucinous adenocarcinoma are shown. Collectively, this data supports the hypothesis that TREM2 targeting agents will aid specific TAM depletion with relatively low to no collateral impact on peripheral cells or other tissue-resident immune subsets.

Example 10: Anti-Tumor Efficacy of Anti-TREM2 Antibody in Combination with Anti PD-1 in Multiple Syngeneic Tumor Models

Materials and Methods

CT26.WT (CRL-2638), Py8119 (CRL-3278), 4T1 (CRL-2539), and EMT6 (CTL-2755) cells were purchased from the American Type Culture Collection (ATCC). Panc-02 cells were used at AJES Life Sciences (Stony Brook, NY). Antibodies for in vivo use were all at or below 0.2 EU/mg protein. The amino acid sequence of the anti-mouse PD-1 antibody from clone RMP1-14 was determined by mass spectrometry (LC-MS/MS). A single point mutation, D265A, was introduced into the Fc region of the RMP1-14 antibody to eliminate binding to FcgRs. Mouse IgG1, clone MOPC-21, and mouse IgG2a, clone C1.18.4, isotype controls were purchased from BioXCell. PI-7012 and afuc-PI-7012, both as mouse IgG2a, were produced in Expi293 cells (Thermo Fisher Scientific) or 293/FUT8 knockout cells, respectively, and then purified using MabSelect Protein A resin (GE Life Sciences). The mAbs were eluted with 0.1M citrate buffer (pH 3.0) and buffer exchanged before use.

All experimental procedures involving live animals were approved by the Institutional Animal Care and Use Committees at Murigenics. Female BALB/c or C57BL/6 mice (6-8 weeks old) were purchased from Taconic or The Jackson Laboratory and used after one week of acclimatization at the animal facility. Tumor cells were harvested within 3 to 7 subcultures after thaw from liquid nitrogen stock and then used for the in vivo experiments. The right ventro-lateral area of female mice were shaved and prepared for injection a day in advance of tumor cell inoculation. On the day of tumor inoculation, the cells were harvested and used within 30 minutes. To establish subcutaneous tumors, $1 \times 10^6$ CT26, EMT6, or Panc-02 cells, or $1 \times 10^5$ 4T1 cells were implanted into appropriate strains of mice, and then the animals were monitored for tumor growth. Equal volumes of single cell suspension of Py8119 cells were mixed with Matrigel (Corning Cat #354248 or 354263) before implanting $2 \times 10^6$ cells per mouse.

Tumor volumes were calculated using caliper measurements of tumor dimensions using the formula $(L \times W2)/2$, where L is the longer measurement. When tumors reached an average size of 80-100 cubic mm, the mice were randomized to treatment groups as shown in Table 7.

Tumor volumes and body weights were monitored twice a week and graphed for group comparison analyses by one-way ANOVA. Mice were euthanized when the tumor volumes reached ~2,000 cubic mm, or when body weights were reduced more than 15% during the study.

TABLE 7

| Group | Treatment | Dose/Duration |
|---|---|---|
| 1 | Mouse IgG1 + Mouse IgG2a | 5 mg/kg + 15 mg/kg i.p., q5d × 4 |
| 2 | Anti-PD-1 + Mouse IgG2a | 5 mg/kg + 15 mg/kg i.p., q5d × 4 |
| 3 | Mouse IgG1 + Anti-TREM2 | 5 mg/kg + 15 mg/kg i.p., q5d × 4 |
| 4 | Anti-PD-1 + Anti-TREM2 | 5 mg/kg + 15 mg/kg i.p., q5d × 4 |

Results

The results are summarized in Table 8. Tumor growth inhibition (% TGI) was determined at the end of the dosing period (t) by the formula: % TGI=$(1-(Tt/T0/Ct/C0)/1-\{C0/Ct\}) \times 100$ where Tt=median tumor volume of combination-treated at time t, T0=median tumor volume of combination-treated at time 0, Ct=median tumor volume of isotype control at time t and C0=median tumor volume of isotype-treated at time 0 (before start of treatment).

TABLE 8

| Model | Strain | Activity |
|---|---|---|
| CT26 [CRC] | BALB/c | ~50-85% TGI in CT26 upon treatment in combination with anti-PD-1, as well as 40-60% Complete Response |
| Py8119 [TNBC] | C57BL/6 | ~56% TGI in combination with anti-PD-1 |
| 4T1 [TNBC] | BALB/c | ~23% TGI in combination with anti-PD-1 |
| EMT6 [Mammary] | BALB/c | ~63% TGI in combination with anti-PD-1 and 20% Complete Response |
| Panc02 [Pancreatic] | C57BL/6 | ~63% TGI in combination with anti-PD-1 |

Figure 9A:
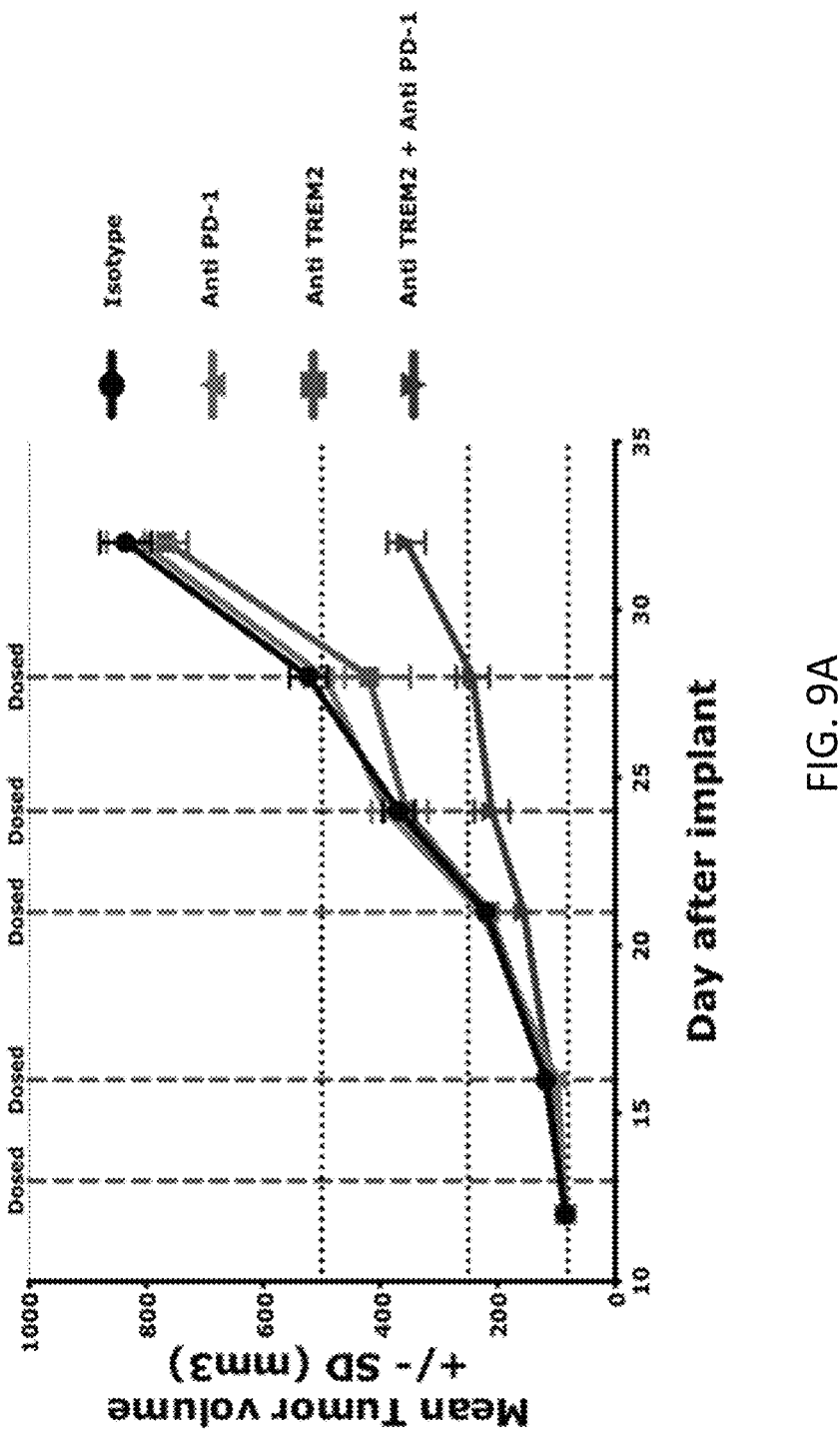
FIG. 9A shows anti-TREM2 mAb afuc-PI7012 combined with anti-PD-1 mAb resulted in significant anti-tumor activity in the Panc-02 pancreatic tumor model. Tumor volumes were tracked over time in female C57BL/6J mice implanted with Panc-02 tumor cells and treated with the indicated mAbs. The Y axis represents mean+/−standard deviation of the average tumor volumes of 10 mice in each group.
Figure 9C:
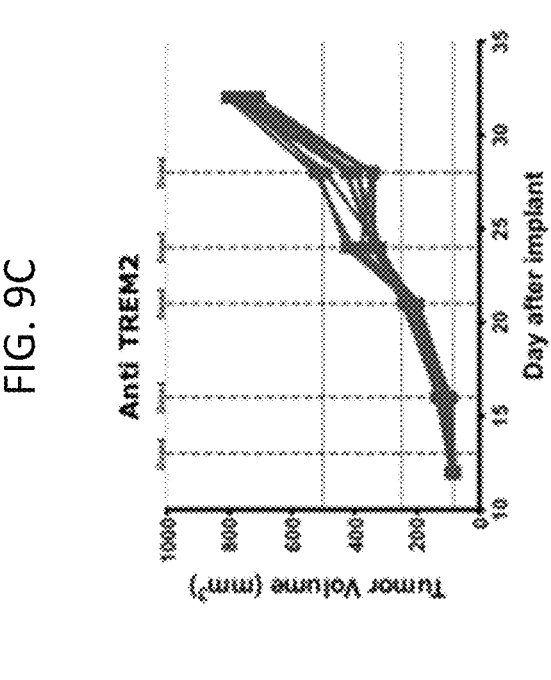
FIG. 9C shows tumor volumes from individual animals treated with anti-TREM2 mAb afuc-PI7012.
Figure 9E:
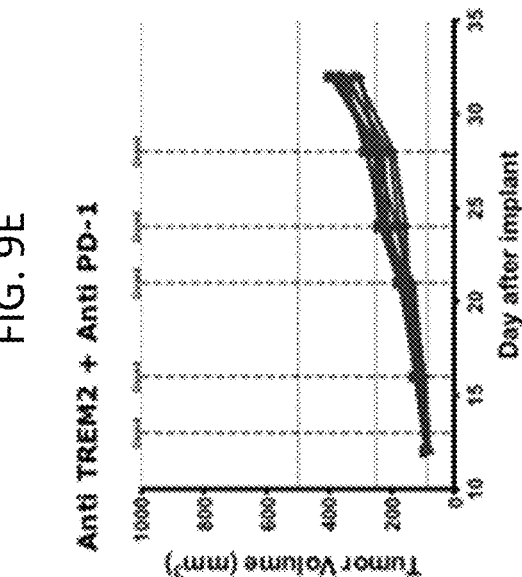
FIG. 9E shows tumor volumes from individual animals treated with anti-TREM2 mAb afuc-PI7012 and anti-PD-1.
Figure 9B:
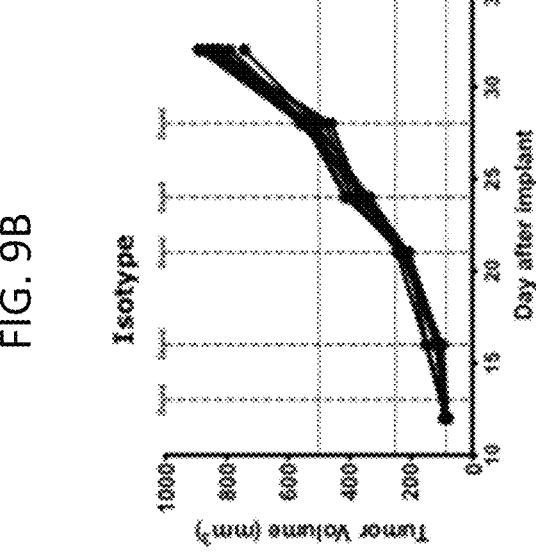
FIG. 9B shows tumor volumes from individual animals treated with isotype control mAb.

FIG. 9A-F show the anti-tumor activity of anti-TREM2 PI-7012 or afuc-PI7012 in combination with anti-PD-1 in multiple syngeneic mouse tumor models. Anti-TREM2 mAb afuc-PI7012 combined with anti-PD-1 mAb results in significant anti-tumor activity in the Panc-02 pancreatic tumor model. FIG. 9A shows the mean+/-standard deviation of the average tumor volumes of 10 mice in each group. FIGS. 9B, 9C, 9D, and 9E show the tumor volumes from individual animals in each treatment group over time. FIG. 9F shows the statistical analysis of the group average tumor volumes on day 32 after implant. Differences in tumor volumes between groups were evaluated using the statistical analyses available in the Graph Pad Prism software. One-way ANOVA followed by Sidak's multiple comparison test was performed on the study data.

Figure 9D:
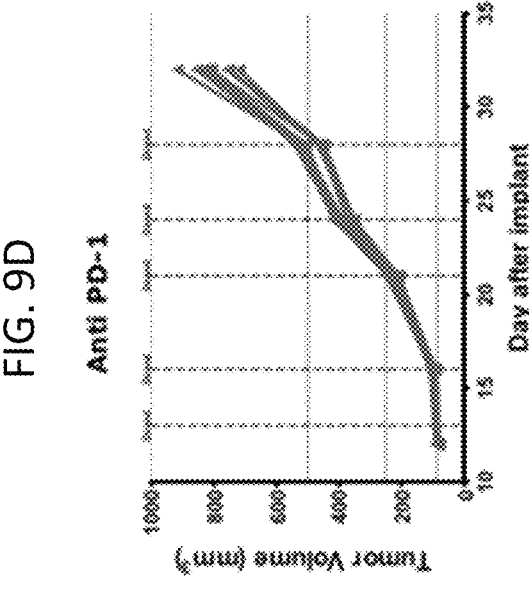
FIG. 9D shows tumor volumes from individual animals treated with anti-PD-1.
Figure 9F:
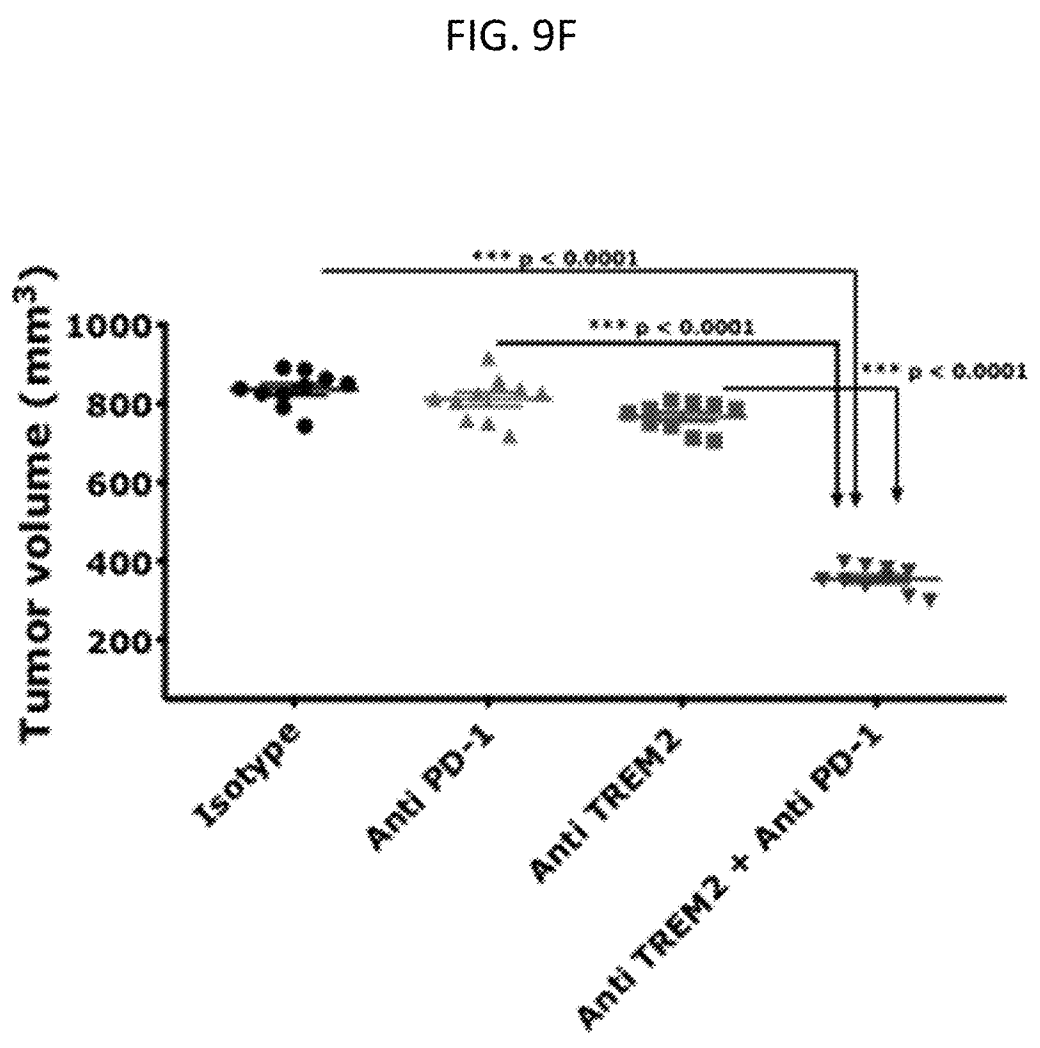

As seen in FIGS. 9A and 9D, the subcutaneous Panc-02 tumor is not responsive to an anti PD-1 mAb single agent immune checkpoint blockade therapy, or to anti-TREM2 mAb afuc-PI-7012 therapy alone. However, the combination treatment of Panc-02 tumor bearing animals with anti-TREM2 mAb afuc-PI-7012 and anti-PD-1 mAbs resulted in significant tumor growth inhibition.

The combination therapeutic strategy of myeloid-tuning along with immune checkpoint-mediated reversal of CD8 T-cell exhaustion was tested in multiple syngeneic tumor models. As shown in Table 8, the combination of anti-TREM2 and anti-PD-1 mAbs resulted in significant tumor growth inhibition, as well as complete regression in several of the tumor models tested. It is important to note that these syngeneic models were grown in two different mouse strain backgrounds (prototypical Th-1 C57BL/6 and Th-2 BALB/c strains) which are known to have significant differences in the composition of the immune infiltrates in tumors grown in these strains in vivo.

Example 11: Long-Term, Anti-Tumor Immune Memory is Elicited in Mice Responding to Anti-TREM2 mAb Plus Anti PD-1 mAb Combination Treatment Materials and Methods BALB/c mice that were tumor-free from previous studies after the anti-TREM2 mAb plus anti-PD-1 mAb treatment described in Example 9 were re-challenged three months later with $1 \times 10^6$ CT26 tumor cells. Tumor volume was measured for 25 days post implant. Age-matched treatment naïve mice received equivalent number of CT26 cells and tracked for tumor growth during the study period. No additional treatment was provided to the mice during the study period.

Results

Figure 10:
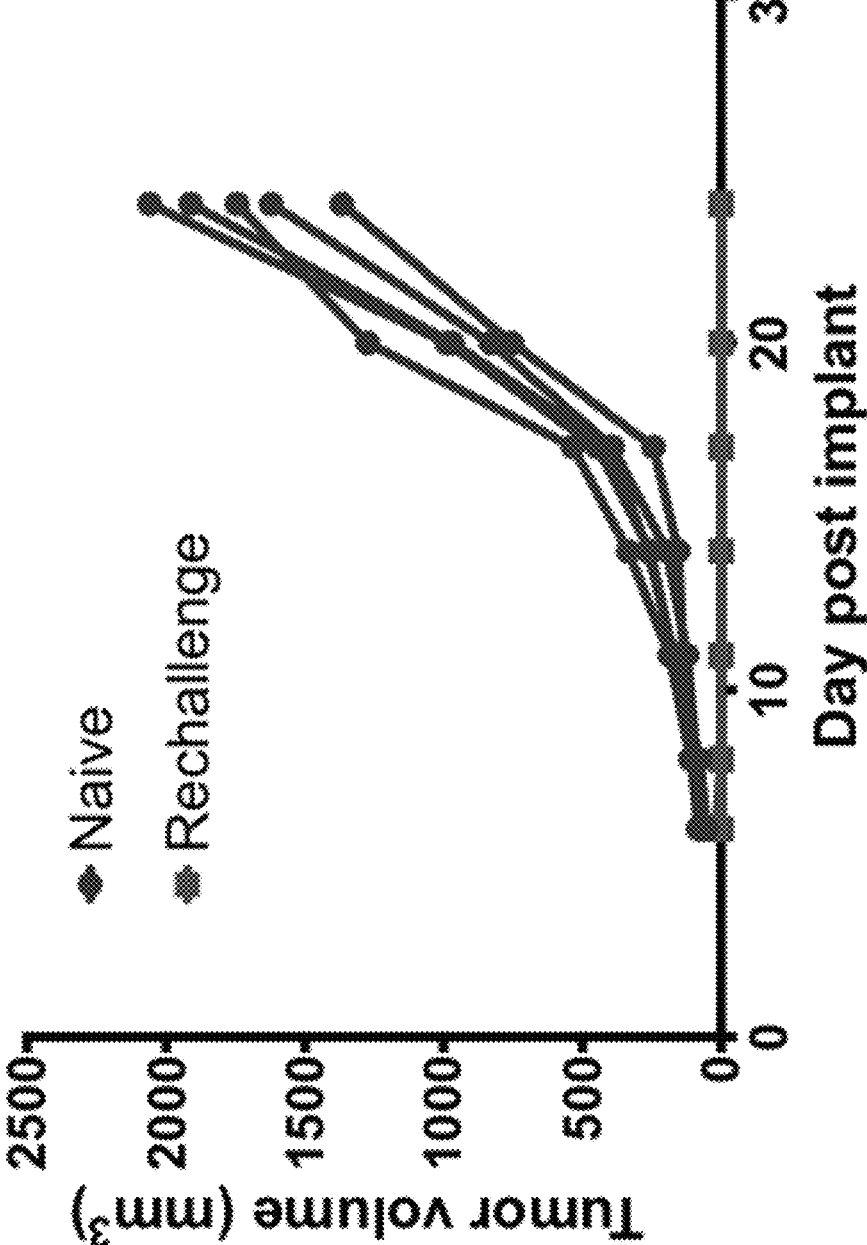
FIG. 10. Tumor-free BALB/c mice after anti-TREM2 mAb plus anti-PD-1 mAb treatment were re-challenged three months later with CT26 tumor cells (square symbols). Age-matched treatment naïve mice (round symbols) received equivalent number of CT26 cells and tracked for tumor growth during the study period. No additional treatment was provided to the mice during the study period.

Mice that were cured of their CT26 tumors following treatment with the combination of anti-TREM2 mAb afuc-PI-7012 and anti-PD-1 mAb established an effective anti-tumor memory response (FIG. 10). Cured mice were able to reject any new tumor growth even in the absence of additional therapy, indicating long-term immune memory against the original, implanted tumor. This form of long-term immune memory utilizes maintenance of a vigorous CD8+ effector memory response.

Example 12: Anti-Tumor Efficacy of Anti-TREM2 Antibody in the IDS Ovarian Tumor Model Materials and Methods Antibodies for in vivo use were all tested for endotoxin and used at or below 0.2 EU/mg protein. Anti-PD-1 (clone RMP1-14) was purchased from Absolute Antibody Inc or recombinantly produced as mouse IgG1 D265A format at Pionyr. Mouse IgG1 (clone MOPC-21) and mouse IgG2a (clone C1.18.4) isotype controls were purchased from BioX-Cell or recombinantly made in HEK293 cells at Pionyr. Chimeric mouse IgG2a version of anti-TREM2 antibody (PI-7012) was produced in HEK293 cells at Pionyr and evaluated for monodispersity and purity by SEC and CE-SDS as well as endotoxin tested.

All experimental procedures involving live animals were approved by the Institutional Animal Care and Use Committees of AJES Life Sciences LLC. 6-8 weeks old female B6(Cg)-Tyrc-2J/J or B6-albino mice were purchased from The Jackson Laboratory and used after one week of acclimatization to the animal facility. Mouse ovarian surface epithelial cells overexpressing firefly luciferase known as ID8-Luc (AJES Life Sciences LLC, Stony Brook, NY) were harvested within 3 to 7 subcultures after thaw from liquid nitrogen stock and used for in-vivo experiments. On the day of tumor inoculation, the cells were harvested and used within 45 minutes. To establish intraperitoneal tumors, $5\times10^6$ ID8-Luc cells were injected into the lower right abdominal wall. All mice were imaged for in-vivo luciferase activity 20 days following injection for recruitment to the study. Forty tumor-bearing animals were recruited to the study based on average luminescence reading as a surrogate for tumor burden. Four treatment groups were randomly assigned with 10 animals such that the average tumor radiance (p/s/cm2/sr) for each group was $4.7\times10^4$. Tumor-bearing animals were treated with indicated antibodies intraperitoneally every 5 days and the luminescence images were captured weekly. Mice were injected intraperitoneally with 0.2 mL of 15 mg/mL D-luciferin (Promega). Ten minutes after D-luciferin injection, the mice were imaged in an instrument equipped with a charge-coupled device camera (IVIS, Xenogen, Alameda, CA). Data was analyzed with Living Image software (Xenogen) and presented as tumor radiance (p/s/cm2/sr) for a region of interest covering the peritoneum.

Results

Figure 11:
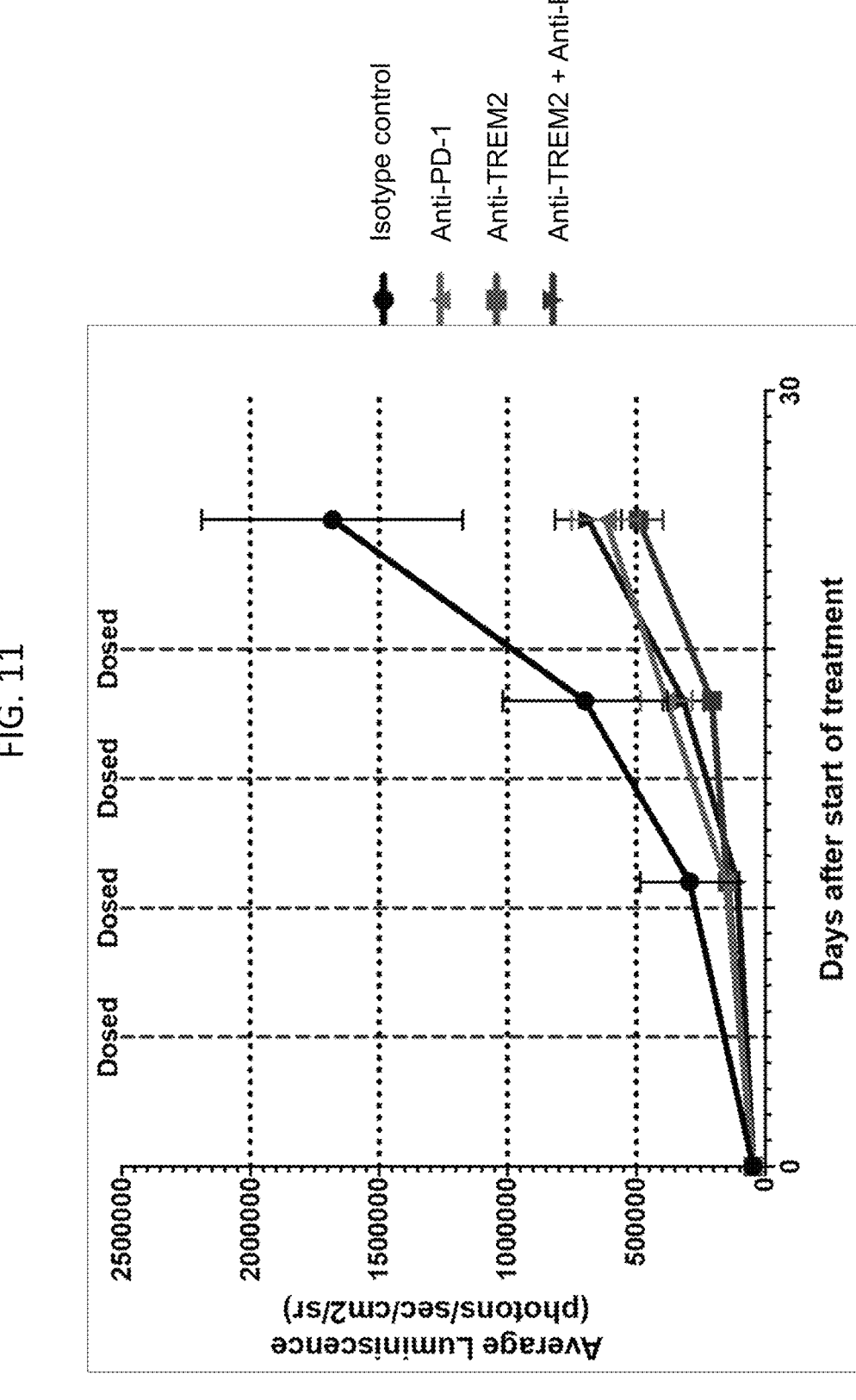
FIG. 11 shows anti-TREM2 mAb afuc-PI7012 combined with anti-PD-1 mAb resulted in significant anti-tumor activity in the ID8 ovarian tumor model. The luminescence of tumor cells was tracked over time in female C57BL/6J mice implanted with ID8 tumor cells and treated with the indicated mAbs. The Y axis represents mean+/−standard deviation of the average tumor luminescence of 10 mice in each group.

As shown in FIG. 11, anti-TREM2 antibody treatment alone resulted in a significant reduction in tumor burden, indicating that TREM2 antibody treatment has monotherapeutic efficacy. Anti-PD1 antibody treatment resulted in comparable tumor burden reduction, as did the combination of anti-TREM2 antibody and anti-PD1 antibody.

Example 13: TREM2 Expression Increases with Disease Grade in Multiple Cancers

Materials and Methods

Tissue Acquisition

Tumor microarrays (TMAs) from different tumor indications and across disease grades were purchased from Reveal Biosciences (San Diego, CA) and included 48 patient cases in duplicates or >96 single cases as 2 mm cores. The TMAs at Reveal Biosciences were made by acquiring tissues that were fixed in 10% neutral buffer formalin for 24 hours and processed using identical SOPs. Sections were picked onto Superfrost Plus or Startfrost Adhesive slides and all TMAs were cut fresh in 4 μm sections upon ordering and stored at 4° C.

TREM2 IHC Staining

The IHC assay to detect TREM2 positive cells in formalin fixed paraffin embedded (FFPE) tissues was standardized for all the TMAs staining. Slides were first baked in a 60° C. oven for 45 minutes followed by deparaffinization three times in xylene for 5 minutes each. Slides were then rehydrated in a series of ethanol gradient, from 100% to 70% ethanol, and washed at the end with distilled water. The decloaking pressure chamber (Biocare) was used for the heat-induced antigen retrieval step in sodium citrate buffer at pH 6.0 (Sigma, C9999), for 15 minutes at 110° C. To block endogenous peroxidase activity, a blocker solution (Vector Labs) was applied on the slides for 15 minutes followed by rinsing in PBS buffer containing Tween (Alfa Aesar-J63596). Non-specific binding was blocked by incubating the tissue sections with a blocking solution containing goat serum (Vector Labs) overnight at 4° C. PIT2D, also known as the recombinant anti-TREM2 antibody clone EPR20243 (Abcam, ab209814) was used as the primary antibody for 60 minutes at room temperature, at a concentration of 5 μg/ml in PBS. Slides were then washed twice in PBS-Tween for 5 minutes each, followed by a 20 minutes incubation in HRP-polymer conjugated anti-rabbit secondary antibody at 1:500 dilution (MP-7500 detection kit from Vector Labs). Slides were washed twice with PBS-Tween for 5 minutes each before proceeding to the detection step. The DAB substrate was prepared according to the manufacturer's instructions (Abcam, ab64238) and applied to the slides for 3 minutes, followed by rinsing thoroughly in distilled water. Hematoxylin was used to counterstain the slides for 30 seconds followed by rinsing in running water, dehydration in series of ethanol gradient from 70% to 100% ethanol, and drying in xylene. The stained slides were finally mounted in media and topped with coverslips for overnight drying.

Imaging and Scoring

The TMA slides were imaged on the Vectra microscope (Perkin Elmer-Akoya Biosciences) using the Bright field setting. After whole slide scanning at 10×, quantification of the TREM2+ cells was assessed using the following IHC scoring system: 0: no staining in the stromal area within the core, 1:~25% of positive cells in the stromal area within the core, 2: 50% of positive cells in the stromal area within the core, 3: 75% of positive cells in the stromal area within the core. Percentages of positive cells that fell between these groups were scored as 0.5 (~12%), 1.5 (~37.5%), 2.5 (~62.5%), and 3.5% (90%). The intensity of the TREM2 staining was determined as low (score of 1), moderate (score of 2), and strong (score of 3). Lost or folded cores with more than half of the area distorted were removed from the analysis and not scored. Each core was checked by 2 operators at the same time and the score for each patient case (duplicate cores were averaged when available) was plotted in the prism file. Lost or folded cores with more than half of the area distorted were removed from the analysis and not scored.

The H-score for each core was calculated as follow: % of TREM2+ cells×Intensity score. For example, if a core had an IHC score of 2 (50%) and a moderate staining intensity (2), the calculated H-score will be: 50×2=100.

Results

Figures 12I, 12J, 12K, 12L:
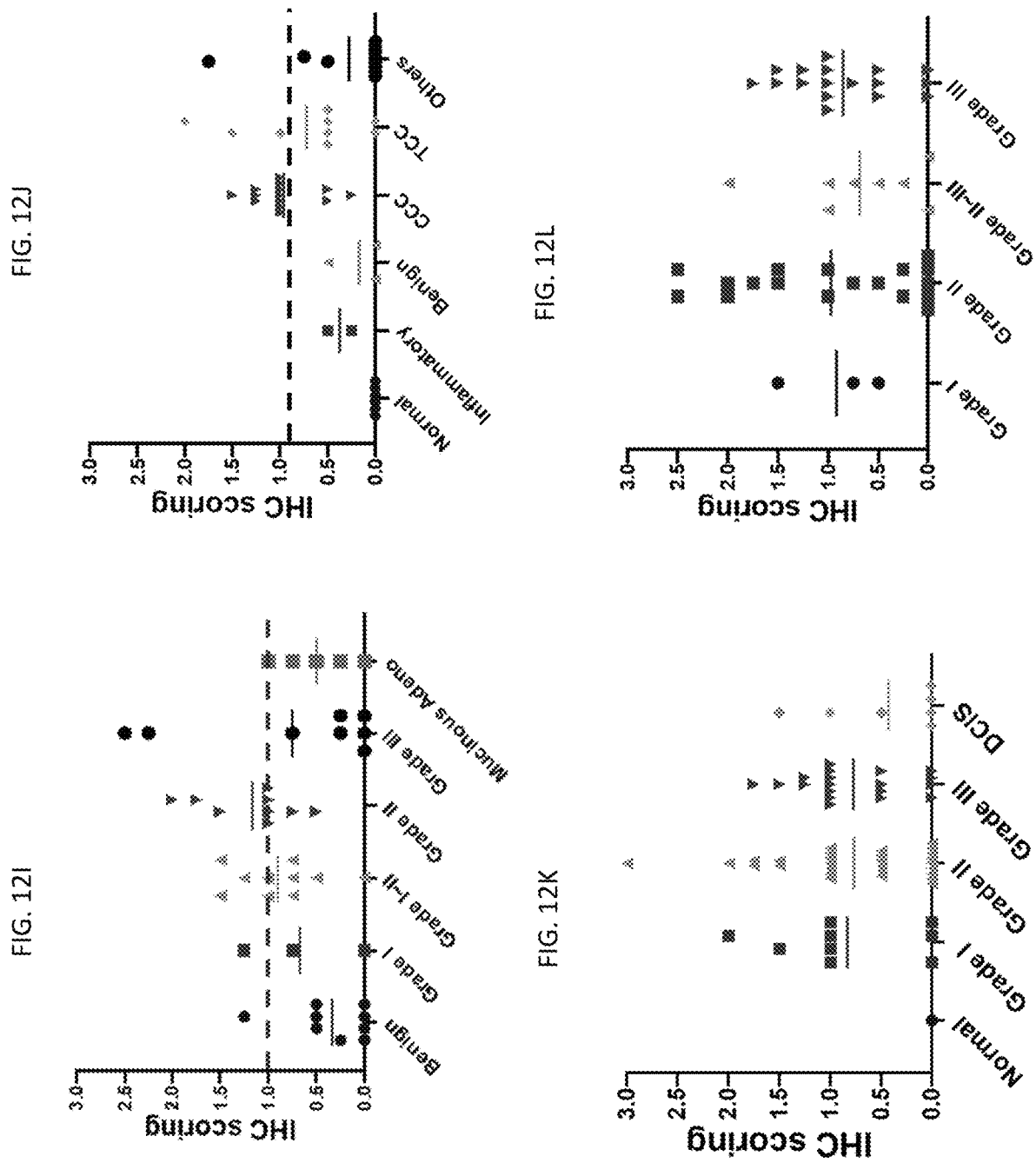
FIG. 12I shows TREM2 expression in colon cancers.
FIG. 12J shows TREM2 expression in kidney cancers.
FIG. 12K shows TREM2 expression in breast cancers.
FIG. 12L shows TREM2 expression in TNBC cancers.

FIG. 12A shows that TREM2 expression increases at Grade II and Grade III in ovarian cancer using the IHC staining and scoring method. FIG. 12B shows that TREM2 expression increases at Grade II and Grade III in ovarian cancer using the H-score staining and scoring method. 16 of 30 (53.3%) ovarian cancers were TREM2 positive. FIG. 12C shows that TREM2 expression increases at Grade I, Grade II, and Grade III in gastric cancer, as well as in Signet ring cell carcinoma and gastric undifferentiated carcinoma. FIG. 12D shows that TREM2 expression increases at Grade I, Grade II, and Grade III in liver cancer, as well as cholangiocarcinoma. FIG. 12E shows that TREM2 expression increases at Grade II and Grade III in prostate cancer. FIG. 12F shows that TREM2 expression increases in ductal adenocarcinoma in pancreatic cancer. FIG. 12G shows that TREM2 expression increases at Grade I-II in bladder cancer. FIG. 12H shows that there is significant TREM2 expression in lung cancers. FIG. 12I shows that there is significant TREM2 expression in colon cancers. FIG. 12J shows that there is significant TREM2 expression in kidney cancers. FIG. 12K shows that there is increased TREM2 expression in breast cancer at all grades. FIG. 12L shows that there is TREM2 expression in TNBC cancers. FIG. 12M shows that there is significant TREM2 expression in endometrial cancers and that the ~85% of tested TMA samples show positivity across all grades. As seen in FIG. 12N, lung adenocarcinoma samples expressed slightly higher levels of TREM2 compared to lung squamous cell carcinoma samples and therefore, 77 additional lung adenocarcinoma samples were tested to improve the confidence of this test. FIG. 12O shows significant TREM2 expression in lung adenocarcinomas as well as additional lung cancer subtypes. Table 9 provides a summary of TREM2 expression positively correlated with disease grade and negatively correlated with survival. TREM2 expression was determined using an internal IHC score for 48-150 subjects per indication.

TABLE 9

| Indication | CPI Approved | Expression correlation with disease grade (IHC) | >30% TREM2 Positive | Negative correlation with survival |
|---|---|---|---|---|
| Gastric | Yes | + | ~75% | + |
| Lung | Yes | − | ~50% | + |
| Liver | Yes | + | ~50% | + |
| Bladder | Yes | + | ~55% | + |
| H&N | Yes | | | − |
| Cervical | Yes | | | |
| Melanoma | Yes | | | − |
| Kidney | Yes | − | ~45% | + |
| TNBC | Yes | − | ~50% | − |
| Ovarian | No | + | ~40% | + |
| Pancreatic | No | + | ~50% | + |
| Prostate | No | + | ~35% | + |
| Colon (MSI$^{low}$) | No | − | ~60% | + |
| BC (non-TNBC) | No | − | ~50% | − |

Example 14: Anti-TREM2 Antibody Depletes M2-Like TAMs

Materials and Methods

Female BALB/c mice were injected with 1×106 EMT6 cells to establish subcutaneous tumors as described in Example 11. Mice were dosed with 30 mg/kg isotype antibody or afuc-PI-7012 twice five day s apart, once the average tumor volume reached >200 cubic mm. Tumor volumes were calculated as previously described. Tumors were harvested two days post second dose. Fat and fibrous material were removed from the tumors by dissection. The tumors were then weighed and processed for single-cell suspension by a combination of mechanical and enzymatic dissociation. After mincing the tissues, tumors were enzymatically digested using an optimized enzyme cocktail (Miltenyi Biotec, Tumor Dissociation Kit, mouse 130-096-830) with gentleMACS C tubes (Miltenyi Biotec, 130-093-235) in a gentleMACS Octo Dissociator (Miltenyi Biotec, 130-095-937). After dissociation, the sample was applied to a filter to remove any remaining larger particles. Single cell suspension of tumor tissues were surface stained using a panel of antibodies for flow cytometry. The antibody panel for evaluating myeloid subsets included antibodies specific for CD45, XCR1, F4/80, CD64, CD11c, Ly6C, CD11b, Ly6G, CD24, MHC class II as well as lineage markers in the dump channel (CD45R, CD90.2, CD3e, NKp46, CD19, Siglec F). The antibody panel for evaluating lymphoid subsets included antibodies specific for CD45, CD4, CD25, B220, NKp46, CD44, CD90.2, CD8a, CD11b, and CD49b. All data were collected on an Attune flow cytometer (Thermo Fisher) and analyzed using FlowJo software.

Results

As shown in FIG. 13A, anti-TREM2 antibody treatment resulted in decreased tumor size in vivo. In addition, anti-TREM2 antibody therapy decreased the number of MHCII$^{low}$ TAMs and increased the number of MHCII$^{high}$ TAMs as compared to isotype antibody alone (FIG. 13B). Anti-TREM2 antibody therapy also increased the number of CD8+ T cells and NKp46+ NK cells as compared to isotype antibody alone (FIG. 13C).

MHCII$^{low}$ TAMs are also known as "M2-like" TAMs and have immunosuppressive activities such as blocking infiltration of CD8+ T cells and the expression and secretion of immunosuppressive factors IL-10 and TGFβ. MHCII$^{high}$ TAMs are also known as "M1-like" TAMs. Thus, as shown in this example, treatment with a TREM2 antibody resulted in a decrease in the total immunosuppressive M2-like TAMs and an increase in cells associated with anti-tumor immunity. e.g., CD8+ T cells, NKp46+ NK cells, and M1-like MHCII$^{high}$ TAMs.

Example 15: Cytokine and CD8$^+$ T Cell Stimulation with Anti-TREM2 and Anti-PD1 Antibodies Female BALB/c mice were injected with 1×10$^6$ CT26 cells to establish subcutaneous tumors as described in Example 11. Once tumors were approximately 1000 mm3, the mice were dosed with isotype antibody, anti-PD1 antibody (5 mg/kg), afuc-PI-7012 (15 mg/kg) or anti-PD1 and anti-TREM2 antibodies twice five days apart. Tumors were harvested two days post second dose. Fat and fibrous material were removed from the tumors by dissection. The tumors were then weighed and processed for single-cell suspension by a combination of mechanical and enzymatic dissociation. After mincing the tissues, tumors were enzymatically digested using an optimized enzyme cocktail (Miltenyi Biotec, Tumor Dissociation Kit, mouse 130-096-830) with gentleMACS C tubes (Miltenyi Biotec, 130-093-235) in a gentleMACS Octo Dissociator (Miltenyi Biotec, 130-095-937). After dissociation, the sample was spun gently to pellet cells, clarified supernatant was then collected and treated with protease inhibitors to inactivate the tumor dissociation enzymes (Thermo Fisher Scientific, Halt Protease Inhibitor Cocktail 100X, 78429). After collection of supernatant, the pelleted sample was applied to a filter to remove any remaining larger particles. For intratumoral cytokine levels, supernatants were then analyzed for cytokine composition via the Meso Scale Discovery analyte detection platform (Meso Scale Discovery, V-PLEX Mouse Cytokine 19-Plex Kit, K-15255D-1). For lymphocyte cytokine analysis, single-cell suspensions were stimulated with phorbol 12-myristate 13-acetate (PMA) (Sigma-Aldrich. P8139), ionomycin (Thermo Fisher Scientific, 124222) and brefeldin A (BFA) (Sigma-Aldrich. B7651-5MG) for 4 hours. Stimulated cells were then surface stained using a panel of antibodies for flow cytometry, which included antibodies specific for CD45, CD90.2, CD44, CD8a, CD4, CD44. Cells were then fixed and permeabilized (Thermo Fisher Scientific, Foxp3/Transcription Factor Staining Buffer Set, 00-5523-00) and stained with antibodies against granzyme B (BioLegend, 515406) TNF-α (BioLegend, 506328) and IFN-γ (BioLegend, 50584) and FOXP3 (BioLegend, 126406). Cells were analyzed via flow cytometry on an Attune flow cytometer and analyzed using FlowJo software.

Figure 14A:
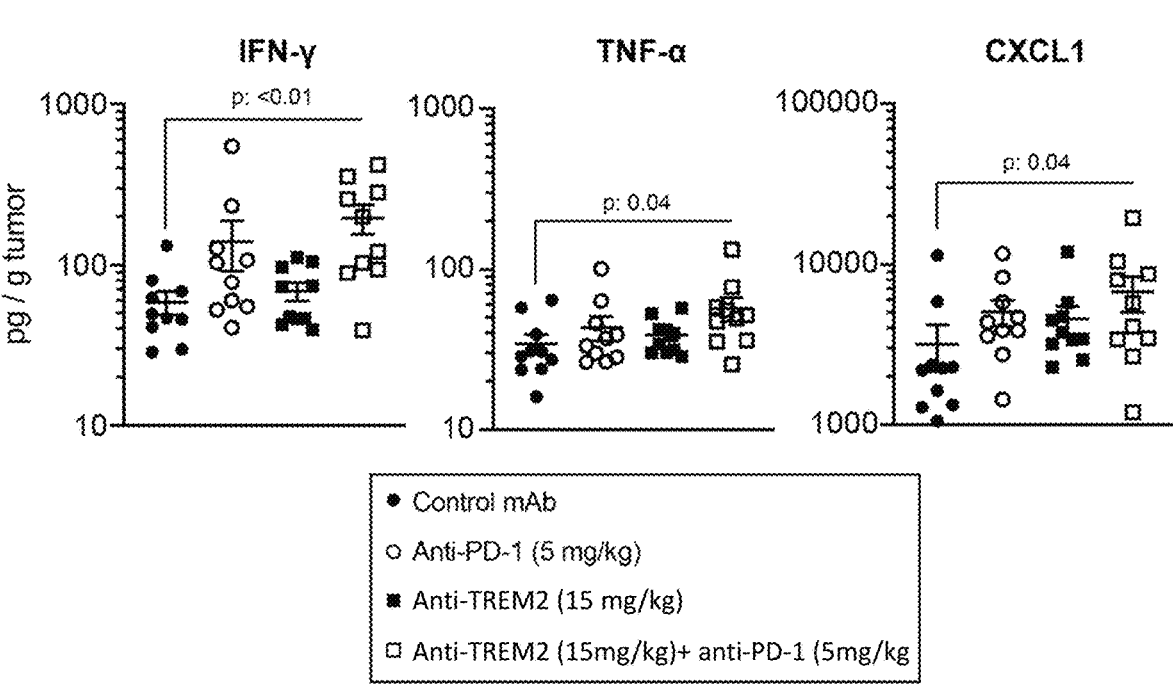
FIG. 14A shows production of pro-inflammatory cytokines IFN-γ, TNF-α, and CXCL1 after treatment with anti-TREM2 antibody and PD1 antibody.

As shown in FIG. 14A, the combination treatment of anti-TREM2 antibody and anti-PD1 antibody induced production of pro-inflammatory cytokines IFN-γ, TNF-α, and CXCL1. Although anti-TREM2 antibody treatment alone did not induce pro-inflammatory cytokines in this experiment, the combination of the TREM2 antibody and the PD1 antibody resulted in a greater production of cytokines than the PD-1 antibody alone.

Figure 14B:
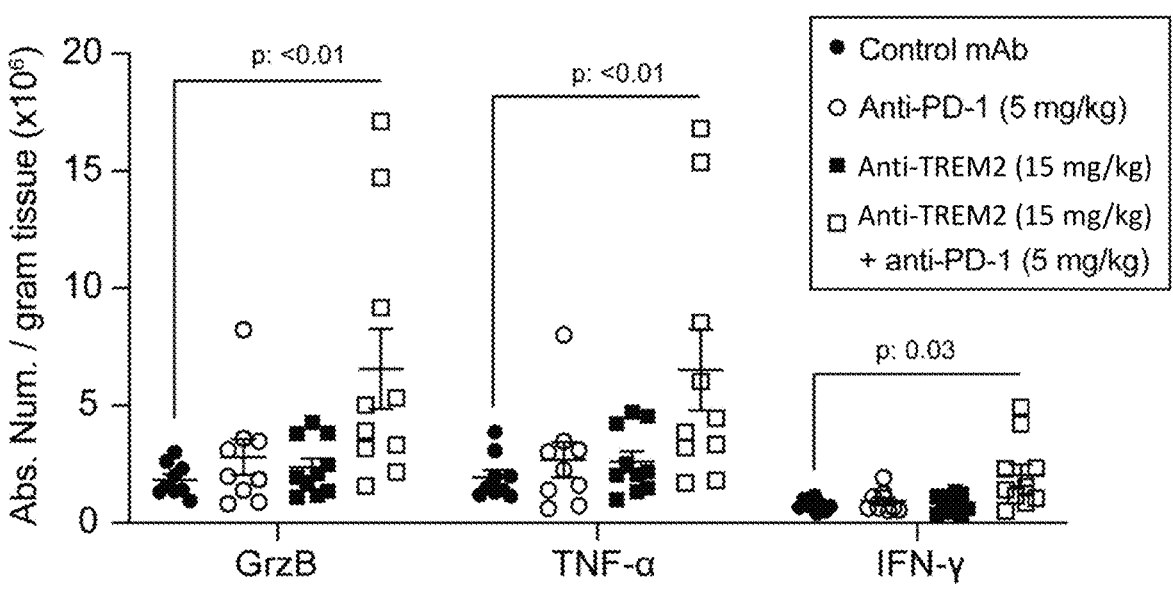
FIG. 14B shows increased numbers of CD8+ T cells that express granzyme B (GrzB), TNF-α, or IFN-γ, after treatment with both anti-TREM2 and anti-PD-1 antibodies.

In addition, the combination treatment of anti-TREM2 antibody and anti-PD1 antibody potentiated anti-tumor CD8+ T cells in the mice. As shown in FIG. 14B, anti-TREM2 and anti-PD1 antibodies alone had minimal effect on the number of CD8+ T cells expressing granzyme B (GrzB), TNF-α, or IFN-γ. However, the combination treatment of both anti-TREM2 and anti-PD-1 antibodies increased the number of CD8+ T cells that express granzyme B (GrzB), TNF-α, or IFN-γ.

Example 16: TREM2 Antibody Induces CXCL10 Secretion

C57BL/6 bone marrow mononuclear cells were harvested and incubated with 25 ng/ml CSF-1 for 6 days to differentiate them into bone marrow derived macrophages (BMDMs). The BMDMs were incubated with an increasing concentration of PI-7012, afuc-PI-7012, or isotype control antibodies for 24 hours. After incubation, the cell supernatants were then analyzed for cytokine composition via the Meso Scale Discovery analyte detection platform (Meso Scale Discovery, V-PLEX Mouse Cytokine 19-Plex Kit, K-15255D-1).

Figure 15:
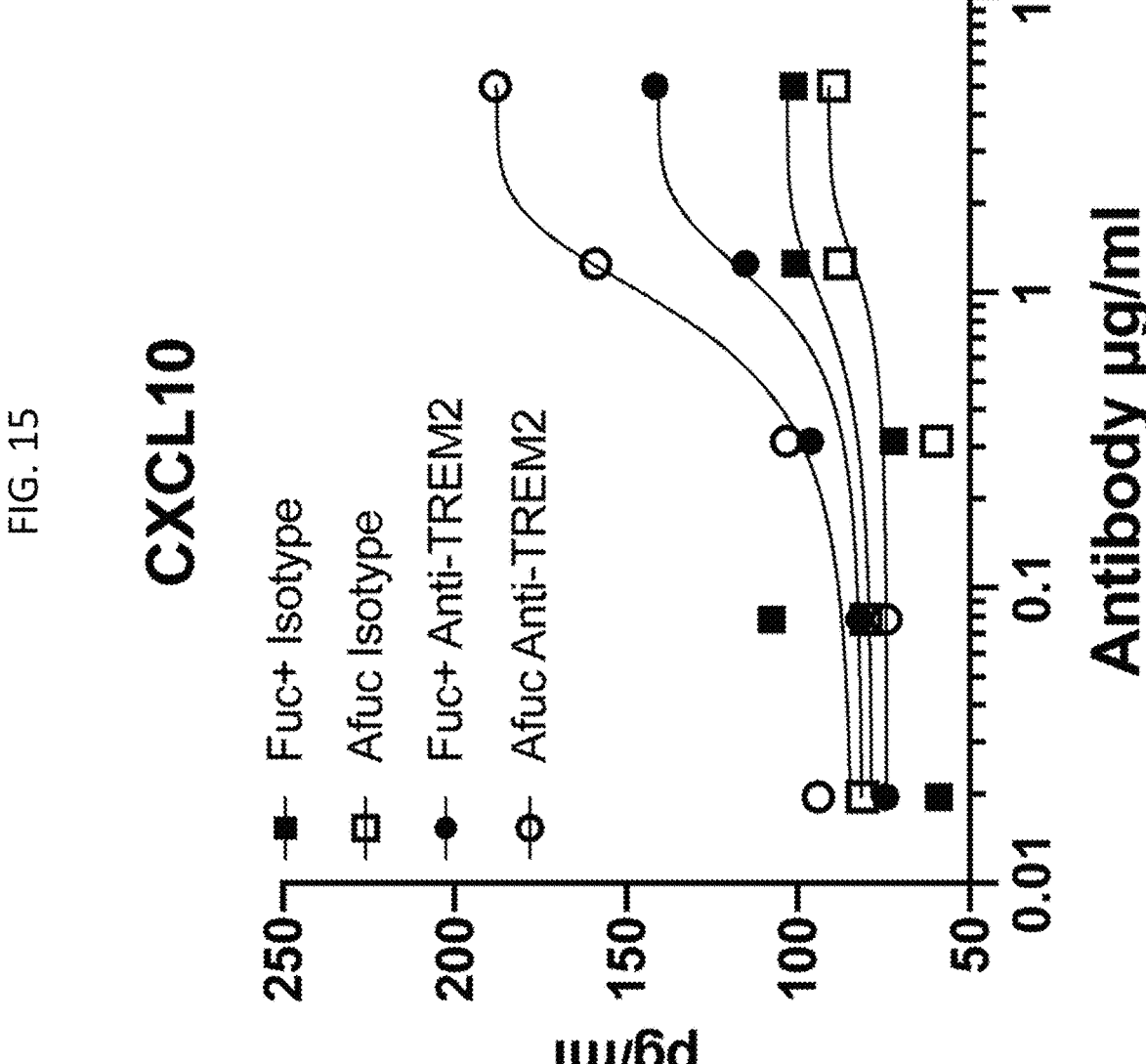
FIG. 15 shows a dose dependent increase in CXCL10 secretion by BMDMs after incubation with anti TREM2 antibodies.

As shown in FIG. 15, incubation with anti-TREM2 antibodies PI-7012 and afuc-PI-7012 induced a dose dependent increase in CXCL10 secretion by the BMDMs. The afucosylated TREM2 antibody had the greatest CXCL10 response. Thus. TREM2 antibody induced the BMDMs to secrete increased levels of chemokines.

Example 17: TREM2 Expression in Gastric Cancer

Level 2, RNAseq data from The Cancer Genome Atlas's cohort of gastric cancer samples were downloaded from the Broad Institute using firehose_get. RSEM values for TREM2 from both tumor and adjacent normal samples were converted to log 2 counts per million and plotted in R.

Prenormalized TREM2 expression profiles and associated clinical data across 192 gastric patients were downloaded from NCBI's GEO website (accession GSE15459). Expression profiles were divided into two cohorts based on median level of TREM2. Kaplan-Meier survival curves were plotted for each cohort and the associated logrank test was carried using the survival and survminer packages in R.

Figure 16:
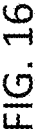
FIG. 16 shows TREM2 expression levels in gastric cancer inversely correlate with patient survival possibility.

As shown in FIG. 16, left panel, gastric cancer patients had increased expression of TREM2 as compared to normal tissue samples. In addition, TREM2 expression levels in gastric cancer inversely correlated with patient survival possibility (FIG. 16, right panel). Thus, TREM2 expression was elevated in gastric cancer patients and higher TREM2 expression lead to worse survival outcomes.

Example 18: TREM2 Expression in Ovarian Cancers

Materials and Methods

Normalized TREM2 expression profiles and associated clinical data across 285 ovarian patients were downloaded from NCBI's GEO website (accession GSE9899). Expression profiles were divided into three cohorts based on median, tercile, and quartile levels of TREM2 expression. Kaplan-Meier survival curves for each cohort were plotted and the associated logrank test was carried using the survival and survminer packages in R. The tercile cohort is the cohort with the top 33% TREM2 expression compared to the bottom 33% TREM2 expression and the quartile cohort is the top 25% TREM2 expression compared to the bottom 25% TREM2 expression The normalized TREM2 expression and clinical data from the ovarian dataset was also used to compare TREM2 expression and malignant tumor potential. Tumors were divided into two cohorts based on pathological examination of tumor phenotype and malignancy potential. TREM2 expression levels were compared across the two cohorts using the Wilcoxon rank sum test, as implemented in the R statistical programming language.

Results

FIG. 17A shows the median cohort survival curves, FIG. 17B shows the tercile cohort survival curves, and FIG. 17C shows the quartile cohort survival curves of patients with $TREM2^{low}$ and $TREM^{high}$ expression. TREM2 expression levels in ovarian cancer inversely correlated with patient survival possibility. In addition, higher TREM2 expression lead to worse survival outcomes as shown by the survival possibility of the median split cohort (top 50% TREM2 expression, p=0.0041, FIG. 17A) as compared to the tercile split cohort (top 33% TREM2 expression, p=0.0007, FIG. 17B) or quartile split cohort (top 25% TREM2 expression, p=0.00049, FIG. 17C).

Figure 18:
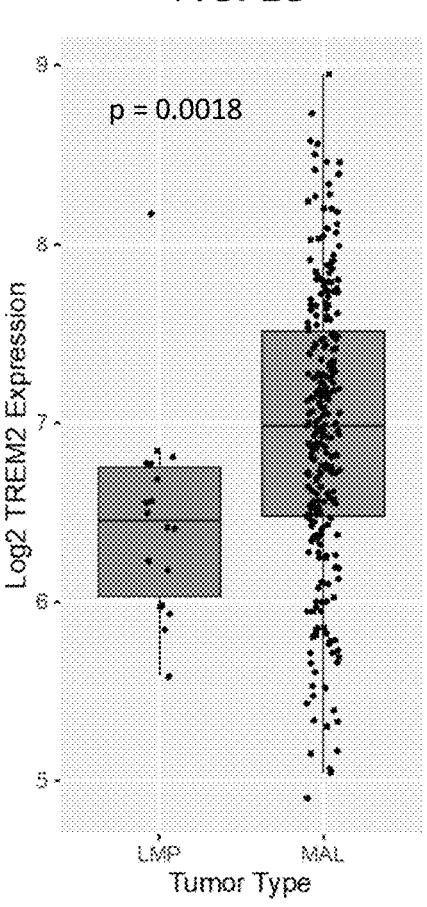
FIG. 18 shows TREM2 expression levels in ovarian cancer inversely correlate with tumor malignancy.

In addition, TREM2 expression correlated with malignancy in ovarian tumors (FIG. 18). Lower TREM2 expression was associated with tumors with low malignancy potential (LMP) while tumors with higher TREM2 expression were more likely to be malignant (MAL), p=0.0018.

Example 19: TREM2 is Predominately Expressed in Ovarian Tumor TAMs

Dissociated tumor cells (DTCs) from a single human ovarian patient were purchased from Discovery Life Sciences. Cells were flow cytometrically sorted for CD45 positivity to enrich for immune cells and encapsulated for single cell RNA sequencing using 10× Genomics' Chromium Controller. Resulting raw data was sequentially processed using 10×'s CellRanger program and the Seurat module in the R programming language. Cell populations in the resulting t-distributed stochastic neighbor embedding (tSNE) dimensionality reduction were manually annotated using cell-type specific marker genes and TREM2 expression was plotted. TREM2+ cells were defined as any cell with TREM2 expression.

Figure 20:
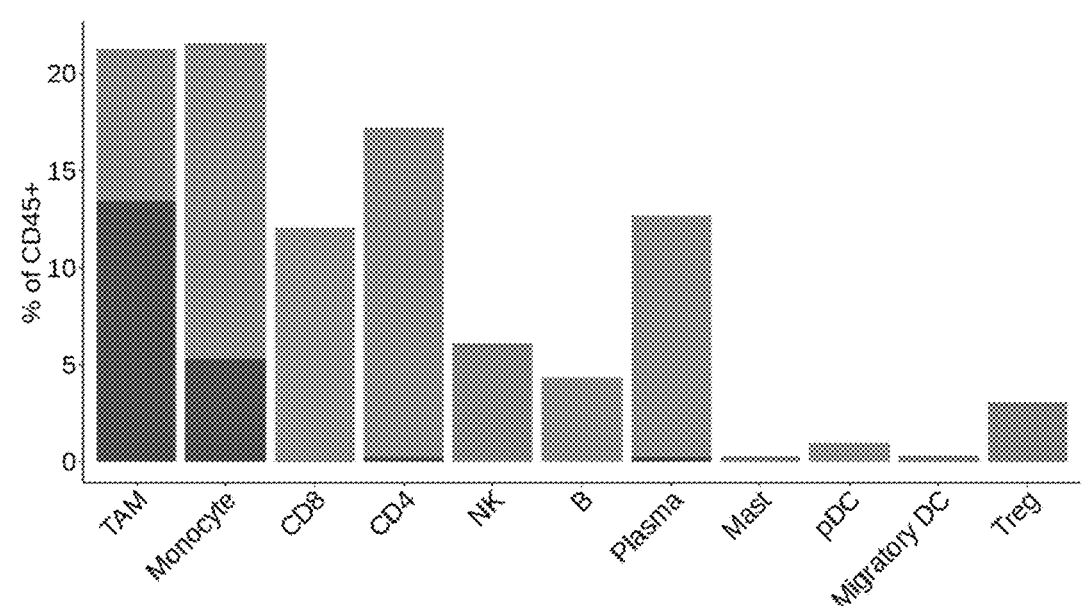
FIG. 20 shows that TREM2 is predominantly expressed on tumor associated macrophages (TAMs). Bars indicate the % of CD45+ immune infiltrate cell types isolated from ovarian tumors. Inset dark grey bars indicate the percent TREM2+ cells in each cell subset. TREM2 positive cells were found predominantly in the TAM and macrophage populations.

Analysis of single cell sequencing results from CD45+ immune infiltrate sorted from human ovarian tumor dissociated cells showed that TREM2 is predominantly expressed on tumor associated macrophages (TAMs) (FIG. 20, TREM2+ cell percentage shown in dark gray).

Example 20: Soluble TREM2 Levels in Ovarian Cancer

Materials and Methods

Plasma concentrations of soluble human TREM2 in ovarian cancer samples were determined as described below.

Human soluble TREM2 (hsTREM2) in plasma samples obtained from commercial vendors was quantified via a sandwich immunoassay developed on the MSD platform. A biotinylated mouse monoclonal antibody raised against human TREM2 (clone 7245, antibody developed in-house) was used as the capture agent and bound to precoated streptavidin plate. After washing, plasma samples from ovarian cancer patients (n=28) or non-cancer patients (n=32), were added to the plate. Soluble TREM2 protein in the samples bound to the capture antibody and was detected by a sulfo-tagged mouse monoclonal antibody against hTREM2 (clone 7222, antibody developed in-house). The bound soluble TREM2 was then quantitated via electro-chemiluminescence (ECL).

The MSD hsTREM2 assay has a dynamic range of 30 ng/mL to 41 µg/mL. The LLOQ and LOD of this assay are 41 µg/mL and 2.4 µg/mL, respectively. This hsTREM2 assay is able to detect circulating TREM2 proteins in plasma samples.

Results

Figure 19:
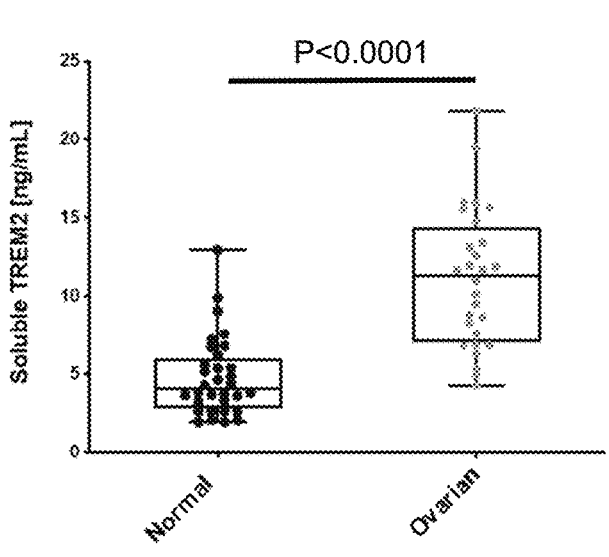
FIG. 19 shows a comparison of the amount of soluble TREM2 (ng/ml) in ovarian plasma samples and normal non-cancer plasma samples.

Increased levels of soluble human TREM2 was detected in ovarian cancer plasma samples. FIG. 19 shows a comparison of the amount of soluble TREM2 (ng/ml) in ovarian plasma samples and normal non-cancer plasma samples. Patients with ovarian cancer had a greater amount of soluble TREM2 in their serum. The average TREM2 plasma concentration in ovarian samples was 11.11 ng/ml, while the average TREM2 plasma concentration in non-cancer samples was 4.8 ng/ml, p=<0.0001.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES

1. Nimmerjahn, F. & Ravetch, J. V. Divergent Immuno-globulin G Subclass Activity Through Selective Fc Receptor Binding. *Science* (80-.). 310, 1510 LP-1512 (2005).
2. Ford, J. W. & McVicar, D. W. TREM and TREM-like receptors in inflammation and disease. *Curr. Opin. Immunol.* 21, 38-46 (2009).
3. Colonna, M. TREMs in the immune system and beyond. *Nat. Rev. Immunol.* 3, 445 (2003).
4. Takahashi, K., Rochford, C. D. P. & Neumann, H. Clearance of apoptotic neurons without inflammation by microglial triggering receptor expressed on myeloid cells-2. *J. Exp. Med.* 201, 647 LP-657 (2005).
5. Piccio. L. et al. Blockade of TREM-2 exacerbates experimental autoimmune encephalomyelitis. *Eur. J. Immunol.* 37, 1290-1301 (2007).
6. Broz, M. L. et al. Dissecting the Tumor Myeloid Compartment Reveals Rare Activating Antigen-Presenting Cells Critical for T Cell Immunity. *Cancer Cell* 26, 638-652 (2017).

| | | Sequences |
|---|---|---|
| SEQ ID NO | Name | Sequence |
| 1 | 37012_VH | EVQLLESGGGLVQPGGSLRLSCAASGFTFSNYYMAWVRQAPGKGLEWVSSLTNS GGSTYYADSVKGRFTISRDNSKNTLYLQMNSLRAEDTAVYYCTREWAGSGYFDY WGQGTLVTVSS |
| 2 | 37012_VL | DIQMTQSPSSLSASVGDRVTITCKASQNVGNNLAWYQQKPGKAPKLLIYYTSNR FTGVPSRFSGSGSGTDFTLTISSLQPEDFATYYCQRIYNSPWTFGQGTKLEIK |
| 3 | 37013_VH | EVQLLESGGGLVQPGGSLRLSCAASGFTFSNYYMAWVRQAPGKGLEWVSSLTNS GGSTYYADSVKGRFTISRDNSKNTLYLQMNSLRAEDTAVYYCTREWAGSGYFDY WGQGTLVTVSS |
| 4 | 37013_VL | DIQMTQSPSSLSASVGDRVTMTCKASQNVGNNLAWYQQKPGKAPKLLLYYTSNR FTGVPSRFSGSGSGTDFTLTISSVQPEDFATYYCQRIYNSPWTFGQGTKLELK |
| 5 | 37014_VH | EVQLLESGGGLVQPGGSLRLSCAASGFTFSNYYMAWVRQAPGKGLEWVASLTNS GGSTYYADSVKGRFTLSRDNSKNTLYLQMNSLRAEDTAVYYCTREWAGSGYFDY WGQGTLVTVSS |
| 6 | 37014_VL | DIQMTQSPSSLSASVGDRVTITCKASQNVGNNLAWYQQKPGKAPKLLIYYTSNR FTGVPSRFSGSGSGTDFTLTISSLQPEDFATYYCQRIYNSPWTFGQGTKLEIK |
| 7 | 37017_VH | EVQLLESGGGLVQPGGSLRLSCAASGFTFSNYYMAWVRQAPGKGLEWVSSLTNS GGSTYYADSVKGRFTISRDNSKNTLYLQMNSLRAEDTAVYY<u>C</u>AKEWAGSGYFDY WGQGTLVTVSS |
| 8 | 37017_VL | DIQMTQSPSSLSASVGDRVTITCKASQNVGNNLAWYQQKPGKAPKLLIYYTSNR FTGVPSRFSGSGSGTDFTLTISSLQPEDFATYYCQRIYNSPWTFGQGTKLEIK |
| 9 | CDR-H1 | FSNYYMA |
| 10 | CDR-H2 | SLTNSGGSTY |
| 11 | CDR-H3 | EWAGSGY |
| 12 | CDR-L1 | NVGNNLA |

-continued

| Sequences | | |
|---|---|---|

| SEQ ID NO | Name | Sequence |
|---|---|---|
| 13 | CDR-L2 | YTSNRFT |
| 14 | CDR-L3 | RIYNSPW |
| 15 | TREM2 Human Protein | MEPLRLLILLFVTELSGAHNTTVFQGVAGQSLQVSCPYDSMKHWGRRKAWCRQL GEKGPCQRVVSTHNLWLLSFLRRWNGSTAITDDTLGGTLTITLRNLQPHDAGLY QCQSLHGSEADTLRKVLVEVLADPLDHRDAGDLWFPGESESFEDAHVEHSISRS LLEGEIPFPPTSILLLLACIFLIKILAASALWAAAWHGQKPGTHPPSELDCGHD PGYQLQTLPGLRDT |
| 16 | TREM2 Nucleotide (CDS) | ATGGAGCCTCTCCGGCTGCTCATCTTACTCTTTGTCACAGAGCTGTCCGGAGCC CACAACACCACAGTGTTCCAGGGCGTGGCGGGCCAGTCCCTGCAGGTGTCTTGC CCCTATGACTCCATGAAGCACTGGGGGAGGCGCAAGGCCTGGTGCCGCCAGCTG GGAGAGAAGGGCCCATGCCAGCGTGTGGTCAGCACGCACAACTTGTGGCTGCTG TCCTTCCTGAGGAGGTGGAATGGGAGCACAGCCATCACAGACGATACCCTGGGT GGCACTCTCACCATTACGCTGCGGAATCTACAACCCCATGATGCGGGTCTCTAC CAGTGCCAGAGCCTCCATGGCAGTGAGGCTGACACCCTCAGGAAGGTCCTGGTG GAGGTGCTGGCAGACCCCCTGGATCACCGGGATGCTGGAGATCTCTGGTTCCCC GGGGAGTCTGAGAGCTTCGAGGATGCCCATGTGGAGCACAGCATCTCCAGGAGC CTCTTGGAAGGAGAAATCCCCTTCCCACCCACTTCCATCCTTCTCCTCCTGGCC TGCATCTTTCTCATCAAGATTCTAGCAGCCAGCGCCCTCTGGGCTGCAGCCTGG CATGGACAGAAGCCAGGGACACATCCACCCAGTGAACTGGACTGTGGCCATGAC CCAGGGTATCAGCTCCAAACTCTGCCAGGGCTGAGAGACACGTGA |
| 17 | TREM2 Mouse Protein | MGPLHQFLLLLITALSQALNTTVLQGMAGQSLRVSCTYDALKHWGRRKAWCRQL GEEGPCQRVVSTHGVWLLAFLKKRNGSTVIADDTLAGTVTITLKNLQAGDAGLY QCQSLRGREAEVLQKVLVEVLEDPLDDQDAGDLWVPEESSSFEGAQVEHSTSRN QETSFPPTSILLLLACVLLSKFLAASILWAVARGRQKPGTPVVRGLDCGQDAGH QLQILTGPGGT |
| 18 | Frame H1 | EVQLLESGGGLVQPGGSLRLSCAASGFTFSNYYMAWVRQAPGKGLEWVSSLTNS GGSTYYADSVKGRFTISRDNSKNTLYLQMNSLRAEDTAVYYCAKEWAGSGYFDY WGQGTLVTVSS |
| 19 | Frame H2 | EVQLLESGGGLVQPGGSLRLSCAASGFTFSNYYMAWVRQAPGKGLEWVSSLTNS GGSTYYADSVKGRFTISRDNSKNTLYLQMNSLRAEDTAVYYCTREWAGSGYFDY WGQGTLVTVSS |
| 20 | Frame H3 | EVQLLESGGGLVQPGGSLRLSCAASGFTFSNYYMAWVRQAPGKGLEWVASLTNS GGSTYYADSVKGRFTLSRDNSKNTLYLQMNSLRAEDTAVYYCTREWAGSGYFDY WGQGTLVTVSS |
| 21 | 3-23*01 Frame VH | EVQLLESGGGLVQPGGSLRLSCAASGFTFSSYAMSWVRQAPGKGLEWVSAISGS GGSTYYADSVKGRFTISRDNSKNTLYLQMNSLRAEDTAVYYCAKWGQGTLVTVS S |
| 22 | Frame L1 | DIQMTQSPSSLSASVGDRVTITCKASQNVGNNLAWYQQKPGKAPKLLIYYTSNR FTGVPSRFSGSGSGTDFTLTISSLQPEDFATYYCQRIYNSPWTFGQGTKLEIK |
| 23 | Frame L2 | DIQMTQSPSSLSASVGDRVTMTCKASQNVGNNLAWYQQKPGKAPKLLLYYTSNR FTGVPSRFSGSGSGTDFTLTISSVQPEDFATYYCQRIYNSPWTFGQGTKLELK |
| 24 | 3-23*01 Frame VL | DIQMTQSPSSLSASVGDRVTITCRASQSISSYLNWYQQKPGKAPKLLIYAASSL QSGVPSRFSGSGSGTDFTLTISSLQPEDFATYYCQQSYSTPPFGQGTKLEIK |
| 25 | Full 37012_H | EVQLLESGGGLVQPGGSLRLSCAASGFTFSNYYMAWVRQAPGKGLEWVSSLTNS GGSTYYADSVKGRFTISRDNSKNTLYLQMNSLRAEDTAVYYCTREWAGSGYFDY WGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYPSD IAVEWESNGQPENNYKTTPPVLDSDGSFFLYSKLTVDKSRWQQGNVFSCSVMHE ALHNHYTQKSLSLSPGK |
| 26 | Full 37012_L | DIQMTQSPSSLSASVGDRVTITCKASQNVGNNLAWYQQKPGKAPKLLIYYTSNR FTGVPSRFSGSGSGTDFTLTISSLQPEDFATYYCQRIYNSPWTFGQGTKLEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| 27 | Full 37013_H | EVQLLESGGGLVQPGGSLRLSCAASGFTFSNYYMAWVRQAPGKGLEWVSSLTNS GGSTYYADSVKGRFTISRDNSKNTLYLQMNSLRAEDTAVYYCTREWAGSGYFDY WGQGTLVTVSSASTKGPSVFPLAPSSKSTSGGTAALGCLVKDYFPEPVTVSWNS |

-continued

| | Sequences | |
| --- | --- | --- |

SEQ
ID NONName        Sequence

```
                GALTSGVHTFPAVLQSSGLYSLSSVVTVPSSSLGTQTYICNVNHKPSNTKVDKK
                VEPKSCDKTHTCPPCPAPELLGGPSVFLFPPKPKDTLMISRTPEVTCVVVDVSH
                EDPEVKFNWYVDGVEVHNAKTKPREEQYNSTYRVVSVLTVLHQDWLNGKEYKCK
                VSNKALPAPIEKTISKAKGQPREPQVYTLPPSRDELTKNQVSLTCLVKGFYPSD
                IAVEWESNGQPENNYKTTPPVLDSDGSFFLYSKLTVDKSRWQQGNVFSCSVMHE
                ALHNHYTQKSLSLSPGK

28  Full    DIQMTQSPSSLSASVGDRVTMTCKASQNVGNNLAWYQQKPGKAPKLLLYYTSNR
    37013_L  FTGVPSRFSGSGSGTDFTLTISSVQPEDFATYYCQRIYNSPWTFGQGTKLELKR
             TVAAPSVFIFPPSDEQLKSGTASVVCLLNNFYPREAKVQWKVDNALQSGNSQES
             VTEQDSKDSTYSLSSTLTLSKADYEKHKVYACEVTHQGLSSPVTKSFNRGEC 29  Full    EVQLLESGGGLVQPGGSLRLSCAASGFTFSNYYMAWVRQAPGKGLEWVASLTNS
    37014_H  GGSTYYADSVKGRFTLSRDNSKNTLYLQMNSLRAEDTAVYYCTREWAGSGYFDY
             WGQGTLVTVSSASTKGPSVFPLAPSSKSTSGGTAALGCLVKDYFPEPVTVSWNS
             GALTSGVHTFPAVLQSSGLYSLSSVVTVPSSSLGTQTYICNVNHKPSNTKVDKK
             VEPKSCDKTHTCPPCPAPELLGGPSVFLFPPKPKDTLMISRTPEVTCVVVDVSH
             EDPEVKFNWYVDGVEVHNAKTKPREEQYNSTYRVVSVLTVLHQDWLNGKEYKCK
             VSNKALPAPIEKTISKAKGQPREPQVYTLPPSRDELTKNQVSLTCLVKGFYPSD
             IAVEWESNGQPENNYKTTPPVLDSDGSFFLYSKLTVDKSRWQQGNVFSCSVMHE
             ALHNHYTQKSLSLSPGK 30  Full    DIQMTQSPSSLSASVGDRVTITCKASQNVGNNLAWYQQKPGKAPKLLIYYTSNR
    37014_L  FTGVPSRFSGSGSGTDFTLTISSLQPEDFATYYCQRIYNSPWTFGQGTKLEIKR
             TVAAPSVFIFPPSDEQLKSGTASVVCLLNNFYPREAKVQWKVDNALQSGNSQES
             VTEQDSKDSTYSLSSTLTLSKADYEKHKVYACEVTHQGLSSPVTKSFNRGEC 31  Full    EVQLLESGGGLVQPGGSLRLSCAASGFTFSNYYMAWVRQAPGKGLEWVSSLTNS
    37017_H  GGSTYYADSVKGRFTISRDNSKNTLYLQMNSLRAEDTAVYYCAKEWAGSGYFDY
             WGQGTLVTVSSASTKGPSVFPLAPSSKSTSGGTAALGCLVKDYFPEPVTVSWNS
             GALTSGVHTFPAVLQSSGLYSLSSVVTVPSSSLGTQTYICNVNHKPSNTKVDKK
             VEPKSCDKTHTCPPCPAPELLGGPSVFLFPPKPKDTLMISRTPEVTCVVVDVSH
             EDPEVKFNWYVDGVEVHNAKTKPREEQYNSTYRVVSVLTVLHQDWLNGKEYKCK
             VSNKALPAPIEKTISKAKGQPREPQVYTLPPSRDELTKNQVSLTCLVKGFYPSD
             IAVEWESNGQPENNYKTTPPVLDSDGSFFLYSKLTVDKSRWQQGNVFSCSVMHE
             ALHNHYTQKSLSLSPGK 32  Full    DIQMTQSPSSLSASVGDRVTITCKASQNVGNNLAWYQQKPGKAPKLLIYYTSNR
    37017_L  FTGVPSRFSGSGSGTDFTLTISSLQPEDFATYYCQRIYNSPWTFGQGTKLEIKR
             TVAAPSVFIFPPSDEQLKSGTASVVCLLNNFYPREAKVQWKVDNALQSGNSQES
             VTEQDSKDSTYSLSSTLTLSKADYEKHKVYACEVTHQGLSSPVTKSFNRGEC 33  Rat      EVQLVESGGG LVQPGRSLKL SCAASGFTFS NYYMAWVRQA PTKGLEWVAS
    IgG2B    LTNSGGSTYY RDSVKGRFTL SRDNAKSTLY LQMDSLRSED TATYYCTREW
    clone #  AGSGYFDYWG QGVMVTVSSA QTTAPSVYPL APGCGDTTSS TVTLGCLVKG
    237920   YFPEPVTVTW NSGALSSDVH TFPAVLQSGL YTLTSSVTSS TWPSQTVTCN
    heavy    VAHPASSTKV DKKVERRDGG IGHKCPTCPT CHKCPVPELL GGPSVFLFPP
    chain    KPKDILLLSQ NAKVTCVVVD VSEEEPDVQF SWFVNNVEVH TAQTQPREEQ
             YNSTFRVVSA LPLQHQDWMS GKEFKCKVNN KALPSPIEKT LSKPKGLVRK
             PQVYVMGPPT EQLTEQTVSL TCLTSGFLPN DIGVEWTSNG HIEKNYKNTE
             PVMDSDGSFF MYSKLNVERS RWDSRAPFVC SVVHEGLHNH HVEKSLSRPP
             G 34  Rat      NIVMTQSPKS MSLSVGDRVT MNCKASQNVG NNLAWYQQKP GQSPKLLLYY
    IgG2B    TSNRFTGVPD RFTGGGYGTD FTLTINSVQA EDAAFYYCQR IYNSPWTFGG
    clone #  GTKLELKRAD AAPTVSIFPP STEQLATGGA SVVCLMNNFY PRDISVKWKI
    237920   DGTERRDGVL DSVTDQDSKD STYSMSSTLS LTKADYESHN LYTCEVVHKT
    light    SSSPVVKSFN RNEC
    chain 35  PI-7012  EVQLVESGGGLVQPGRSLKLSCAASGFTFSNYYMAWVRQAPTKGLEWVASLTNS
    AB VH    GGSTYYRDSVKGRFTLSRDNAKSTLYLQMDSLRSEDTATYYCTREWAGSGYFDY
             WGQGVMVTVSS 36  PI-7012  NIVMTQSPKSMSLSVGDRVTMNCKASQNVGNNLAWYQQKPGQSPKLLLYYTSNR
    AB VL    FTGVPDRFTGGGYGTDFTLTINSVQAEDAAFYYCQRIYNSPWTFGGGTKLELK 37  PI-7012  EVQLVESGGGLVQPGRSLKLSCAASGFTFSNYYMAWVRQAPTKGLEWVASLTNS
    Heavy    GGSTYYRDSVKGRFTLSRDNAKSTLYLQMDSLRSEDTATYYCTREWAGSGYFDY
    chain    WGQGVMVTVSSAKTTAPSVYPLAPVCGDTTGSSVTLGCLVKGYFPEPVTLTWNS
             GSLSSGVHTFPAVLQSDLYTLSSSVTVTSSTWPSQSITCNVAHPASSTKVDKKI
             EPRGPTIKPCPPCKCPAPNLLGGPSVFIFPPKIKDVLMISLSPIVTCVVVDVSE
             DDPDVQISWFVNNVEVHTAQTQTHREDYNSTLRVVSALPIQHQDWMSGKEFKCK
             VNNKDLPAPIERTISKPKGSVRAPQVYVLPPPEEEMTKKQVTLTCMVTDFMPED
```

-continued

| Sequences | | |
|---|---|---|

| SEQ ID NO | Name | Sequence |
|---|---|---|
| | | IYVEWTNNGKTELNYKNTEPVLDSDGSYFMYSKLRVEKKNWVERNSYSCSVVHE GLHNHHTTKSFSRTPGK |
| 38 | PI-7012 Light Chain | NIVMTQSPKSMSLSVGDRVTMNCKASQNVGNNLAWYQQKPGQSPKLLLYYTSNR FTGVPDRFTGGGYGTDFTLTINSVQAEDAAFYYCQRIYNSPWTFGGGTKLELKR ADAAPTVSIFPPSSEQLTSGGASVVCFLNNFYPKDINVKWKIDGSERQNGVLNS WTDQDSKDSTYSMSSTLTLTKDEYERHNSYTCEATHKTSTSPIVKSFNRNEC |
| 39 | CDR-H1 | GFTFSNYYMA |
| 40 | CDR-H2 | SLTNSGGSTY |
| 41 | CDR-H3 | EWAGSGYFDY |
| 42 | CDR-L1 | KASQNVGNNLA |
| 43 | CDR-L2 | YTSNRFT |
| 44 | CDR-L3 | QRIYNSPWT |
| 45 | | GFTFSNY |
| 46 | | NYYMA |
| 47 | | SNYYMA |
| 48 | | GFTFSNYY |
| 49 | | TNSGGS |
| 50 | | SLTNSGGSTYYADSVKG |
| 51 | | WVSSLTNSGGSTY |
| 52 | | LTNSGGST |
| 53 | | TREWAGSGYFD |
| 54 | | TREWAGSGYFDY |
| 55 | | GNNLAWY |
| 56 | | QNVGNN |
| 57 | | LLIYYTSNRF |
| 58 | | YT |
| 59 | | QRIYNSPW |

The invention claimed is:

1. A method of treating ovarian cancer in a subject in need thereof, comprising administering to the subject an isolated anti-TREM2 antibody comprising a variable heavy domain (VH) sequence comprising a CDR-H1, a CDR-H2, and a CDR-H3 and a variable light domain (VL) sequence comprising a CDR-L1, a CDR-L2, and a CDR-L3, and wherein:

a. the CDR-H1 comprises the sequence set forth in SEQ ID NO: 9 or 39, b. the CDR-H2 comprises the sequence set forth in SEQ ID NO: 10 or 40, c. the CDR-H3 comprises the sequence set forth in SEQ ID NO: 11 or 41, d. the CDR-L1 comprises the sequence set forth in SEQ ID NO: 12 or 42, e. the CDR-L2 comprises the sequence set forth in SEQ ID NO: 13 or 43, and f. the CDR-L3 comprises the sequence set forth in SEQ ID NO: 14 or 44.

2. The method of claim 1, wherein the antibody comprises:

a. the CDR-H1 comprises the sequence set forth in SEQ ID NO: 39, b. the CDR-H2 comprises the sequence set forth in SEQ ID NO: 40, c. the CDR-H3 comprises the sequence set forth in SEQ ID NO: 41, d. the CDR-L1 comprises the sequence set forth in SEQ ID NO: 42, e. the CDR-L2 comprises the sequence set forth in SEQ ID NO: 43, and f. the CDR-L3 comprises the sequence set forth in SEQ ID NO: 44.

3. The method of claim 1, wherein the antibody comprises the VH sequence shown in SEQ ID NO: 1, 3, or 5.

4. The method of claim 1, wherein the antibody comprises the VH sequence shown in SEQ ID NO: 1, 3, or 5 and the VL sequence shown in SEQ ID NO: 2, 4, or 6.

5. The method of claim 1, wherein the antibody comprises the VH sequence shown in SEQ ID NO: 1.

6. The method of claim 1, wherein the antibody comprises the VL sequence shown in SEQ ID NO: 2.

7. The method of claim 1, wherein the antibody comprises the VH sequence shown in SEQ ID NO: 1 and the VL sequence shown in SEQ ID NO: 2.

8. The method of claim 1, wherein the antibody comprises the heavy chain sequence shown in SEQ ID NO: 25 and the light chain sequence shown in SEQ ID NO: 26.

9. The method of claim 1, wherein the antibody binds to human TREM2 with a KD of less than or equal to $5.12 \times 10^{-9}$ M, as measured by surface plasmon resonance (SPR) assay.

10. The method of claim 1, wherein the antibody is capable of specifically killing, depleting, or disabling TREM2+ myeloid cells.

11. The method of claim 1, wherein the antibody has antibody-dependent cell-mediated cytotoxicity (ADCC) activity, antibody-mediated cellular phagocytosis (ADCP) activity or complement-dependent cytotoxicity (CDC) activity.

12. The method of claim 1, wherein the antibody is a monoclonal antibody.

13. The method of claim 1, wherein the antibody is afucosylated.

14. The method of claim 1, wherein the antibody comprises a heavy chain constant region of human IgG1.

15. The method of claim 1, wherein the subject has previously received, is concurrently receiving, or will subsequently receive an immunotherapy.

16. The method of claim 15, wherein the immunotherapy is at least one of: a checkpoint inhibitor; a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; and an epigenetic modulator.

17. The method of claim 16, wherein the immunotherapy is selected from the group consisting of: an anti-PD1 antibody, an anti-PDL1 antibody; or an anti-CTLA4 antibody.

* * * * *